US005576827A

United States Patent [19]
Strickland et al.

[11] Patent Number: 5,576,827
[45] Date of Patent: Nov. 19, 1996

[54] APPARATUS AND METHOD FOR DETERMINING THE SIZE DISTRIBUTION OF PARTICLES BY LIGHT SCATTERING

[75] Inventors: Michael L. Strickland, Marietta; James P. Olivier, Lawrenceville; William B. Conklin, Lawrenceville; Warren P. Hendrix, Lawrenceville, all of Ga.

[73] Assignee: Micromeritics Instrument Corporation, Norcross, Ga.

[21] Appl. No.: 228,965

[22] Filed: Apr. 15, 1994

[51] Int. Cl.$^6$ .................................................. G01N 15/02
[52] U.S. Cl. .............................................. 356/336; 356/343
[58] Field of Search .................................. 356/336, 338, 356/340, 343

[56] References Cited

U.S. PATENT DOCUMENTS

| | | | |
|---|---|---|---|
| 3,659,946 | 5/1972 | Kozawa et al. | 356/340 |
| 4,320,462 | 3/1982 | Lund et al. | 356/121 |
| 4,549,204 | 10/1985 | Bertero et al. | |
| 4,606,635 | 8/1986 | Miyazawa et al. | 356/240 |
| 4,676,641 | 6/1987 | Bott | 356/336 |
| 4,781,460 | 11/1988 | Bott | 356/336 |
| 4,953,978 | 9/1990 | Bott et al. | 356/336 |
| 5,007,737 | 4/1991 | Hirleman, Jr. | |
| 5,042,950 | 8/1991 | Salmon, Jr. | |
| 5,056,918 | 10/1991 | Bott et al. | 356/336 |
| 5,101,113 | 3/1992 | Hirleman, Jr. et al. | |
| 5,104,221 | 4/1992 | Bott et al. | 356/336 |
| 5,185,641 | 2/1993 | Igushi et al. | 356/336 |
| 5,282,151 | 1/1994 | Knollenberg | |

OTHER PUBLICATIONS

Sugrue, S. & Row, G., *LS Series Resolution*, Coulter Corporation, Hileah, FL (no date).
Row, G. & Bott, S., *LS Series Reproducibility*, Coulter Corporation, Hialeah, FL (no date).
*Laser Diffraction Particle Size Analysis*, Coulter Corporation, Hileah, FL (no date).

Fossum, E. R., "Active–Pixel Sensors Challenge CCDs", *Laser Focus World*, Jun. 1993, pp. 83–87.
Matsumoto, et al., "A New MOS Phototransistor Operating in a Non–Destructive Readout Mode", *Japanese Journal of Applied Physics*, vol. 24, No. 5, May 1985, pp. L323–L325.
Nakamura, T., et al., "A New MOS Image Sensor Operating in a Non–Destructive Readout Mode", *IEDM*, vol. 86, pp. 353–356.
*SICAM–A PC Compatible Digital Instrumentation Camera*, CID Technologies, Liverpool, NY.
Nikov, Z., et al., Evaluation of a Charge Injection Device Array, Rochester Institute of Technology, NY.

(List continued on next page.)

*Primary Examiner*—Richard A. Rosenberger
*Attorney, Agent, or Firm*—Jones & Askew

[57] ABSTRACT

An apparatus and method are disclosed for obtaining and analyzing light scattering data to determine the size distribution of a group of dispersed particles that scattered the light. The apparatus and method use a two-dimensional array of photosensitive pixels such as a charge-coupled device (CCD) or an array of solid-state photodiodes. The analyzer illuminates the particles with a dose of light in a collimated beam from a light source so as to scatter light of the beam, and at least a portion of the light interacting with the particles is detected with the photosensitive pixel array. The pixels are functionally equivalent and the analyzer dynamically configures and re-configures at least a portion of the pixels into a variable number of data collection areas which correspond to a selected set of scattering angles. The analyzer also determines whether and, from the pixel output data, where an unscattered center of the incident light beam intersects the pixel array. Thus, no precision mechanical alignment of the light source and the pixel array detector is required prior to operation of the analyzer. Furthermore, the ability of the analyzer to determine the unscattered beam center allows the analyzer to classify each of at least a portion of the pixels to data collection areas according to a function of the geometric relationship the pixel bears to the location of the beam center.

13 Claims, 35 Drawing Sheets

OTHER PUBLICATIONS

4MIP–4MIPTOOL *Interactive Image Analysis User's Manual,* EPIX Inc., Buffalo Grove, IL, pp. 17–1, 17–2.

Boxman, A., *Particle Size Measurment for Control of Industrial Crystallizers,* Doctoral Thesis, Delft University of Technology, 1992, pp. 125–176.

*Image Sensing Products,* EG & G Reticon, Sunnyvale, CA, 1986, pp. 3–1, 3–11 through 3–13, 3–17 through 3–24, and 4–1 through 4–10.

|     | 132 | 133 | 134 | 135 | 136 | 137 | 138 | 139 | 140 | 141 | 142 | 143 | 144 | 145 |
|-----|-----|-----|-----|-----|-----|-----|-----|-----|-----|-----|-----|-----|-----|-----|
| 118 | 0 | 0 | 0 | 0 | 0 | 0 | 0 | 0 | 0 | 0 | 0 | 0 | 0 | 0 |
| 119 | 0 | 0 | 0 | 0 | 0 | 0 | 0 | 0 | 0 | 0 | 0 | 0 | 0 | 0 |
| 120 | 0 | 0 | 0 | 0 | 0 | 0 | 0 | 0 | 0 | 0 | 0 | 0 | 0 | 0 |
| 121 | 0 | 0 | 0 | 1 | 1 | 0 | 0 | 0 | 0 | 0 | 0 | 0 | 0 | 0 |
| 122 | 0 | 0 | 0 | 2 | 1 | 0 | 0 | 0 | 0 | 0 | 0 | 0 | 0 | 0 |
| 123 | 0 | 0 | 0 | 2 | 2 | 0 | 0 | 0 | 0 | 0 | 0 | 0 | 0 | 0 |
| 124 | 0 | 0 | 0 | 3 | 4 | 0 | 0 | 0 | 0 | 0 | 0 | 0 | 0 | 0 |
| 125 | 0 | 0 | 1 | 4 | 9 | 1 | 0 | 0 | 0 | 0 | 0 | 0 | 0 | 0 |
| 126 | 0 | 0 | 1 | 4 | 18 | 1 | 0 | 0 | 0 | 0 | 0 | 0 | 0 | 0 |
| 127 | 0 | 0 | 0 | 3 | 34 | 4 | 1 | 0 | 0 | 0 | 0 | 0 | 0 | 0 |
| 128 | 0 | 0 | 1 | 7 | 60 | 12 | 1 | 0 | 0 | 0 | 0 | 0 | 0 | 0 |
| 129 | 0 | 0 | 2 | 26 | 99 | 38 | 6 | 1 | 0 | 0 | 0 | 0 | 0 | 0 |
| 130 | 0 | 0 | 6 | 53 | 140 | 95 | 18 | 2 | 0 | 0 | 0 | 0 | 0 | 0 |
| 131 | 0 | 0 | 7 | 68 | 152 | 118 | 23 | 2 | 0 | 0 | 0 | 0 | 0 | 0 |
| 132 | 0 | 0 | 4 | 35 | 87 | 63 | 12 | 1 | 0 | 0 | 0 | 0 | 0 | 0 |
| 133 | 0 | 0 | 1 | 10 | 42 | 19 | 3 | 0 | 0 | 0 | 0 | 0 | 0 | 0 |
| 134 | 0 | 0 | 0 | 2 | 24 | 7 | 1 | 0 | 0 | 0 | 0 | 0 | 0 | 0 |
| 135 | 0 | 0 | 0 | 1 | 13 | 4 | 0 | 0 | 0 | 0 | 0 | 0 | 0 | 0 |
| 136 | 0 | 0 | 0 | 1 | 8 | 2 | 0 | 0 | 0 | 0 | 0 | 0 | 0 | 0 |
| 137 | 0 | 0 | 0 | 0 | 3 | 1 | 0 | 0 | 0 | 0 | 0 | 0 | 0 | 0 |
| 138 | 0 | 0 | 0 | 0 | 2 | 1 | 0 | 0 | 0 | 0 | 0 | 0 | 0 | 0 |
| 139 | 0 | 0 | 0 | 0 | 1 | 0 | 0 | 0 | 0 | 0 | 0 | 0 | 0 | 0 |
| 140 | 0 | 0 | 0 | 0 | 1 | 0 | 0 | 0 | 0 | 0 | 0 | 0 | 0 | 0 |
| 141 | 0 | 0 | 0 | 0 | 0 | 0 | 0 | 0 | 0 | 0 | 0 | 0 | 0 | 0 |
| 142 | 0 | 0 | 0 | 0 | 0 | 0 | 0 | 0 | 0 | 0 | 0 | 0 | 0 | 0 |
| 143 | 0 | 0 | 0 | 0 | 0 | 0 | 0 | 0 | 0 | 0 | 0 | 0 | 0 | 0 |
| 144 | 0 | 0 | 0 | 0 | 0 | 0 | 0 | 0 | 0 | 0 | 0 | 0 | 0 | 0 |
| 145 | 0 | 0 | 0 | 0 | 0 | 0 | 0 | 0 | 0 | 0 | 0 | 0 | 0 | 0 |
| 146 | 0 | 0 | 0 | 0 | 0 | 0 | 0 | 0 | 0 | 0 | 0 | 0 | 0 | 0 |
| 147 | 0 | 0 | 0 | 0 | 0 | 0 | 0 | 0 | 0 | 0 | 0 | 0 | 0 | 0 |
| 148 | 0 | 0 | 0 | 0 | 0 | 0 | 0 | 0 | 0 | 0 | 0 | 0 | 0 | 0 |

*FIG. 8*

|     | 132 | 133 | 134 | 135 | 136 | 137 | 138 | 139 | 140 | 141 | 142 | 143 | 144 | 145 |
|-----|-----|-----|-----|-----|-----|-----|-----|-----|-----|-----|-----|-----|-----|-----|
| 118 | 17  | 16  | 16  | 16  | 16  | 16  | 16  | 16  | 17  | 17  | 18  | 18  | 19  | 20  |
| 119 | 15  | 15  | 15  | 15  | 15  | 15  | 15  | 15  | 15  | 16  | 16  | 17  | 18  | 18  |
| 120 | 14  | 14  | 13  | 13  | 13  | 13  | 13  | 14  | 14  | 14  | 15  | 16  | 17  | 17  |
| 121 | 13  | 12  | 12  | 12  | 12  | 12  | 12  | 12  | 13  | 13  | 14  | 15  | 15  | 16  |
| 122 | 12  | 11  | 11  | 11  | 10  | 10  | 11  | 11  | 11  | 12  | 13  | 14  | 14  | 15  |
| 123 | 10  | 10  | 9   | 9   | 9   | 9   | 9   | 10  | 10  | 11  | 12  | 12  | 13  | 14  |
| 124 | 9   | 9   | 8   | 8   | 8   | 8   | 8   | 8   | 9   | 10  | 11  | 11  | 13  | 14  |
| 125 | 8   | 7   | 7   | 6   | 6   | 6   | 7   | 7   | 8   | 9   | 10  | 11  | 12  | 13  |
| 126 | 7   | 6   | 5   | 5   | 5   | 5   | 5   | 6   | 7   | 8   | 9   | 10  | 11  | 12  |
| 127 | 6   | 5   | 4   | 4   | 4   | 4   | 4   | 5   | 6   | 7   | 8   | 9   | 10  | 12  |
| 128 | 5   | 4   | 3   | 2   | 2   | 2   | 3   | 4   | 5   | 6   | 7   | 9   | 10  | 11  |
| 129 | 5   | 3   | 2   | 1   | 1   | 1   | 2   | 3   | 4   | 6   | 7   | 8   | 10  | 11  |
| 130 | 5   | 3   | 2   | 0   | 0   | 0   | 1   | 3   | 4   | 5   | 7   | 8   | 10  | 11  |
| 131 | 5   | 3   | 2   | 0   | 0   | 0   | 1   | 3   | 4   | 5   | 7   | 8   | 10  | 11  |
| 132 | 5   | 3   | 2   | 1   | 1   | 1   | 2   | 3   | 4   | 6   | 7   | 8   | 10  | 11  |
| 133 | 5   | 4   | 3   | 2   | 2   | 2   | 3   | 4   | 5   | 6   | 7   | 9   | 10  | 11  |
| 134 | 6   | 5   | 4   | 4   | 4   | 4   | 4   | 5   | 6   | 7   | 8   | 9   | 10  | 12  |
| 135 | 7   | 6   | 6   | 5   | 5   | 5   | 5   | 6   | 7   | 8   | 9   | 10  | 11  | 12  |
| 136 | 8   | 7   | 7   | 6   | 6   | 6   | 7   | 7   | 8   | 9   | 10  | 11  | 12  | 13  |
| 137 | 9   | 9   | 8   | 8   | 8   | 8   | 8   | 8   | 9   | 10  | 11  | 12  | 13  | 14  |
| 138 | 10  | 10  | 9   | 9   | 9   | 9   | 9   | 10  | 10  | 11  | 12  | 13  | 13  | 15  |
| 139 | 12  | 11  | 11  | 11  | 11  | 11  | 11  | 11  | 11  | 12  | 13  | 14  | 14  | 15  |
| 140 | 13  | 12  | 12  | 12  | 12  | 12  | 12  | 12  | 13  | 13  | 14  | 15  | 16  | 16  |
| 141 | 14  | 14  | 14  | 13  | 13  | 13  | 13  | 14  | 14  | 15  | 15  | 16  | 17  | 17  |
| 142 | 16  | 15  | 15  | 15  | 15  | 15  | 15  | 15  | 15  | 16  | 16  | 17  | 18  | 19  |
| 143 | 17  | 16  | 16  | 16  | 16  | 16  | 16  | 16  | 17  | 17  | 18  | 18  | 19  | 20  |
| 144 | 18  | 18  | 18  | 17  | 17  | 17  | 18  | 18  | 18  | 18  | 19  | 19  | 20  | 21  |
| 145 | 19  | 19  | 19  | 19  | 19  | 19  | 19  | 19  | 19  | 20  | 20  | 21  | 21  | 22  |
| 146 | 21  | 21  | 20  | 20  | 20  | 20  | 20  | 20  | 21  | 21  | 21  | 22  | 23  | 23  |
| 147 | 22  | 22  | 22  | 22  | 22  | 22  | 22  | 22  | 22  | 22  | 23  | 23  | 24  | 24  |
| 148 | 24  | 23  | 23  | 23  | 23  | 23  | 23  | 23  | 23  | 24  | 24  | 25  | 25  | 26  |

*FIG. 9*

|     | 135 | 136 | 137 | 138 | 139 | 140 | 141 | 142 | 143 | 144 | 145 | 146 | 147 | 148 |
|-----|-----|-----|-----|-----|-----|-----|-----|-----|-----|-----|-----|-----|-----|-----|
| 118 | 255 | 255 | 255 | 255 | 255 | 255 | 226 | 255 | 255 | 242 | 255 | 255 | 255 | 128 |
| 119 | 255 | 255 | 255 | 255 | 255 | 255 | 255 | 255 | 255 | 255 | 255 | 255 | 159 | 129 |
| 120 | 255 | 255 | 255 | 255 | 255 | 255 | 255 | 255 | 255 | 255 | 255 | 255 | 194 | 255 |
| 121 | 255 | 255 | 255 | 255 | 255 | 255 | 255 | 255 | 255 | 255 | 255 | 255 | 171 | 194 |
| 122 | 255 | 255 | 255 | 255 | 255 | 255 | 255 | 255 | 255 | 255 | 255 | 255 | 122 | 90  |
| 123 | 255 | 255 | 255 | 255 | 255 | 255 | 255 | 255 | 255 | 255 | 255 | 255 | 244 | 255 |
| 124 | 255 | 255 | 255 | 255 | 255 | 255 | 255 | 255 | 255 | 198 | 174 | 255 | 245 | 255 |
| 125 | 255 | 255 | 255 | 255 | 255 | 255 | 255 | 255 | 255 | 157 | 158 | 255 | 255 | 255 |
| 126 | 255 | 255 | 255 | 255 | 255 | 255 | 255 | 255 | 255 | 255 | 255 | 255 | 234 | 255 |
| 127 | 255 | 255 | 255 | 255 | 255 | 255 | 255 | 255 | 255 | 255 | 255 | 255 | 255 | 255 |
| 128 | 255 | 255 | 255 | 255 | 255 | 255 | 255 | 255 | 255 | 255 | 255 | 255 | 255 | 248 |
| 129 | 255 | 255 | 255 | 255 | 255 | 255 | 255 | 255 | 255 | 255 | 255 | 189 | 255 | 255 |
| 130 | 255 | 255 | 255 | 255 | 255 | 255 | 255 | 255 | 255 | 255 | 255 | 255 | 255 | 255 |
| 131 | 255 | 255 | 255 | 255 | 255 | 255 | 255 | 255 | 255 | 255 | 255 | 255 | 255 | 249 |
| 132 | 255 | 255 | 255 | 255 | 255 | 255 | 255 | 255 | 255 | 255 | 212 | 232 | 255 | 167 |
| 133 | 255 | 255 | 255 | 255 | 255 | 255 | 255 | 255 | 255 | 255 | 153 | 147 | 255 | 172 |
| 134 | 255 | 255 | 255 | 255 | 255 | 255 | 255 | 255 | 255 | 255 | 255 | 193 | 255 | 247 |
| 135 | 255 | 255 | 255 | 255 | 255 | 255 | 255 | 255 | 255 | 192 | 183 | 204 | 255 | 255 |
| 136 | 255 | 255 | 255 | 255 | 255 | 255 | 255 | 255 | 196 | 195 | 195 | 255 | 255 | 255 |
| 137 | 255 | 255 | 255 | 255 | 255 | 255 | 255 | 255 | 255 | 255 | 255 | 255 | 255 | 255 |
| 138 | 255 | 255 | 255 | 255 | 255 | 255 | 255 | 255 | 255 | 255 | 255 | 255 | 255 | 255 |
| 139 | 255 | 255 | 255 | 255 | 255 | 255 | 255 | 255 | 255 | 255 | 250 | 154 | 213 | 255 |
| 140 | 255 | 255 | 255 | 255 | 255 | 255 | 255 | 255 | 255 | 255 | 255 | 162 | 141 | 181 |
| 141 | 255 | 255 | 255 | 255 | 255 | 255 | 255 | 255 | 255 | 255 | 255 | 148 | 132 | 111 |
| 142 | 255 | 255 | 255 | 255 | 255 | 255 | 255 | 255 | 255 | 184 | 255 | 255 | 185 | 113 |
| 143 | 255 | 255 | 255 | 255 | 255 | 255 | 255 | 255 | 216 | 194 | 203 | 255 | 255 | 128 |
| 144 | 255 | 255 | 255 | 255 | 255 | 255 | 255 | 255 | 170 | 175 | 255 | 161 | 255 | 255 |

*FIG. 11*

|  | 212 | 213 | 214 | 215 | 216 | 217 | 218 | 219 | 220 | 221 | 222 | 223 | 224 | 225 |
|---|---|---|---|---|---|---|---|---|---|---|---|---|---|---|
| 170 | 255 | 255 | 255 | 255 | 255 | 224 | 195 | 178 | 176 | 173 | 170 | 149 | 131 | 122 |
| 171 | 255 | 255 | 255 | 255 | 255 | 216 | 203 | 192 | 167 | 155 | 153 | 153 | 154 | 119 |
| 172 | 255 | 255 | 255 | 255 | 255 | 221 | 190 | 170 | 170 | 151 | 133 | 126 | 116 | 103 |
| 173 | 255 | 255 | 240 | 233 | 236 | 227 | 204 | 170 | 145 | 147 | 139 | 132 | 120 | 99 |
| 174 | 255 | 251 | 235 | 215 | 198 | 201 | 189 | 167 | 154 | 140 | 132 | 120 | 117 | 111 |
| 175 | 255 | 247 | 225 | 214 | 213 | 184 | 167 | 150 | 134 | 131 | 120 | 115 | 107 | 104 |
| 176 | 255 | 255 | 218 | 212 | 199 | 169 | 152 | 132 | 123 | 123 | 123 | 110 | 99 | 95 |
| 177 | 255 | 245 | 213 | 183 | 182 | 177 | 153 | 134 | 116 | 110 | 108 | 101 | 90 | 87 |
| 178 | 255 | 247 | 200 | 180 | 158 | 148 | 153 | 141 | 125 | 106 | 97 | 101 | 87 | 80 |
| 179 | 239 | 244 | 222 | 184 | 172 | 156 | 126 | 120 | 115 | 105 | 88 | 88 | 85 | 75 |
| 180 | 213 | 194 | 189 | 183 | 166 | 150 | 137 | 112 | 102 | 100 | 92 | 83 | 81 | 78 |
| 181 | 188 | 179 | 157 | 141 | 140 | 138 | 131 | 118 | 100 | 93 | 92 | 85 | 81 | 77 |
| 182 | 188 | 160 | 159 | 136 | 125 | 125 | 123 | 114 | 101 | 97 | 90 | 83 | 75 | 75 |
| 183 | 185 | 165 | 144 | 133 | 123 | 115 | 114 | 104 | 97 | 96 | 94 | 87 | 74 | 68 |
| 184 | 170 | 151 | 154 | 141 | 118 | 102 | 96 | 97 | 94 | 90 | 81 | 82 | 71 | 63 |
| 185 | 179 | 152 | 129 | 134 | 135 | 110 | 88 | 83 | 86 | 90 | 80 | 77 | 74 | 63 |
| 186 | 150 | 147 | 129 | 119 | 113 | 113 | 100 | 83 | 77 | 79 | 80 | 73 | 67 | 62 |
| 187 | 52 | 121 | 123 | 114 | 107 | 99 | 95 | 91 | 84 | 76 | 70 | 71 | 68 | 58 |
| 188 | 136 | 142 | 126 | 104 | 99 | 94 | 88 | 81 | 80 | 78 | 70 | 66 | 60 | 58 |
| 189 | 128 | 122 | 122 | 117 | 100 | 93 | 88 | 78 | 74 | 73 | 62 | 58 | 56 | 50 |
| 190 | 118 | 109 | 107 | 106 | 98 | 92 | 88 | 81 | 72 | 65 | 58 | 52 | 50 | 50 |
| 191 | 111 | 99 | 97 | 91 | 91 | 82 | 83 | 81 | 72 | 65 | 57 | 50 | 48 | 46 |
| 192 | 108 | 101 | 87 | 84 | 83 | 76 | 74 | 71 | 69 | 62 | 58 | 56 | 47 | 46 |
| 193 | 98 | 93 | 86 | 77 | 78 | 72 | 72 | 66 | 60 | 60 | 54 | 51 | 48 | 45 |
| 194 | 96 | 83 | 82 | 80 | 76 | 72 | 65 | 64 | 59 | 59 | 53 | 47 | 46 | 47 |
| 195 | 94 | 88 | 79 | 73 | 75 | 72 | 64 | 60 | 56 | 52 | 50 | 53 | 46 | 46 |
| 196 | 99 | 84 | 79 | 70 | 68 | 69 | 66 | 59 | 54 | 53 | 43 | 47 | 49 | 43 |

*FIG. 14*

| | 1270 | 1271 | 1272 | 1273 | 1274 | 1275 | 1276 | 1277 | 1278 | 1279 | 1280 | 1281 | 1282 | 1283 |
|---|---|---|---|---|---|---|---|---|---|---|---|---|---|---|
| 118 | 5 | 5 | 5 | 5 | 5 | 5 | 5 | 5 | 5 | 5 | 4 | 5 | 1 | 1 |
| 119 | 5 | 5 | 5 | 5 | 5 | 5 | 4 | 5 | 4 | 5 | 5 | 6 | 1 | 1 |
| 120 | 5 | 5 | 6 | 5 | 4 | 5 | 4 | 5 | 5 | 5 | 5 | 5 | 1 | 1 |
| 121 | 5 | 5 | 5 | 5 | 5 | 6 | 4 | 5 | 5 | 5 | 5 | 4 | 1 | 1 |
| 122 | 5 | 5 | 5 | 5 | 5 | 5 | 5 | 5 | 4 | 5 | 5 | 5 | 1 | 1 |
| 123 | 5 | 5 | 5 | 5 | 5 | 4 | 5 | 4 | 5 | 5 | 4 | 4 | 1 | 1 |
| 124 | 5 | 5 | 4 | 5 | 5 | 5 | 5 | 5 | 6 | 5 | 4 | 4 | 1 | 1 |
| 125 | 5 | 5 | 4 | 5 | 5 | 5 | 4 | 4 | 6 | 5 | 5 | 4 | 2 | 1 |
| 126 | 5 | 5 | 5 | 4 | 4 | 5 | 5 | 4 | 5 | 5 | 5 | 5 | 1 | 1 |
| 127 | 5 | 5 | 4 | 5 | 5 | 5 | 5 | 5 | 5 | 5 | 5 | 5 | 1 | 1 |
| 128 | 5 | 5 | 5 | 4 | 5 | 5 | 5 | 5 | 5 | 5 | 5 | 5 | 1 | 1 |
| 129 | 5 | 5 | 5 | 5 | 5 | 5 | 5 | 5 | 5 | 5 | 5 | 5 | 1 | 0 |
| 130 | 7 | 5 | 5 | 5 | 4 | 6 | 5 | 5 | 4 | 5 | 5 | 5 | 2 | 1 |
| 131 | 4 | 5 | 4 | 5 | 5 | 6 | 6 | 5 | 5 | 5 | 5 | 5 | 1 | 1 |
| 132 | 5 | 5 | 5 | 5 | 5 | 6 | 5 | 4 | 5 | 5 | 5 | 6 | 1 | 1 |
| 133 | 5 | 5 | 5 | 5 | 5 | 4 | 5 | 4 | 5 | 5 | 5 | 5 | 1 | 1 |
| 134 | 5 | 5 | 5 | 5 | 5 | 5 | 5 | 4 | 5 | 5 | 4 | 4 | 1 | 1 |
| 135 | 5 | 5 | 5 | 4 | 4 | 5 | 5 | 5 | 4 | 5 | 5 | 4 | 2 | 1 |
| 136 | 5 | 5 | 4 | 5 | 5 | 4 | 4 | 5 | 4 | 4 | 4 | 5 | 1 | 1 |
| 137 | 5 | 5 | 6 | 4 | 5 | 5 | 4 | 5 | 5 | 5 | 4 | 4 | 1 | 0 |
| 138 | 5 | 5 | 5 | 5 | 5 | 5 | 5 | 5 | 5 | 5 | 5 | 5 | 1 | 1 |
| 139 | 5 | 5 | 5 | 5 | 5 | 5 | 5 | 5 | 4 | 4 | 5 | 5 | 2 | 1 |
| 140 | 5 | 4 | 5 | 5 | 5 | 4 | 5 | 5 | 5 | 5 | 4 | 5 | 2 | 1 |
| 141 | 5 | 4 | 5 | 5 | 5 | 4 | 5 | 5 | 4 | 4 | 4 | 5 | 1 | 1 |
| 142 | 5 | 5 | 4 | 5 | 5 | 5 | 5 | 5 | 4 | 5 | 5 | 5 | 1 | 1 |
| 143 | 5 | 5 | 5 | 5 | 4 | 5 | 5 | 5 | 4 | 5 | 4 | 4 | 1 | 1 |
| 144 | 5 | 5 | 5 | 5 | 5 | 5 | 5 | 5 | 5 | 5 | 5 | 4 | 1 | 1 |
| 145 | 4 | 5 | 5 | 5 | 4 | 5 | 5 | 4 | 6 | 5 | 5 | 5 | 1 | 1 |
| 146 | 6 | 5 | 5 | 5 | 5 | 5 | 4 | 5 | 5 | 5 | 5 | 5 | 1 | 1 |
| 147 | 5 | 4 | 5 | 5 | 5 | 5 | 4 | 5 | 5 | 5 | 5 | 4 | 1 | 2 |
| 148 | 5 | 5 | 4 | 4 | 5 | 4 | 4 | 5 | 4 | 4 | 5 | 5 | 2 | 0 |

FIG. 17

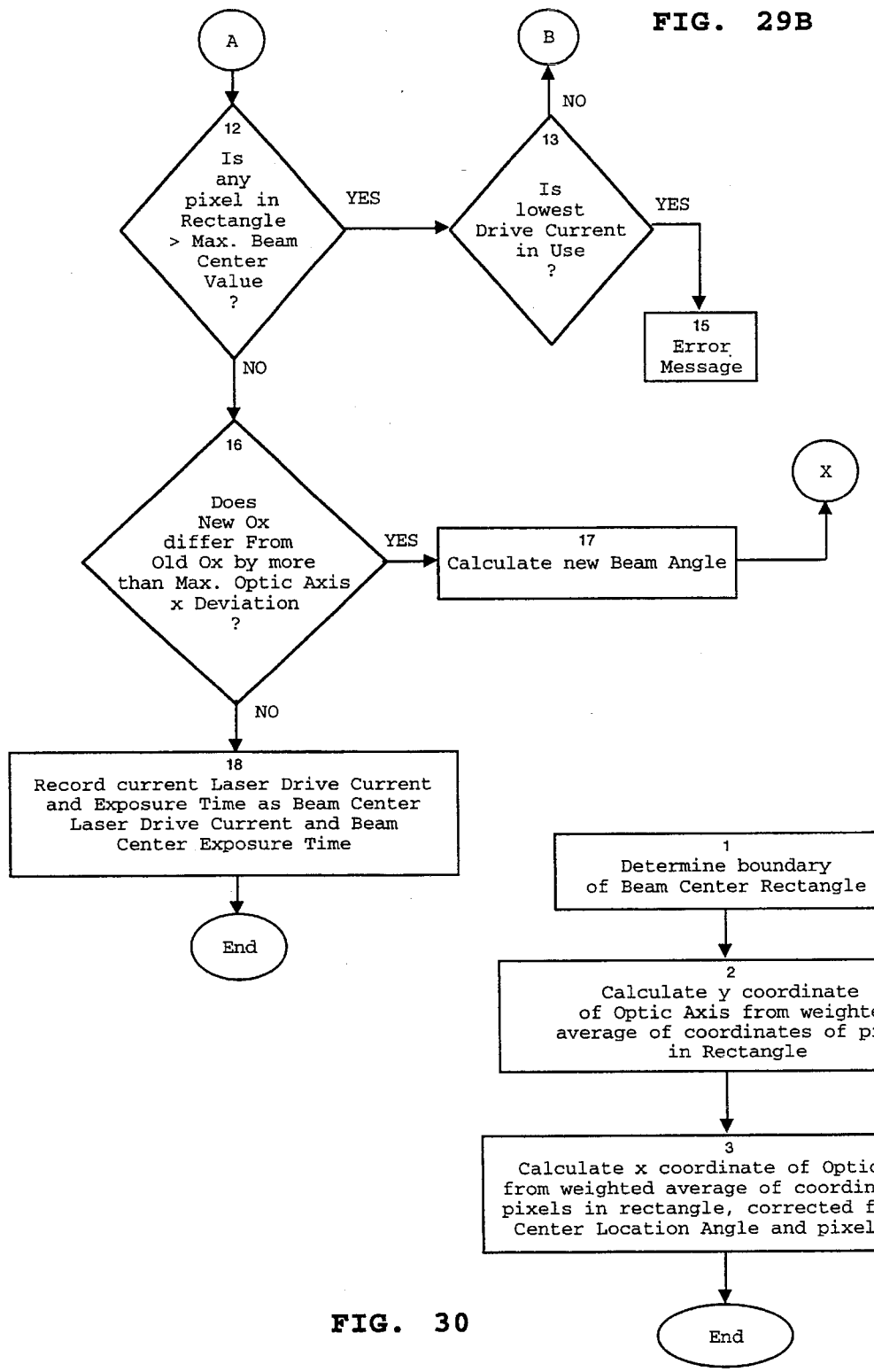

APPARATUS AND METHOD FOR DETERMINING THE SIZE DISTRIBUTION OF PARTICLES BY LIGHT SCATTERING

FIELD OF THE INVENTION

This invention relates in general to light scattering instrumentation and more particularly to instruments and methods for determining the size distribution of particles by light scattering.

BACKGROUND OF THE INVENTION

Light traveling in a homogeneous medium travels in straight lines. However, when light travels through a medium containing particles of material, the particles scatter the light. For a single particle, the amount of scattering in a particular direction depends upon the size, shape, and composition of the particle and the wavelength of the light. For a collection of particles, light scattered from all of the particles contributes to the total intensity of light scattered in a particular direction relative to the incident light. By measuring the amount or intensity of light scattered throughout a number of angles relative to the incident light, it is possible to infer properties of the particles that induce the scattering. In particular, for particles of small size and similar composition, the pattern of scattered light is indicative of the sizes of the scattering particles. Prior analytical instruments have used the technique of analyzing the scattered light intensity to determine the spectrum of particle sizes for a mixture of small particles of varying sizes. A particle size analyzer using this technique typically samples the angular distribution of the intensity of the light scattered from the mixture, processes the data, and produces numerical values and possibly a graph or a histogram as output. The analyzer output represents the number or volume fraction of scattering particles in the mixture as a function of the size of the particles and is usually called a particle size distribution.

The prior an has provided many different techniques of measuring and analyzing the light scattered by small particles. For example, a technique called optical particle counting has been developed for separately detecting the light scattered by individual particles in extremely dilute concentrations of particles, but this technique is time consuming and is impractical for samples containing a large number of particles. On the other hand, if the concentration of particles is too great, light scatters multiple times from the scattering particles before being observed, and the multiple scatterings obscure the effect of each particle's contribution to the observed intensity of scattered light. Particle size analyzers have therefore primarily addressed the experimental conditions where the concentration of scattering particles is such that each observed light ray is deflected only once by a single scattering particle. Under these conditions, called single scattering, the scattered light has been analyzed either by measuring the time variation of the light scattered in a particular direction or by time averaging the scattered light over a range of directions. The former technique is called dynamic light scattering, and the latter is termed static, or classical, light scattering.

For classical scattering, the problem of relating the angular distribution of scattered light to the size of the scattering particle has been solved mathematically for the case of a spherical particle illuminated by a beam of unpolarized light. The mathematical solution is given by a theory proposed by Gustav Mie. The Mie theory is set forth in Chapter 4 of the book, *Absorption and Scattering of Light by Small Particles,* by Craig F. Bohren and Donald R. Huffman (John Wiley & Sons, 1983), which book is incorporated by reference. A particle size analyzer may employ the Mie theory to determine particle size distributions from the observed pattern of scattered light. Such an analyzer is not limited to the analysis of only samples containing particles of spherical shape; the sizes are reported as radii of spheres that are equivalent to the actual particles in terms of light scattering. For most applications, the equivalent-sphere specification of a particle size distribution is sufficient to characterize the actual particle size distribution. Mathematical models have also been derived for particular particle shapes other than spherical, but they have been found to have limited value since, for scattering, only the average behavior of a large number of particles is of interest.

Since scattering is also a function of the wavelength of the incident light, prior an analyzers have found it convenient to use incident light of a single wavelength. For this purpose, a laser has been the typical source. Lasers have been used which produce light in the visible and near-visible wavelength range. The descriptions herein of the prior art, and of the invention, use the term "light," but it must be recognized that the scattering being described is a phenomenon of electromagnetic radiation in general. Thus, the term "light" herein should be read as referring to any such radiation that meets whatever constraints are imposed by the characteristics of the various components of the analyzer (such as the transparency of the sample holders at the wavelength of interest and the frequency response of the detectors), the nature of the scattering particles (such as the refractive index and absorption coefficient as a function of wavelength), and the overall construction of the analyzer.

In a typical prior art arrangement, a particle size analyzer has a source of unpolarized light that is projected in a beam to impinge upon a sample. The sample contains the particles whose sizes are under investigation. The particles are dispersed in the region of the sample that is illuminated by the incident light beam. The particles scatter light in patterns that are dependent on the ratio of the size of the particle to the wavelength of the light, and on the refractive index of the particle material. The refractive index, a complex function of wavelength, is a measure of how much the light is refracted, reflected, and absorbed by the material. For a beam of unpolarized light incident on a random mixture of small particles, the scattering pattern is symmetric about the axis of the incident beam. The scattering is the result of the refraction, reflection, and absorption by the particles, as well as diffraction at each particle surface where a light ray in the incident beam is tangent to the particle surface.

Light that scatters at a particular angle with respect to the incident beam may be rotated about the beam axis without changing the scattering angle. A large number of rays scattering from a single particle at a given scattering angle will fill all rotational orientations and thus form a cone of light, with the apex at the scattering particle and with the generating angle (one-half the apex angle) of the cone equal to the scattering angle. The pattern of light rays scattering at all angles from a single particle may thus be thought of as made up of a continuous series of open cones of light, with the generating angle for a given cone corresponding to the scattering angle for the light comprising the surface of that cone. The axes of all of the cones are collinear with the line defined by the incident beam, and the apexes of the cones are located at the scattering particle. At a distance from the scattering particle, a plane perpendicular to the incident beam will intersect a given cone in a circle. Planes not perpendicular to the incident beam will intersect a given cone in a curved line comprising a conic section, .i.e., an ellipse, a parabola, or a hyperbola, depending upon the orientation of the plane. Regardless of form, the curved line of intersection represents a single scattering angle.

In any practical particle size detector, it is not possible or necessary to measure the scattering angle with infinite precision. Nevertheless, better angular resolution in the analyzer provides better particle size resolution. In order to address angular precision effects directly, we will refer to the set of all scattering angles falling between a precise lower angular limit and a precise upper angular limit as an "angle class" of some intermediate angle q. Light scattered within an angle class scatters into the region between two cones of slightly different size. The smaller (inner) of the two cones is generated by the lower angular limit of the angle class and the larger (outer) cone is generated by the upper angular limit. The apexes of both cones are located at the scattering particle.

The inner and outer cones of an angle class define a circular annular region on a plane perpendicular to the incident beam and a more complex shaped region (corresponding to a conic section) on a plane not perpendicular to the incident beam. Scattered light rays intersecting the interior of such a region are rays which have scattered through an angle between the two generating angles of the cones. Thus any light ray intersecting such a region belongs to the angle class defined by that region. Prior analyzers have employed ring-shaped light detectors to measure the amount of light that scatters in an angle class determined by the radius and width of the ring and its distance from the scattering region. To correlate correctly the detected light with a scattering angle, these ring-shaped detectors must be mounted and aligned precisely perpendicular to the incident beam.

Since the interaction region of the incident beam with the particles generally has a finite extent, multiple particles at different locations in the incident beam will each contribute multiple overlapping cones of scattered light, with the apexes of the cones offset by the distance between the particles. Particles of the same size will have overlapping scattered-light cones of similar intensity variations, whereas particles of different sizes will have overlapping scattered-light cones of different intensity variations.

When the light beam illuminates a sample volume of finite extent, a converging lens may be used to direct parallel rays of light, each by definition scattered through the same scattering angle (by different particles), to a single point on a light detector in the focal plane of the lens. A lens that functions in this manner performs a Fourier transform, so that all light arriving at a given point on the detector is known to have been scattered by the sample through a particular scattering angle, regardless of the location of the scattering particle in the sample volume.

The effect of the converging lens is to transform the spatial distribution of the scattered light it receives to that of an equivalent virtual system in which the light distribution in the focal plane of the lens is the same as if all the scattering particles were located at a point coincident with the optic center of the lens. The light detectors are placed in the focal plane of the lens. The line from the optic center of the lens to the focal point of the lens is usually called the optic axis.

If a scattered ray passes through different refracting media, such as air and a sample suspension fluid, before detection, then an appropriate correction must be applied to the ray's apparent angle of scatter to determine its true angle of scatter. Use of a lens and recognition of the virtual scattering system simplifies the correction.

The intensity of light scattered as a function of scattering angle, when experimentally determined as above for a sample composed of many particles of a range of different sizes, consists of the summation of the scattered light from all the particles. If we assume that each size particle in the sample scatters light according to a given mathematical theory and in proportion the relative number of such size particles present, then it is mathematically possible to determine from the experimental data the relative numbers of each size particle constituting the sample, i.e., to determine the size distribution of the sample. The well-known mathematical process by which the size distribution may extracted from the composite data is called an inversion process, or sometimes a deconvolution process.

In the usual convention, a scattering angle of zero degrees coincides with unscattered light, and a scattering angle of 180 degrees represents light reflecting directly back into the incident beam. Scattering angles between 90 and 180 degrees are termed backscattering.

Light scattering particle size analyzers are typically employed for particles ranging in size from less than one micrometer to several hundred micrometers. Within this size range, and for light in the visible or near-visible portion of the spectrum, the smaller particles tend to scatter light somewhat uniformly in all directions, whereas the larger particles scatter light mostly in the forward direction (small angle with respect to the incident beam direction). However, the larger particles also scatter much more light than the smaller particles. Thus particles of all sizes will contribute to the amount of light scattered in a particular direction. To extract particle size information accurately from measurements of scattered light intensity, a particle size analyzer usually measures the intensity of light scattered at a number of angles relative to the incident beam.

It is important, especially in the forward direction, that a particle size analyzer provide high angular resolution of the light intensity data. It is characteristic of the mathematical inversion process that the number of distinct particle sizes postulated to exist in the sample cannot exceed the number of angular positions for which scattering intensity data values are measured. Therefore, high angular resolution, allowing independent scattering intensity data to be obtained at many closely spaced angles, will enable an analyzer to distinguish the quantity of particles at more closely spaced particle sizes and will lead to more precision and higher resolution in the particle size distribution obtained by the inversion process. A good discussion of the desirability of obtaining high resolution in particle scattering data is contained in the Coulter Corporation Technical Monograph, "LS Series Resolution," which monograph is incorporated by reference.

The problem of achieving an accurate characterization of a given particle distribution may be illustrated with a specific example. Assume that scattering intensity data are obtained for n scattering classes $q_i$ and are represented by the scattering intensity function $I(q_i)$, with i=1 . . . , n. A particular mathematical model, such as (but not limited to) the Mie theory, is chosen to represent the light scattering by the particles in each class. Computations with the theory predict $s_{ij}$ as the amount of scattering in angle class i for a particle of size j, with j=1 . . . , m. The particle size parameter j represents m particle sizes ranging from 0.1 micrometers to 1000 micrometers. Typically j will represent equally-spaced intervals on a log-based size scale. The particle size distribution $S_j$ is related to the intensity $I(q_i)$ through the matrix equation $$[I(q_i)]=[s_{ij}][S_j].$$

Thus, $S_j$ may be determined through inversion $$[S_j]=[s_{ij}]^{-1}[s_{ij}][S_j]=[s_{ij}]^{-1}[I(q_i)]$$

Since the fortieth root of ten is 1.05925, 40 equally-spaced log intervals per size decade must be employed in the computation of $[s_{ij}]$ to achieve a resolution of 6% in the particle size distribution. To achieve this size resolution through four decades (particle sizes ranging from 0.1 micrometers to 1000 micrometers), $[s_{ij}]$ must have 160 elements in the j dimension. This implies that the analyzer must employ at least 160 angle classes, and preferably at least 320 classes, to ensure a well-behaved inversion. For an analyzer that operates in the scattering angle range of 0° to 32°, 320 angle classes implies an angular resolution of 0.1° if all of the angle classes are equally spaced.

Many prior art devices have addressed the need of a particle size analyzer to achieve high angular resolution and to respond to a wide range of scattered light intensities. For example, U.S. Pat. Nos. 4,953,978, 5,056,918; and 5,104,221, issued to Bott, disclose a plurality of discrete annular silicon photodetector sectors, of circular shape and increasing radius, disposed in a fixed position relative to the nominal beam axis. These detectors are responsive to the cone of scattered light that intersects the detector in a region defined by the circular shape of the detector. Additional silicon photodetectors can be deployed in a line extending beyond the annular detectors, extending the angular range of the analyzer. The intent in these patents is that each of the discrete photodetectors is selected and mounted to be responsive to light scattered in a fixed angular interval with respect to the nominal beam axis. In this manner, the geometrical shape of the photodetector and its intensity response can be configured so that the sensitivity and dynamic characteristics of the detector match the light intensity expected for the angular position of the photodetector. Similar design considerations have been employed by prior art analyzers that employ fixed deployments of ring-shaped photodetectors.

However, the use of fixed deployments of discrete solid-state photodetectors leads to many problems. For example, these deployments require precise calibration and alignment with the light source in order to obtain valid light scattering data. The calibration and alignment must be re-done at any time that a component of the analyzer is moved or changed. Another problem encountered with the use of fixed deployments of discrete photodetectors is that the number and complexity of detectors used increases the cost of the analyzer and increases the chance for malfunction. Solid-state photodetectors provide a current signal which is proportional to the light intensity falling on the photodetector. Thus, great care must be used in measuring the low current resulting from low intensity light.

The most significant problem with prior art analyzers using fixed deployments of discrete photodetectors is the limited number of detector elements used. These analyzers typically employ 16 to 32 detector elements, although some may use as many as 126 elements. In any case, the number used directly limits the resolution (number of unknown independent variables) obtainable in the size distribution. An approximation used by prior devices to overcome this limitation is to assume that a particular functional form, such as a Gaussian distribution, can be used to describe the particle size distribution of a sample. In this way, the number of unknown independent variables is reduced to the two parameters necessary to define the Gaussian curve. Unfortunately, most samples are poorly described by a Gaussian curve, and the validity of such a result is problematic at best. Sometimes size resolution is enhanced by limiting the analyzer to a narrow range of particle sizes, but this technique limits the general utility of the analyzer to determine particle size distributions across a broad variety of sizes.

Other prior art devices use photomultipliers as the light detector, such as described in U.S. Pat. Nos. 4,676,641 and 4,781,460, issued to Bott. Multiple photomultipliers can be used at different angles to the incident beam, or a single photomultiplier can be used and moved through an angle relative to the incident beam to collect data at different scattering angles. The physical size of a photomultiplier (in general, larger that a discrete silicon photodetector) causes problems since a high angular resolution cannot be achieved without masking off a portion of the light entrance window. The masking limits the light entering the photomultiplier and thereby lengthens the exposure time required to obtain sufficient data. In addition, the size of a photomultiplier prohibits the side-by-side mounting of multiple photomultipliers to cover adjacent angle classes. It is therefore necessary to move the photomultiplier to many angular positions to get data, further lengthening the data acquisition time and adding to the complexity of the analyzer. During long data acquisition runs, the particle size characteristics of the sample may change, creating problems for accurate data analysis. Like silicon photodetectors, photomultipliers provide a current signal which is proportional to the light intensity falling on the photomultiplier. Thus, where the intensity is low, the current is low and care must be exercised in reading the current.

A problem common to all of the prior art particle size analyzers is that they must be mechanically or manually aligned. Frequently, the alignment procedure must be performed between data acquisition runs for different samples. Thus prior art analyzers require operator monitoring and intervention on a regular basis, making unattended or automatic operation problematic.

Another problem common to all of prior art analyzers is that their angular resolution is controlled by varying the detector size, by masking of the detector, or by changing other mechanical or opto-mechanical aspects of the devices, generally in the design stage. These techniques of controlling angular resolution imply that the analyzer is not easily re-configured to change the resolution which may be desired for particular experimental needs. Prior art analyzers tend to be configured by the manufacturer for an assumed amount of angular resolution at the various scattering angles provided by the analyzer and no variation is possible.

Prior art analyzers have had particular problems when analyzing particle samples that consist of two or more groups of distinct but nearly identical sizes. This situation causes difficulties in the inversion process unless a very high angular resolution of the scattering data is available. Where sufficiently high resolution is not available, the inversion analysis must be constrained to look for assumed functional fits (i.e., Gaussian, bi-modal or multi-modal Gaussian, etc.) to the experimental data with theoretical size values close to the size values to be determined. The lack of sufficient angular resolution in prior art analyzers has led to the necessity of operator input, in the form of an educated guess as to the make-up of the particle mix or selection of functional constraints, to resolve the two or more groups of particles in the particle size distribution.

Thus, a need exists for a particle size analyzer capable of resolving several hundred angle classes which can be used in varying analytical conditions without physical realignment of the analyzer or guidance from the operator as to the nature of the particle mix under investigation, and which, when compared to the prior art, produces both scattering intensity data over a larger angular range with greatly increased angular resolution and particle size distributions over a larger range of particle sizes with greatly increased size resolution.

SUMMARY OF THE INVENTION

The present invention solves the problems of the prior art described above. Furthermore, the present invention achieves a precision and resolving power in particle size distributions that is unavailable using prior art devices. These advances are achieved by using a light detector comprising a two-dimensional array of small photosensitive elements, called pixels. Generally described, the invention provides a method and apparatus for obtaining particle size data for a group of dispersed particles, according to which the particles are illuminated with a dose of light in a collimated beam from a light source so as to scatter light of the beam, and at least a portion of the light interacting with the particles is detected with a two-dimensional array of functionally equivalent photosensitive pixels. The functionally equivalent aspect of the pixels allows the analyzer to dynamically configure and re-configure at least a portion of the pixels into a variable number of data collection areas. The nature of the pixel array makes it possible for output data from the pixels to be received by a processor configured to determine from the output data the location at which an unscattered center of the beam intersects the array. Thus, no precision mechanical alignment of the light source and the detector is required prior to operation of the analyzer. Furthermore, the ability of the analyzer to determine the unscattered beam center allows the analyzer to classify each of at least a portion of the pixels to data collection areas according to a function of the geometric relationship that the pixel bears to the beam center.

The pixels are functionally equivalent in the sense that each pixel is equally suitable for measuring the intensity of light scattered in any direction by the dispersed particles. Each of the pixels preferably is capable of individually and independently providing a measure of the light falling on it. The pixels preferably are not discrete components, but are manufactured as an integrated electrical device. Preferably, the pixels are deployed such that the pixel array forms a surface and such that the location of the pixel can be inferred from its identity.

The pixels can be of varying sizes. The pixels preferably are densely arranged, meaning that the pixels are of small size and the pixel spacing is not significantly larger than the pixel size. Commercially available densely arranged pixel arrays have pixel spacings from about 0.007 mm to 0.060 mm in planar arrays, and the photosensitive area of the pixel array is more than two-thirds of the smallest contiguous area containing the pixels. For high resolution and rapid measurement time, the pixel size is preferably small, on the order of 0.02 mm square, and the number of pixels is preferably large, on the order of an array of 1,000 by 1,000 or larger, with the pixel spacing being not much larger than the pixel size. Thus, instead of 126 or fewer independent angular measurements of scattered light intensity, as in the best prior art instruments, implementations of the invention can provide as many as a million or more independent measurements.

The manufacturer of a prior art particle size analyzer which employs 126 light detectors has published literature containing the statement that this analyzer uses "the theoretical maximum number of detectors (126)." Thus, in contradiction to the teachings of the prior art, the present invention has greatly exceeded the "theoretical maximum".

Since each pixel's electric output signal (also called output data) can be read separately, extremely good geometric resolution can be achieved. By mounting the array at an appropriate distance from the scattering particles and by the preferred use of a lens or lenses, the array's superior geometric resolution translates into superior angular resolution. To control the reading, storing and processing of the large amount of scattering data produced by the invention, electronic processing is used.

The two-dimensional array of photosensitive elements may be of several types. One type is a charged-coupled device ("CCD"). A CCD is an array of photosensitive pixels, preferably in perpendicular rows and columns, each of which converts incident light into an electric charge proportional to the total amount of light falling on the pixel since the last reset command provided to the CCD. The electric charge is made available as an output signal of the CCD on a row or column basis when a read command is given to the CCD. The readout of a CCD normally drains each pixel of its charge and is, in that case, a destructive readout.

CCD's have been extensively used, e.g., in video cameras, where their geometric resolution provides a good imaging capability. Others have suggested the use of a CCD as the light detector in a particle size analyzer. However, CCD's do not have a wide dynamic range; typically, they are capable of measuring light intensity only in a range of 256 or 4,096 to 1. A particle size analyzer must be capable of handling light intensity variations spanning eight orders of magnitude. Furthermore, CCD's have particular electronic responses, such as "blooming", discussed below, which are not present in the detectors used in the prior art. These factors mitigate against simply substituting a CCD unit for the light detectors in the prior art devices.

Another type of array suitable for use in the invention is a charge injection device ("CID"). A CID is a device similar to a CCD, but its pixel structure and array architecture permit selective readout of a subsection of the pixel array. A CID also provides non-destructive readout and pixel charge control, which facilitates control of the blooming phenomenon exhibited by CCD's.

Other pixel structures and array architectures have been reported in the literature, including a Charge Modulated Device ("CMD"). The CMD is an MOS image sensor, preferably with a rectangular grid of pixels, where each pixel is a light sensitive MOS transistor characterized by a high optical gain and a non-destructive readout operation. CMD's are described in the article *A New MOS Phototransistor Operating in a Non-Destructive Readout Mode*, Japanese Journal of Applied Physics, Vol. 24 (1985), pp. L323–L325, and a later article by Nakamura et al., *A New MOS Image Sensor Operating in a Non-Destructive Readout Mode*, IDEM Vol 86, pp. 353–356, which articles are incorporated by reference. The CMD is an example of an active-pixel sensor ("APS"), where each pixel's output is individually amplified or buffered. Other APS devices include a Bulk Charge Modulated Device ("BCMD"), with a hexagonal packing format; APS devices with static induction transistors; and a Base Stored Image Sensor, as reported in the article *Active-Pixel Sensors Challenge CCDs,* Laser Focus World, June 1993, which article is incorporated by reference. Hybrid infrared image sensors are photosensitive pixel arrays that are commercially available. All of these devices are suitable for use in the invention.

Yet another type of a photosensitive pixel array is an integrated array of silicon photodetectors. These arrays may contain configurations of 128×128 pixels or 256×256 pixels with a 0.06 mm center-to-center pixel spacing in both the horizontal and vertical directions. The electronic circuitry associated with these devises preferably integrates the photodetector current for each pixel. In this case, each pixel's output is an electric charge proportional to the total amount of light falling on the pixel since the last reset command, as in a CCD.

For simplicity in the specification and claims below, the term "pixel array" will be used herein to refer to any device whose structure includes a two-dimensional array of small, closely arranged photosensitive elements configured as an integrated electrical device and which provides an electric signal responsive to the light falling on the photosensitive elements. Other than the invention described and claimed herein, the inventors are unaware of any successful attempt to design or build a light scattering particle size analyzer using a pixel array, as broadly defined herein.

The present invention, however, has solved the problem of using a pixel array in a particle size analyzer to measure the scattered light intensity. In the preferred embodiment, a single CCD is used to measure the scattered light intensity throughout all angular regions of interest. The invention compensates for the CCD's low dynamic range by employing a number of novel techniques. The techniques fall into two categories: recognizing and ignoring those pixels whose dynamic range is exceeded, and controlling the intensity and duration of the light source to ensure that the entire angular range of interest is measured. The net effect of these techniques is to extend the dynamic range of the CCD to that required by a particle size analyzer.

One technique employed by the preferred embodiment of the present invention to extend the dynamic range of the CCD uses the fact that each pixel of a CCD measures the time integral of the light intensity falling on it. Thus, extremely high intensity light can be effectively measured if the CCD is exposed to the light for only an extremely short period of time. Conversely, very low levels of light intensity can be measured by exposing the CCD for a longer period of time. The exposure time of the CCD is controlled by switching the light source on and off or by deflecting or stopping the light source beam before it strikes the sample, effectively creating light pulses of varying duration. Typically the analyzer uses shorter exposure times for scattering data taken at forward angles and longer exposure times for scattering data taken at larger angles. Generally, in producing a single particle size distribution, multiple exposures of varying times are utilized in obtaining scattering intensity data which span a wide range of intensity values. Therefore, for effective analysis where there are differing exposure times, the CCD output signals for the differing times must be normalized, or scaled, to an exposure time standard. The invention recognizes the effect of different exposure times and provides the correct normalizing factors for adjusting the CCD output data.

Another technique used by the preferred embodiment of the invention to ensure that the dynamic range of the CCD is not exceeded also uses the intensity-integrating characteristic of the CCD. The invention directly controls the intensity of the light source so as to reduce or increase the amount of scattered light falling on the CCD, as desired. The combination of controlling both the intensity of the light source and the time of the exposure leads to the concept of a light "dose", which is the product of the intensity of the light source and the time that the light source is on. By controlling the light dose, the invention can ensure that the amount of light scattered at a particular angle or region on the CCD is within the CCD's dynamic measurement range. The invention also uses the amount of the light dose for an exposure to determine automatically the correct factors to normalize, or to scale, the measurements of scattered light taken during different exposures.

Another technique to keep within the dynamic range of the CCD used in the preferred embodiment of the invention is to control the number of scattering particles, placing more particles in the incident beam to increase the intensity of scattered light and placing fewer particles in the beam for less intensity. This may be accomplished by using sample cells to hold the scattering particles. Preferably, the particles are dispersed in a fluid, such as water which is contained in the sample cell. The number of scattering particles in the incident beam can be varied by varying the concentration of the particles in the fluid or by changing the angle of the scattering cell relative to the incident beam. Alternatively, the number of particles can be varied by using sample cells of differing widths measured in a direction along the beam. The invention determines the correct normalizing factors to adjust the CCD output signals for multiple exposures using differing numbers of scattering particles in the incident beam. No realignment of the analyzer is required.

If the dynamic range of any pixels in the CCD is exceeded, the phenomenon known as "blooming" can occur. Blooming occurs after a pixel becomes saturated with charge and its charge begins to "bleed", or discharge, into adjacent pixels. This phenomenon affects the ability of a CCD detector to be used successfully in a light scattering particle size analyzer. Blooming is a particular problem at small scattering angles, where very high light intensity gradients can cause some pixels to be oversaturated before other nearby pixels register any measurable intensity. Blooming in such situations obscures important scattering patterns which occur at small angles. Certain commercially available CCD's, such as the Kodak KAF-1300L, incorporate anti-blooming protection which keeps each pixel from discharging into adjacent pixels for a limited rate of overcharging of the pixel. However, anti-blooming protection cannot protect against all blooming that would occur in a particle size analyzer. Therefore, the invention includes additional methods of addressing the blooming phenomena.

With the ability to control and adjust, or normalize, for differing beam intensities and exposure times, and with the ability to process individually each pixel of scattered light intensity data, it becomes possible to use a single pixel array, even one with a fairly low dynamic range such as a CCD, for all angular regions of interest. In the preferred embodiment, the use of a single pixel array minimizes the expense of manufacturing the particle size analyzer. When a single pixel array is used, it is preferable to provide for changing the relative angle between the pixel array and the incident beam so that scattering intensity data can be obtained over a wide range of scattering angles. This is accomplished by providing a movable pixel array for moving through an angle relative to the incident beam, or, preferably, by providing a movable light source for moving through an angle relative to the optic axis.

Since in the preferred embodiment of the present invention the incident beam and the pixel array are not in a fixed orientation with respect to each other, provision is made to automatically locate the relative position of the pixel array. As a first provision, the invention automatically senses when the beam impinges directly on the pixel array and determines the location on the pixel array of the beam center. When the light beam does not fall on the pixel array, a second provision is made to locate automatically the position of the pixel array. The movements of the light source or of the pixel array from or until the time the beam strikes the pixel array are recorded and are used to determine the relative angle between the light beam and the optic axis. In this manner, the light scattered through the entire range of scattering angles, from 0° to 180°, can be measured with the present invention. The determination of the location of beam center is very accurate, reproducibly locating beam center to within one pixel on the pixel array. The desirability of reproducibility in a particle size analyzer is discussed in the Coulter Corporation Technical Monograph, "LS Series Reproducibility," which monograph is incorporated by reference.

An important feature of the present invention is a provision to divide the pixels of the pixel array into a number of data collection areas. One type of data collection area, called an angle class herein, is configured so as to have angular significance. This is desirable because the pixel array preferably employed subtends a fairly large angle at the optic center of the lens, typically on the order of five or six degrees. Assigning the pixels to angle classes is performed under the control of the invention. The configuration of data collection areas is readily changed during the operation of the analyzer. Therefore, the assignment of pixels to angle classes can be multiply re-done to accommodate the different geometric shapes taken by the intersection of the cone of scattered light with the surface of the pixel array when the pixel array has different positions relative to the incident light beam. The division of the pixels into variable angle classes also permits the analyzer to achieve different angular resolutions at different stages of the analysis or at different scattering angles. This means that the analyzer can decrease the angular resolution, where the resolution is not a critical factor, to shorten the analysis run time. The analyzer can also increase the angular resolution when resolution is important. The number and range of angular values represented by the angle classes is variable to accommodate varying angular resolution requirements. In setting up the angle classes, the present invention uses angular intervals varying from 0.0025 degrees for very small angles (less than 0.1 degree) to 0.1 degrees for large angles (greater than 3.2 degrees).

The assignment of pixels to angle classes is carried out by use of well-known trigonometric relationships. Each pixel is assigned to an angle class based on the angle at which the incident light beam must be scattered to strike the pixel. To achieve higher resolution at small angles, fractions of the pixel area may be assigned to adjacent angle classes when an angle class boundary falls across the pixel. The assignment is simplified by use of the virtual coordinate system which treats all scattering as originating from the optic center of the lens.

To calculate the angle at which the incident beam must be scattered to strike the pixel, first the angle is calculated which is subtended at the optic center of the lens by the distance in the focal plane from the focal point to the pixel. Appropriate corrections are made for any refraction which occurs in the scattered ray. This angle is the scattering angle if the light beam is coincident with the optic axis (beam angle=0). If the light beam makes an angle with respect to the optic axis (beam angle>0), then the beam angle (corrected for refraction effects) must be geometrically combined with the previously calculated angle to determine the scattering angle, and hence the angle class to which the pixel belongs.

The preferred embodiment of the present invention combines normalized output values from all of the pixels in the same angular region so that the average intensity of light falling in a given angle class may be determined. The normalized combination technique is extended to include contributions from the same angle class from multiple exposures arising from use of the light detector in different angular relations to the incident beam or from use of the light detector in the same angular relation to the incident beam for different light doses.

In general, each exposure will have valid intensity data for only a subset of the full range of angles necessary to produce the particle size distribution. Usually, the pixels in angle classes for angles smaller than the usable angles will be overexposed (saturated), and the pixels in angle classes for angles larger than the usable angles will be underexposed. Valid intensity data for these angle classes must be obtained by taking longer or shorter exposures, or by varying the intensity of the incident light beam.

The ability of the present invention to locate the center of the incident light beam means that there is no mechanical alignment required in the normal operation of the apparatus. On the other hand, certain characterization adjustments are required to interpret the pixel array output values properly. For example, a particular pixel may provide either no or an anomalous output with respect to the amount of light falling on it. The present invention can determine when a pixel is not operating within proper operating limits, and a "bad pixel map" is maintained to identify and compensate for such pixels. Additionally, certain pixel arrays are known to provide non-zero pixel output values even when no light is falling on the pixel array. The non-zero output values are a result of thermal effects in the pixel and increase linearly with time. Therefore, the electric charge accumulating in a particular pixel with no light on the pixel can be expressed as the product of a "dark current" value characteristic of that pixel and the length of time since the last reset of the pixel array. The increase in pixel output with time due to this effect is sometimes called "dark current buildup". The present invention determines the dark current values for each pixel of the pixel array in order to compensate for this effect.

Preferably, the components of the present invention include a light source, a CCD, and a converging lens. The particles to be investigated are positioned such that the light from the light source is scattered by the particles, and the converging lens is positioned to focus a portion of the scattered light onto the CCD. A lens used in this manner is sometimes called a Fourier transform lens. In order to facilitate different configurations of the analyzer, the lens can be a zoom lens. The analyzer includes a processor and data storage memory configured to receive and reduce pixel output data from the CCD. The CCD output data provides a measure of the intensity of light that is scattered at an angle relative to the beam. Preferably, the CCD provides anti-blooming protection up to a predetermined intensity of light incident on the CCD, regardless of exposure time.

The light source is preferably a laser and is preferably movably mounted in the analyzer such that the angle between the beam emitted from said laser source and the axis of the lens may be varied. Alternatively, the CCD and the lens may be movably mounted for movement together, such that the angle between the beam emitted from the laser source and the axis of the lens may be varied. The particles may be dispersed in a sample cell. The sample cell has a cell width in a direction along the axis of the lens and may have an adjustable cell mount capable of receiving a plurality of sample cells of differing cell widths.

Before the particle size analyzer is used for analytical work, the CCD preferably is characterized by uniformly illuminating it with laser light doses at a number of different light intensities. The bad pixel map, as discussed above, is created at this time. In addition, the dark current buildup of each pixel of the CCD is determined as a function of time, so that the output data for each pixel can be modified based on the dark current function and the duration of each exposure. Finally, an output function for each pixel, relative to incident dose intensity, is determined so that the output data for each pixel may be modified based on the output function and the amount of light dose used in each exposure. The output function corrects for any variation in sensitivity or offsets which may be present in a given pixel's response to light. Once the CCD has been characterized, pixel-by-pixel, the analyzer is ready for use to determine particle sizes.

A typical preferred operation of the analyzer to obtain particle size data involves dispersing the particles under investigation, exposing them to a dose from a collimated light beam so as to scatter a portion of the light, passing a portion of the scattered light through the lens, detecting a portion of the light passing through the lens with a pixel array, and reading the output data from the pixels into a memory device. The results of the first dose are analyzed to determine if additional doses are required to get readings within the dynamic range of the pixels for all angles desired for obtaining a good particle size distribution. If additional doses are required, the sizes of additional doses are determined by varying either or both the length and intensity of the pulse of light from the laser source.

If the scattered light intensity in the region of interest cannot be brought within the dynamic range of the pixels by adjusting the dose of the incident light beam, then the sample container may be replaced with another sample container having a different width or the concentration of the sampling particles may be changed and, without physical realignment of the laser source, the lens, or the array of pixels, the operational steps set forth above can repeated.

During a series of exposures at the same position of the light source relative to the optic axis, the beam center is determined by projecting the unscattered beam onto the pixel array, reading the output data from a number of pixels into a memory device, defining an area of pixels where the magnitude of the output data is the highest, and determining a beam center located at the center coordinates of the area. If the unscattered beam does not fall on any pixels in the pixel array, the direction of the beam relative to the optic axis is recorded as the beam angle for later use in computing scattering angles. After the beam center or beam angle is determined, the pixels of the pixel array are assigned to a number of predefined angle classes. This is accomplished by determining the scattering angle for each pixel, as described above, and assigning the pixel to the class, or fractionally to the classes, to which it belongs.

For a given dose of light from the light source, scattered light intensity data is read from the pixels into a memory device and intensity values for a number of angle classes are determined. This procedure may be repeated if necessary for a number of different doses. If desired, the light source can be moved to a new angular orientation with respect to the beam axis and additional intensity values obtained for the same or additional angle classes. Finally, for each angle class, a composite intensity value is determined based on the combination of all of the exposures and scaled to compensate for differences in illumination characteristics during each of the exposures. The composite relative intensity values, recorded as a function of angle class, are then fit to a combination of theoretical intensity-versus-angle data sets using an inversion technique to obtain the particle size distribution.

Thus, it is an object of the invention to provide particle volume fraction data versus particle size for a spectrum of particle sizes with improved particle size resolution.

It is a further object of the present invention to provide a particle size analyzer capable of determining particle size distributions for samples with particle sizes ranging from less than 0.1 micrometer to 1000 micrometers or more, without re-alignment or mechanical adjustment of the analyzer.

It is a further object of the invention to provide a particle size analyzer which will resolve particle sizes over the size range from 0.1 micrometer to 1000 micrometers to better than 6% of the particle size being considered, automatically without operator input as to the nature of the mixture of particles.

It is a further object of the invention to provide scattering intensity data versus scattering angle for a plurality of total light doses and incident beam angles, with automatic normalization of the intensity data.

It is a further object of the invention to provide a particle size analyzer capable of effectively using a CCD, a CID, or other types of two-dimensional arrays of photosensitive elements for detecting and measuring scattered light intensity to obtain high angular resolution of the intensity data.

It is a further object of the present invention to provide a particle size distribution analyzer which can automatically determine regions on a two-dimensional array of pixels corresponding to variable angle classes relative to the beam direction.

It is a further object of the present invention to provide a method of determining the center of a light source beam that is incident on a two-dimensional array of pixels.

It is a further object of the present invention to provide a method of classifying various pixels in a two dimensional array into angle classes.

It is a further object of the present invention to provide a method of combining intensity data from a two-dimensional array of pixels, taken during multiple exposures, to obtain one composite intensity data profile for a given scattering pattern.

It is a further object of the present invention to provide a particle size distribution analyzer in which intensity data from like angle classes can be combined from different exposures using different incident beam intensities and incident beam angles.

It is a further object of the present invention to provide an apparatus capable of scattering light onto a two-dimensional array of pixels from multiple incident angles with multiple beam intensities.

It is a further object of the present invention to provide a particle size distribution analyzer which can use a converging lens capable of having different focal lengths and not require re-alignment of the analyzer components when the focal length of the lens is changed.

The present invention meets these objects and overcomes the drawbacks of the prior art, as will be apparent from the detailed description of the embodiments that follow.

BRIEF DESCRIPTION OF THE DRAWINGS

FIG. 8 shows the intensity recorded by the pixels near beam center in an exposure taken to determine beam center.

FIG. 9 shows the assignment of the pixels near beam center to their respective angle classes.

FIG. 11 shows pixel output values obtained by an embodiment of the invention for a 0.010 second exposure.

FIG. 14 shows pixel output values obtained by an embodiment of the invention for a 0.164 second exposure.

FIG. 17 shows pixel output values obtained by an embodiment of the invention for a 0.655 second exposure.

FIGS. 29A and 29B comprise a flow chart for the routine LOCATE OPTIC AXIS in an embodiment of the invention.

FIG. 30 is a flow chart for the routine CALCULATE OPTIC AXIS COORDINATES in an embodiment of the invention.

DESCRIPTION OF THE PREFERRED EMBODIMENTS

Figure 1:
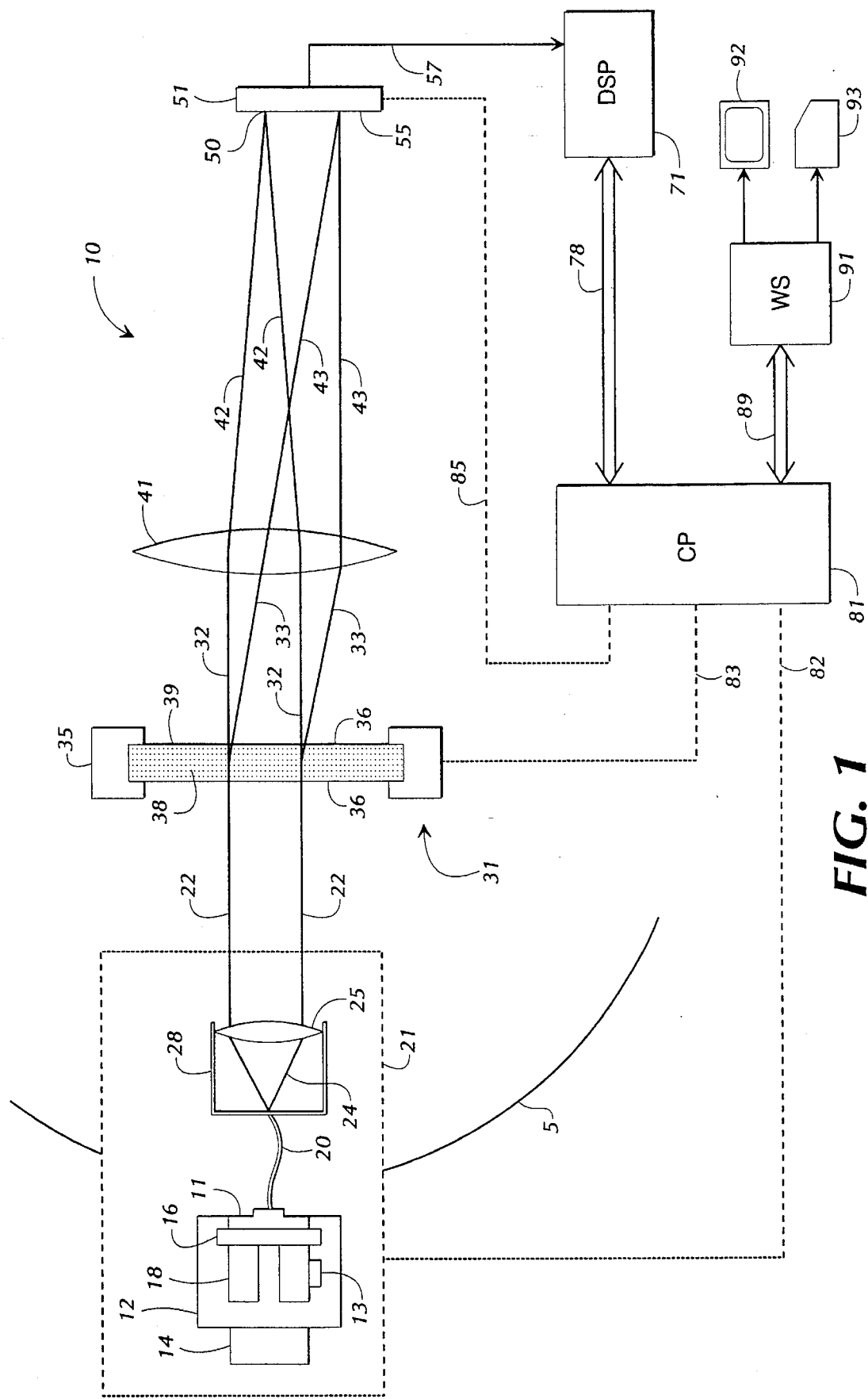
FIG. 1 is a plan view diagram of a particle size distribution analyzer depicting components of an embodiment of the present invention.

Referring now to the drawings, in which like numerals refer to like parts throughout the several views, FIG. 1 shows a plan view diagram of a particle size analyzer 10 depicting the components of an embodiment of the present invention. The principle components of this embodiment include a laser 11 in a beam assembly 21 to provide a collimated beam 22 of light to a sample of particles 38 contained in a sample cell 31. The particles 38 scatter light and the scattered rays 33 are focused in converging rays 43 on a CCD 51 by a converging field lens 41. The CCD records the intensity of the scattered rays 33 and provides data to a digital signal processor 71. The digital signal processor 71 processes the data from the CCD 51 and provides intensity-versus-angle data sets to a work station 91 for analysis. The analysis results in particle size information and plots which are output on a display screen 92 and a printer 93. The automatic features of the particle size analyzer 10 are under the control of a control processor 81, which can rotate the beam assembly 21 about the sample cell 31 and the sample cell 31 about its own axis, control the loading and dilution of the particles 38 in the sample cell 31, operate the laser 11 to make exposures, and in general control all of the mechanical operational features of the analyzer.

The laser 11 can be a solid state device, operating at an output wavelength of approximately 685 nm and nominal output power of 10 milliwatts, such as the Toshiba model TOLD 9140. The fact that the laser 11 produces coherent light is not important to the operation of the invention. Any source of light of minimal spread in wavelength may be used in the invention. Although different types of laser sources can be used in the present invention, the laser 11 preferably is a diode or solid state laser. It is also possible to use a helium/neon type laser source. If so, it is not necessary to use the fiber optics 20 described below, and a beam expander may be used to produce the collimated beam 22. A variable wavelength laser source could also be used.

The laser 11 is operated by a pulsed current source 14 providing control over the power and duration of the pulse, such as the "Laser Diode Driver" marketed by Seastar Optics, Inc., or a similar device by Oz Optics. The current source 14 provides drive current power to the laser 11 in pulses varying in duration from 1 microsecond to 10 seconds and in current from 0 to 50 milliamperes. The current source 14 can vary the drive current in steps of 0.1 milliamperes, repeatable to within 0.03 milliamperes. The power output of the laser 11 is a function of the drive current supplied by the current source 14.

The laser 11 is housed in a laser source assembly 12 which also contains a Peltier effect cooling device 16 for cooling the laser 11 to better control and stabilize the wavelength. The laser 11 preferably operates below room temperature, in a temperature range of 50 to 70 degrees Fahrenheit. A heat sink 18 preferably surrounds the laser 11 in order to absorb heat created during the operation of the laser 11. A temperature sensor 13 measures the temperature of the laser.

Fiber optics 20 are used to carry the beam emitted from the laser source assembly 12. The fiber optics 20 are attached to the laser 11 in a conventional manner. The other end of the fiber optics 20 is attached to a lens holder 28. The fiber optics 20 are preferably a single mode fiber which produces a conical exit beam 24 with a Gaussian intensity distribution. The exit beam is directed toward a collimating lens 25 held by the lens holder 28. Light emanating from the collimating lens 25 is a highly collimated beam 22 (parallel rays of light), the rays of which are preferably parallel to within 0.1 milliradian. The collimated beam is preferably circular in cross-section and approximately 10–15 mm in diameter. The laser source assembly 12, the fiber optics 20, and lens holder 28 are housed together in the beam assembly 21.

The term "collimated beam" used herein refers to essentially parallel rays of light however generated. Examples are, without limitation, a beam made parallel by a laser, a beam made parallel by a collimating lens or mirror regardless of the source of the light, and a beam originating effectively at infinity with respect to an optical system.

In order to adjust the incident angle of the collimated beam 22, the preferred embodiment also includes a rotation device 5 which is used to rotate the beam assembly 21 to various different beam angles with respect to the optic axis of the field lens 41. The center of rotation should be within the volume of the sample cell 31 containing the particles 38, and preferably at the center of the dispersed particles 38. The rotation device can be a rotation stage, or a goniometer platform, such as those manufactured by New England Affiliated Technologies, or any comparable rotation device. Rotation is controlled by the control processor 81. To avoid vignetting errors when the beam assembly is rotated, the entire volume of the collimated beam 22 inside the sample cell 31 must encounter the same concentration of particles 38 that are present when the beam angle is nominally zero.

The sample cell 31 is a container including two glass windows 36, each of which is approximately 1.5 mm in thickness. The glass windows preferably have an anti-reflection coating. In the preferred embodiment, one sample cell 31 is sufficient for determining particle sizes in the range 0.1 micrometers to 1000 micrometers. However, more than one sample cell 31 may be used if desired. The sample cell 31 is mounted in an adjustable frame 35 which can receive cells of a variety of widths. The two glass windows 36 are preferably spaced farther apart when analyzing larger particles and closer together when analyzing smaller particles. It will be understood that a smaller path length between windows is desired for small particles to minimize the possibility of a light ray interacting with more than one particle. However, when the particles are larger, a longer path length is needed to provide enough particles for scattering without too high a concentration in the suspension. The present invention allows the user to change sample cell width with little or no realignment needed.

The particles 38 may be delivered to the sample cell 31 and maintained in suspension by any apparatus known in the art. An example of such an apparatus is an autosampler as shown in U.S. Pat. No. 4,920,550, which patent is incorporated herein by reference. The autosampler uses a liquid 39 to disperse the particles 38. A fluid interface circuit between the sample cell 31 and the auto sampling device is described below with reference to FIG. 5. Alternatively, the scattering particles 38 can be dispersed in the scattering region by jets of air or other gasses, as is known in the art.

The sample cell 31 is positioned so that the entire cross section of the collimated beam 22 passes through the scattering region in the sample cell 31. Some of the light rays in the collimated beam 22 strike the particles 38 in the sample cell 31. The remainder of the light rays in the collimated beam 22 pass through the sample cell 31 without interacting with the particles 38 to form an unscattered beam 32. The choice of a suitable suspending and dispersing liquid 39 is affected by the size, density and chemical composition of the particles. The two windows 36 are aligned close to each other so that each light ray (not pictured) from the collimated beam 22 preferably strikes not more than one particle 38 dispersed in the liquid 39. In determining the particle size distribution of the particles 38, the refractive index of the air and of the liquid 39 through which the scattered rays 33 travel is taken into account in the interpretation of laser beam intensity data.

After traveling through the liquid 39 and interacting with the particles 38, at least a portion of the scattered rays 33 pass through the field lens 41. The field lens 41 is of the converging type and is positioned such that its distance to the CCD 51 is equal to its focal length and its distance to the sample cell 31 is much less than its focal length. At this position, scattered rays 33 which are parallel to each other, and which pass through the field lens 41, are directed in converging rays 43 toward the same point on the CCD 51. The field lens 41 thus operates as a Fourier transform lens. Converging rays 42 from the unscattered beam 32 strike the CCD at a beam center 50. To avoid vignetting errors, all light scattered at an angle for which scattered light intensity data is being taken must reach the field lens 41 and be focused to a point on the CCD 51. Preferably, the field lens has a focal length of about 200 mm and is about 50 millimeters in diameter.

The converging field lens 41 can be a single lens or multiple lenses may be used in combination with each other or separately. Generally, a long focal length lens (up to 2 meters) is most efficient for measuring the particle size distribution of larger particles (up to 4000 micrometers). On the other hand, a shorter focal length (as little as 35 mm) is more efficient in measuring smaller particles (down to 1 micrometer). For particles smaller than 1 micrometer in size, the apparatus should be capable of measuring scattering intensity at scattering angles up through 36 degrees. To accomplish this, a shorter focal length lens can be used with a larger CCD 51 or with multiple smaller CCD's 51. Alternatively, a preferred option is to move the orientation of the beam assembly 21 such that scattering angles larger than that subtended by the CCD 51 can be measured by using a series of exposures, each at a different beam angle.

The field lens 41 may be a zoom lens, of the type well-known in the camera art. The use of a zoom lens provides for changing the effective focal length of the field lens 41 without replacing the lens itself. The zoom lens is advantageous when used in combination with the CCD 51 because, as described in detail below, no alignment of the lens is needed to position the beam center 50 on the CCD 51.

Although an apparatus according to the present invention is most versatile when it incorporates a zoom lens or lens of a multiple focal lengths, an advantage of the present invention is that a wide range of data can be obtained using a single field lens 41 in conjunction with the other improvements described herein.

The CCD 51 receives converging rays 42 and 43 from the field lens 41. The CCD is located in the focal surface of the field lens 41. For good positional resolution, the CCD 51 preferably has on the order of 1000 rows and 1000 columns. Preferably, the CCD is the model KAF-1300L CCD manufactured by Eastman Kodak. This CCD has 1024 rows and 1296 columns of pixels 55, the rows being perpendicular to the columns. Each of the pixels 55 is square with sides approximately 0.016 mm in length. The pixel-to-pixel spacing is 0.016 mm in both the horizontal and vertical directions and each pixel subtends an angle of about 0.004 degrees when used with the preferred 200 mm focal length field lens 41. The size of the pixels is such that there are between 15,000 and 30,000 pixels in each angle class for scattering angles greater than about 1.0 degree, where the light intensity is low compared to that for forward angles. Averaging the output data from this number of pixels enables the analyzer 10 to provide an excellent signal-to-noise ratio. The overall size of the pixel area of the CCD 51 is 20.7 mm wide by 16.4 mm high. In conjunction with the preferred 200 mm focal length field lens 41, the CCD 51 subtends approximately 6 degrees when viewed from the field lens 41. The CCD is oriented such that its surface is perpendicular to the optic axis of the field lens 41.

The CCD 51 may equipped with a conventional temperature control mechanism (not shown) in order to regulate the temperature of the CCD 51. By regulating the temperature of the CCD 51, the "dark current" effects can be minimized. In addition, the CCD 51 preferably has anti-blooming protection, such as that afforded by the model KAF-1300L CCD.

The analyzer 10 may also use a photodiode array, such as the EG&G Reticon model RA0128A or model RA1662N in place of the CCD 51. The model RA0128A has 128 rows and 128 columns of pixels, spaced 0.060 mm center-to-center in both the row and column directions. The model RA1662N has a 16×62 matrix of pixels, spaced 0.100 mm center-to-center in both the row and column directions. In each model, each photodiode integrates the photocurrent from the time of the last reset signal. However, for both models, resolution is less than obtained by the Kodak model KAF-1300L CCD.

The CCD 51, in conjunction with its associated conventional electronics (not shown), provides a measurement of the light intensity falling on each pixel 55. The CCD 51 is used with a standard analog-to-digital converter (not shown) which is well-known in the art. The preferred embodiment uses a 12-bit analog-to-digital converter which is capable of converting intensity data to values which range from 0 to 4095 for each pixel 55. Other bit size analog-to-digital converters may be used; for instance, an 8-bit analog-to-digital converter would provide the intensity values for each pixel 55 ranging from 0 to 255.

It should be noted that the methods of determining beam center and of classifying pixels to angle classes, described below, are facilitated if the pixel array contains regularly spaced pixels, such as, for example, pixels placed on a rectangular or hexagonal grid.

The CCD 51 operates under control of the control processor 81 by means of control line 85 and passes its data to the digital signal processor 71 via data line 57. The digital signal processor 71 is programmed with software and configured to reduce the pixel intensity data measured by the CCD 51 to obtain and normalize the intensity of scattered light at various scattering angles. The digital signal processor 71 preferably also contains the ability, given the pixel intensity data available, to determine the pixel location of beam center 50 on the CCD 51, to classify pixels into a variety of angle regions on the CCD 51 based in part on each pixel's distance from the beam center 50, to combine intensity data for different exposure times and laser beam intensity values in order to formulate a composite set of intensity-versus-angle data, and to reclassify pixels to angle regions when the incident angle of the collimated beam 22 is changed. The digital signal processor 71 preferably is a Texas Instrument TMS 320 or similar processor.

The digital signal processor 71 passes the intensity-versus-angle data to the control processor 81 via data line 78. The control processor 81 is preferably a Motorola 68040 or similar processor which can directly address random access memory in excess of one gigabyte. The control processor 81 controls the loading of the particles in the sample cell and the orientation of the sample cell by control line 83. The control processor 81 controls the operation of the laser 11 and the beam angle of the beam assembly 21 by control line 82. The control processor 81 passes the intensity-versus-angle data to the work station 91 via data line 89. The work station 91 may be an IBM PC or compatible which can analyze the intensity-versus-angle scattering data to determine particle size.

Figure 2:
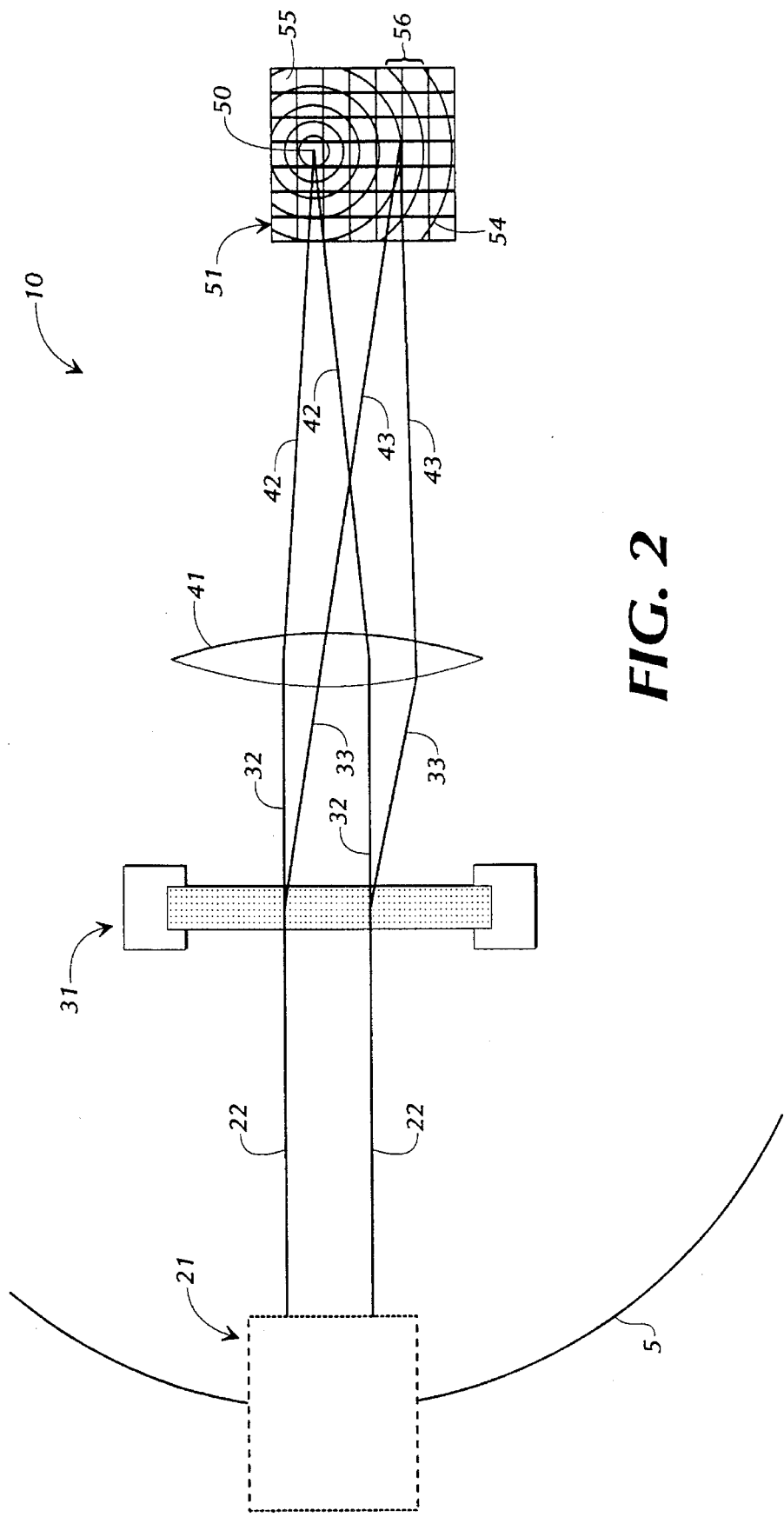
FIG. 2 is a simplified diagram of an embodiment of the invention depicting a plan view of a light source, sample cell, and lens, combined with an elevation view of a CCD to show the concept of angle classes.

FIG. 2 shows a plan view diagram of the particle size distribution analyzer 10 with a view of the CCD 51 rotated 90° such that the face of the CCD 51 is displayed (as in an elevation view). This orientation of the CCD 51 shows rows and columns of the pixels 55 and a point representing the beam center 50. Although the operation of the apparatus 10 does not depend in general on where the beam center 50 is located on the CCD 51, it is generally preferable to locate the CCD 51 such that the beam center 50 is located near one edge of the CCD 51 when the beam assembly 21 is approximately at zero degrees relative to the optic axis of the field lens 41. This location provides data for the maximum range of scattering angles (up to approximately 5 degrees) before rotating the beam assembly 21 to obtain data at larger scattering angles (if necessary). The location of beam center 50 should be chosen so that the CCD 51 may contain several angle classes corresponding to very small scattering angles, each comprising the entire circular annulus about beam center 50. FIG. 2 also illustrates the concept of angle class when beam center 50 lies on the CCD 51. Circular arcs provide class boundaries 54 centered on the beam center 50 and divide the CCD 51 into angle classes 56. Each circular annulus is an angle class and corresponds to a particular scattering angle; the larger the circle, the larger the scattering angle.

Figure 3:
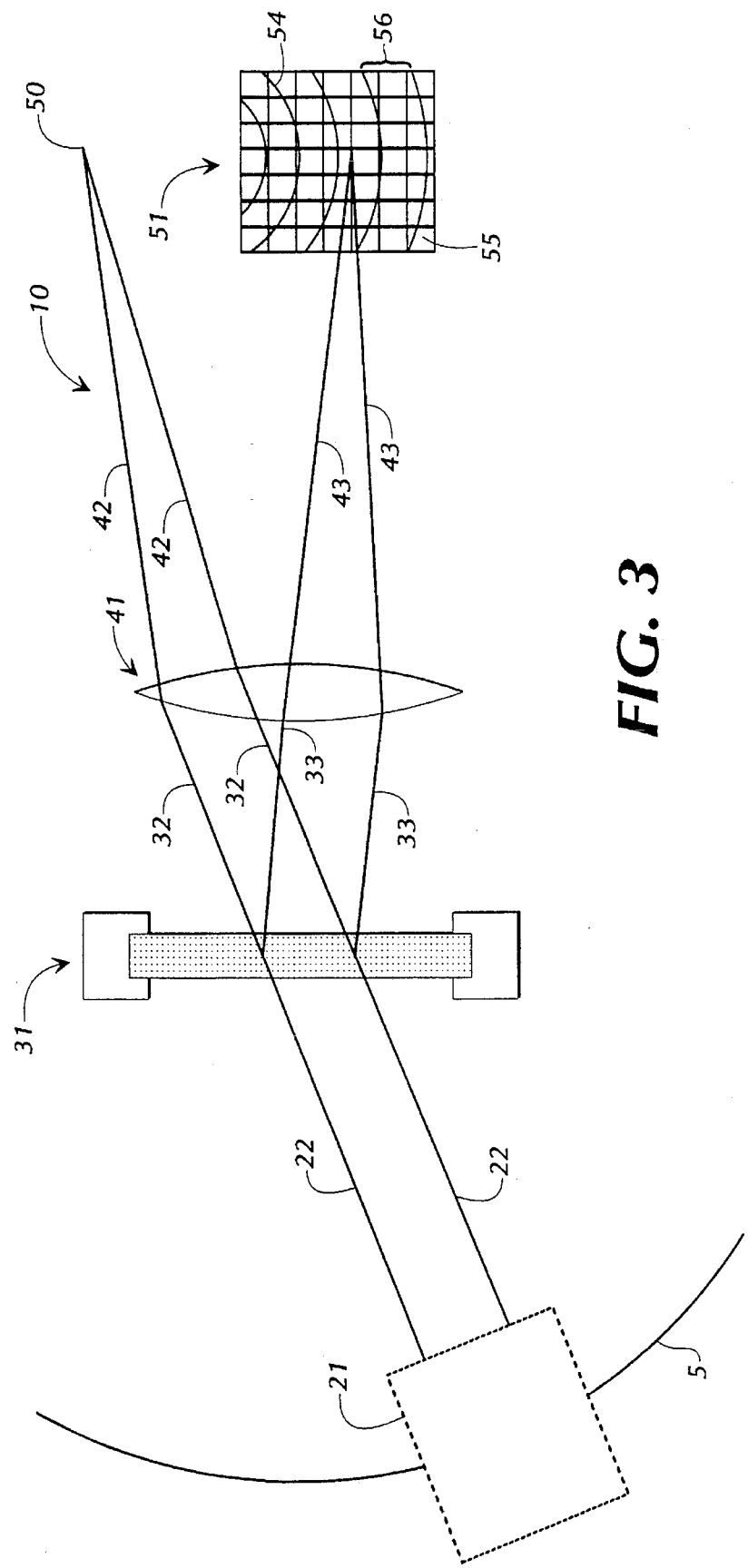
FIG. 3 depicts the elements of FIG. 2 with the light beam directed to an area off the CCD.

In FIG. 3, the particle size distribution analyzer 10 is again shown with the CCD 51 rotated 90° such that the face of the CCD 51 is displayed. The beam assembly 21 as shown in FIG. 3 is aligned so that the collimated beam 22 makes a positive angle with respect to the optic axis of the field lens 41. The beam center 50 is now off the CCD 51. In this configuration, the CCD 51 receives light scattered at larger angles than when the collimated beam 22 is aligned with the optic axis of the field lens 41. To assign a pixel 55 of the CCD 51 to an angle class 56 when the beam center 50 is off the CCD 51, the scattering angle corresponding to the pixel 55 must be determined, as explained in detail below, from the location of the pixel 55 and the amount of the beam angle. Obtaining scattering intensity data at different beam angle is accomplished by rotating the lens 41 and CCD 51 together or, preferably, by rotating the beam assembly 21 a known angular distance between selected exposures.

For a CCD 51 which subtends an angle of approximately 5 to 6 degrees, it is possible to cover the entire range of scattering angles (0 through 180 degrees) by stepping the beam assembly 21 with the rotation device 5 in beam angle increments of 5 degrees, from 0 to 175 degrees. Generally, the exposures taken with the beam center 50 located off the CCD 51 are longer than exposures taken when the beam center 50 is located on the CCD 51 because scattering intensity is less for larger scattering angles. A longer exposure is needed to collect enough light to provide a measurable intensity at these larger scattering angles.

Figure 4:
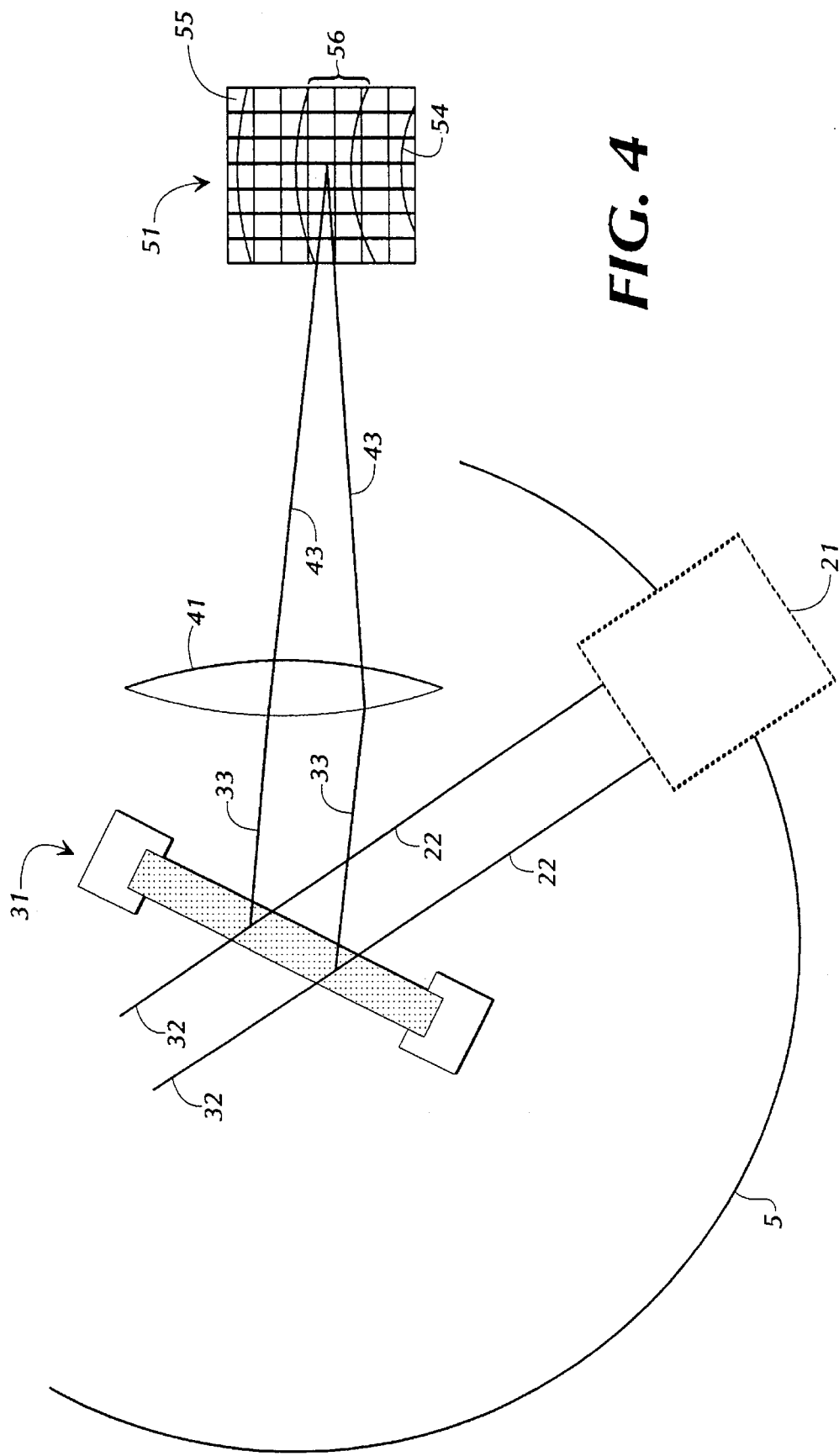
FIG. 4 depicts the elements of FIG. 2 with the light beam directed so that the CCD will receive backscattering from the sample.
Figure 4A:
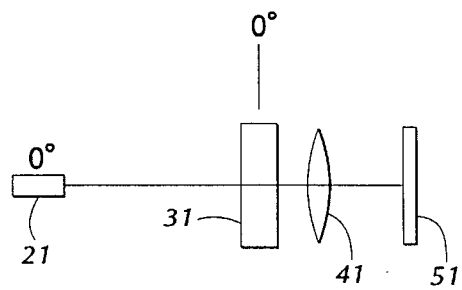
FIGS. 4A–4F are plan view schematics showing the relative orientations of the light source, sample cell, lens and CCD for beam angles of 0°, 45°, 90°, 90°, 135°, and 180°, respectively.
Figure 4B:
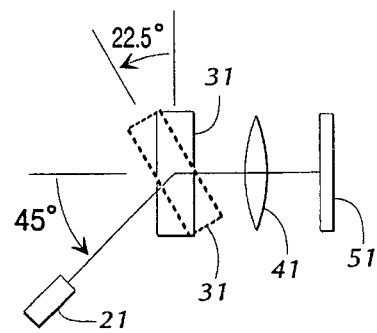
Figure 4C:
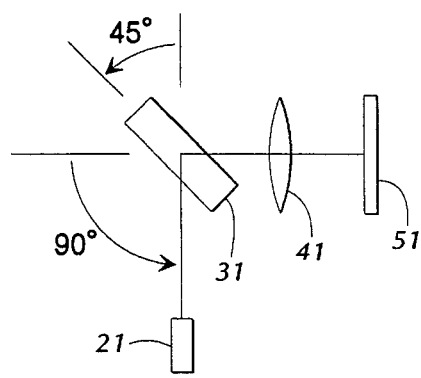

FIG. 4 shows another plan view diagram of the particle size distribution analyzer 10, again with a view of the CCD 51 rotated 90° to show the face of the CCD 51. In the configuration of FIG. 4, the beam assembly 21 has been rotated a positive angle of approximately 135 degrees to a "back scattering" position. Back scattering is a term used whenever the scattering angle is more than 90 degrees. Back scattering may be useful when analyzing the particle size distribution of extremely small particles, typically particles smaller than one micrometer in size. When positioning the beam assembly 21 in a back-scattering position, the CCD 51 measures beam intensity of the light scattered by the dispersed particles 38 back toward the light source.

Figure 4D:
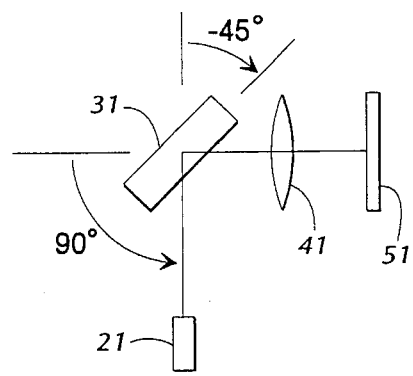
Figure 4E:
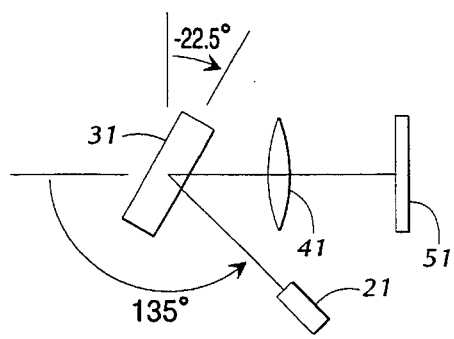
Figure 4F:
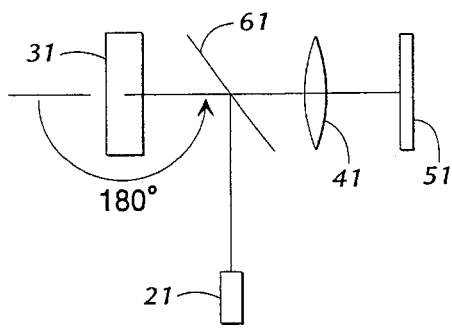

When rotating the beam assembly 21 to beam angles larger than approximately 45°, it is preferable to also rotate the sample cell 31 by an amount approximately equal to one-half the beam angle. Rotation of the sample cell is about an axis passing through the dispersed particles 38 normal to the optic axis of the lens 41 and is controlled by the control processor 81. Preferably, the axis of rotation passes through the center of the dispersed particles 38. FIGS. 4A through 4F illustrate the relative orientations of the beam assembly 21, sample cell 31, lens 41 and CCD 51 for beam angles of 0°, 45°, 90°, 90° (again), 135°, and 180°. FIG. 4D shows an alternate orientation of the sample cell 31 compared with that shown in FIG. 4C, and orients the sample cell 31 for collecting back scattering data. To provide for the extreme backscattering angle of 180°, as shown in FIG. 4F, the sample cell 31 is removed and mounted a distance away from the CCD 51. A half-silvered mirror 61 is placed at a 45-degree angle in the adjustable frame 35 to provide partial reflection of the collimated beam 22 and partial transmittance of the scattered rays 33.

Figure 5:
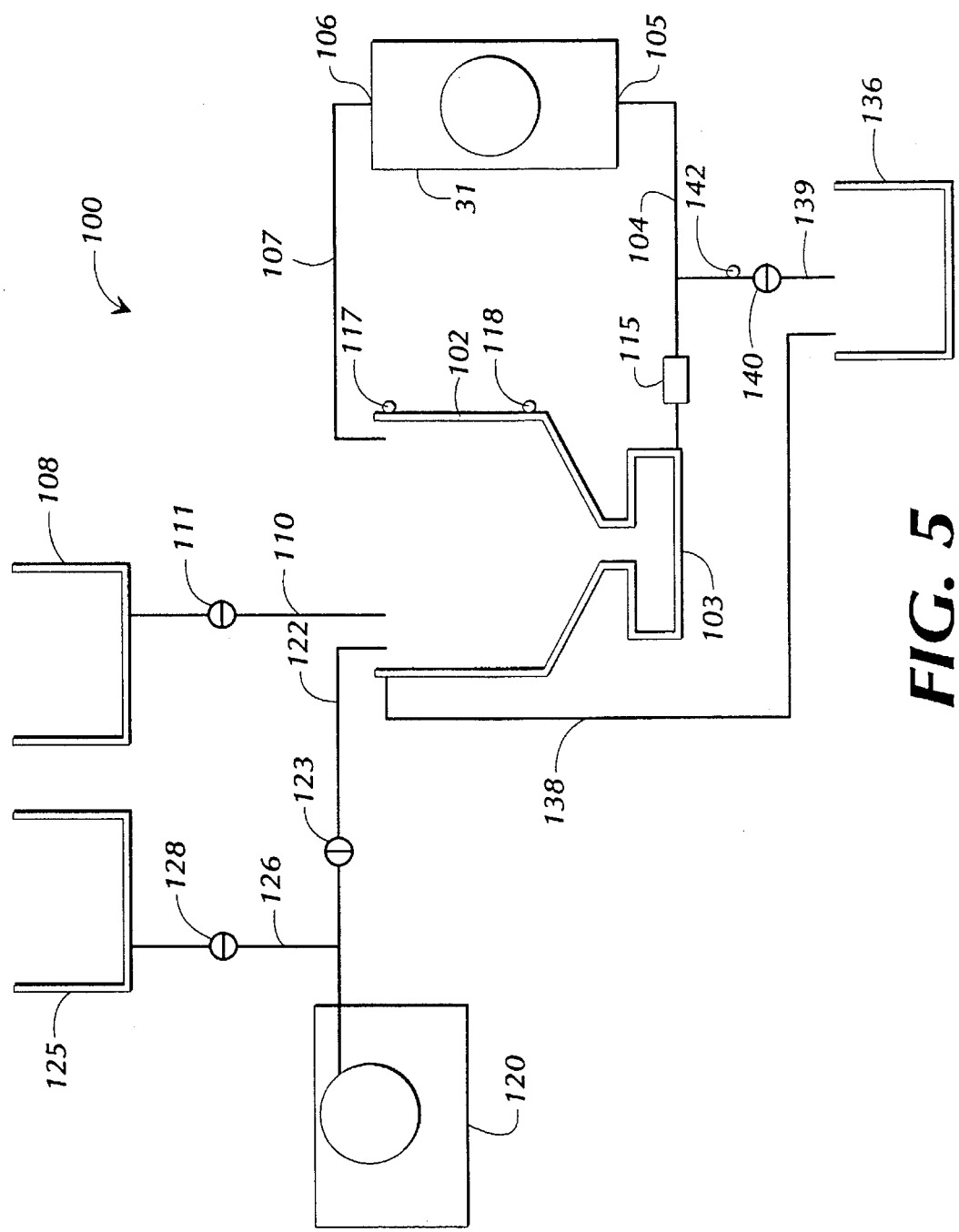
FIG. 5 depicts the components of an embodiment of the invention which provide the capability of suspending the sample in a fluid in a sample cell.

A fluid circuit 100 for supplying the cell 31 with dispersed sample is shown in FIG. 5. A reservoir 102 for holding sample particles and dispersing fluid is connected via a non-pulsatile pump 103 along a fluid line 104 to an inlet 105 of the sample cell 31. The pump is operated in response to commands received from the control processor 81 to deliver pure liquid or dispersed sample to the cell 31. An outlet 106 of the cell 31 leads along a return line 107 back to the reservoir 102. A container 108 of dispersing fluid is connected to the reservoir 102 via line 110, which includes a valve 111. In the embodiment shown, flow from the container 108 into the reservoir 102 is by gravity. A flow cell with an ultrasonic probe 115 is positioned in the line 104 to disperse the sample particles in the dispersing fluid.

Sample particles may be inserted manually into the reservoir 102, such as from a syringe or beaker, or automatically from an autosampler 120. Those skilled in the art will understand that typical autosamplers are programmed to deliver a series of samples to an analyzer according to a preset schedule, and in response to signals received from the analyzer. The autosampler 120 shown in FIG. 5 includes its own pump, and is connected to the reservoir 102 by a line 122 including a valve 123. A rinse liquid supply 125 is provided and is connected to the line 122 by a line 126 including a valve 128, between the autosampler 120 and the valve 123.

The reservoir 102 preferably includes a pair of level sensors, a full level sensor 117 and a low (primed) level sensor 118, connected to the control processor 81. These sensors can be monitored for the purpose of controlling the filling or draining of the reservoir 102, and for providing alarms if insufficient fluid is present for analysis to begin or continue. An overflow line 138 also protects against overfilling of the reservoir 102. The overflow line leads to a waste receptacle 136. The pump 103 also can be operated to pump fluid from the reservoir 102 into the waste receptacle 136 along a waste line 139 including a valve 140. A fluid presence (empty) sensor 142 in the line 139 monitors whether any fluid remains in the system above the sensor 142.

The valves 111, 123, 128, and 140 can be manually operated, or solenoid operated by the control processor 81. The fluid circuit 100 operates during sample analysis in the manner described below in connection with FIG. 35.

To operate the particle size analyzer 10, the responses of the CCD 51 and the laser 11 are characterized as explained in detail below. For each beam angle at which the analyzer is to be operated, baseline data for the analyzer 10 is obtained by collecting light intensity data with no particles 38 in the sample cell 31. The baseline data are stored for later subtraction from the scattering intensity data. For each analysis with particles present 38, a number of exposures are made at varying beam doses to obtain scattering intensity data. The beam doses (a function of the laser drive current and exposure time) are selected so as to obtain scattering intensity data within the dynamic range of the CCD 51 for each of the angle classes 56 of interest for the given beam angle. When all exposures are made, the scattering intensity data from each exposure are normalized and the data from all exposures are combined to provide a composite intensity-versus-angle data set. The intensity-versus-angle data set is then subject to a mathematical inversion process to extract the particle size distribution.

EXAMPLE 1

Before describing the process of the invention in detail, it will be helpful to illustrate the process with a specific example. In this example, the analyzer uses a CCD which comprises an array of 1024 rows and 1296 columns of pixels in a rectangular array. Each pixel is 0.016 mm square. The CCD uses an 8-bit analog-to-digital converter, so that the digital output for each pixel varies from 0 to 255. The CCD is positioned in the focal plane of a 200 mm focal length converging lens and subtends an angle of about 6 degrees when viewed from the optic center of the lens. The analyzer is aligned so that the beam strikes the CCD in the upper left corner. The light source of the analyzer is a laser, emitting light with a wavelength of 673.4 nm. The sample is comprised of 108 micrometer diameter polystyrene spheres dispersed in water.

Figure 6:
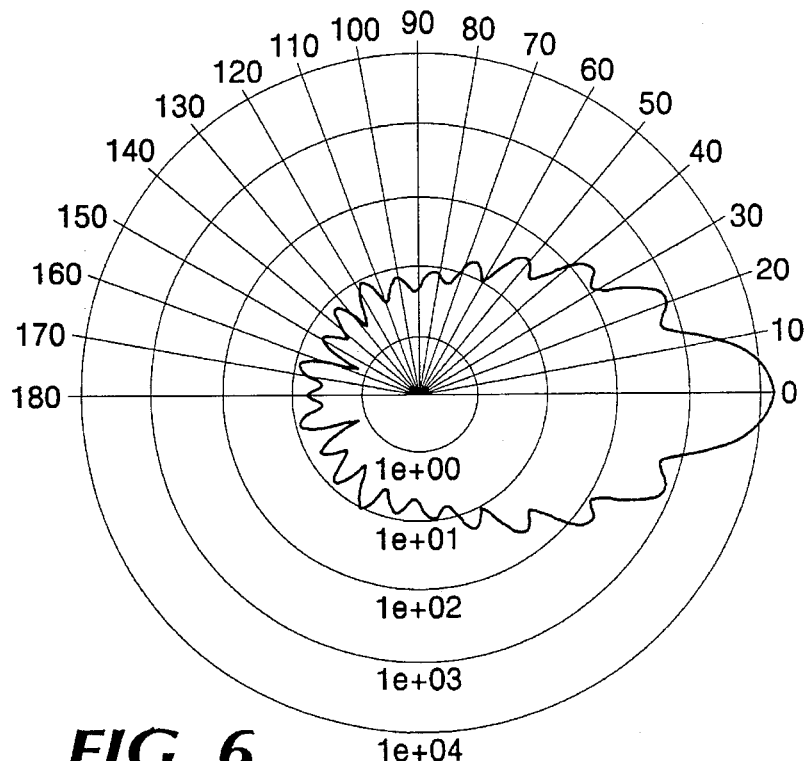
FIG. 6 is a polar diagram of log intensity of scattered light as a function of angle predicted as by the Mie theory for 2 micrometer polystyrene spheres.
Figure 7:
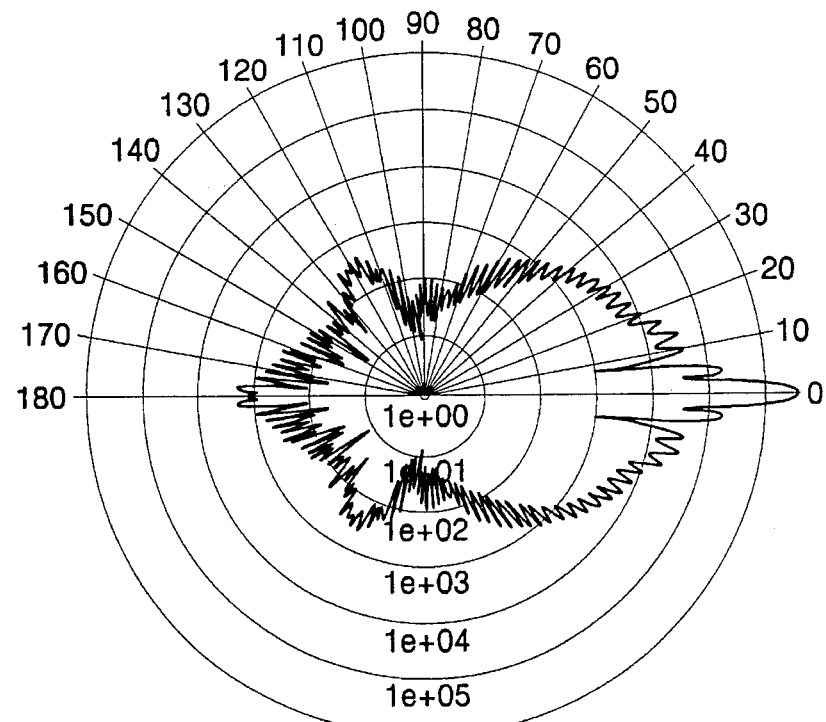
FIG. 7 is a polar diagram of log intensity of scattered light as a function of angle as predicted by the Mie theory for 10 micrometer polystyrene spheres.

FIG. 6 shows a polar diagram of the log of the intensity of the scattered light from 2 micrometer polystyrene spheres as a function of the angle of the scattered light relative to the direction of the incident beam, as computed by Mie theory. The first minimum in the intensity distribution occurs at about 15 degrees relative to the beam angle. FIG. 7 shows another polar diagram of the log of the intensity of the scattered light, in this instance from 10 micrometer polystyrene spheres. Relative to the distribution for 2 micrometer spheres, the intensity distribution is compressed in the forward direction, and the first minimum in the distribution occurs at about 4 degrees. From this comparison, it is apparent that the intensity distribution for the 108 micrometer spheres of this example will be even more compressed in the forward direction. Indeed, Mie theory predicts that the first minimum will be at about 0.5 degrees, with intensity variations of over 100 to 1 between 0 and 1.0 degrees. To measure accurately the extreme intensity variations in this interval, a series of three exposures are made, with exposure times of 0.010 second, 0.164 second, and 0.655 second. The example shows the data collected from the CCD for the three exposures and how these data are normalized and combined to the extract particle size information.

Each time the laser light source illuminates the sample, scattered light falls on the CCD. Data from the CCD represents a measurement of the intensity distribution, or patterns of the scattered light falling on the CCD for each exposure conducted during an analysis. The process of reducing the scattered light patterns to particle size data involves two basic parts:

1. Reducing the CCD pixel data to intensity-versus-angle data, and
2. Fitting this experimental intensity-versus-angle data to a combination of theoretical intensity-versus-angle data sets from a given theory (such as Mie theory or Fraunhofer theory) for different particle sizes.

The first step is to locate the center of the beam on the CCD. This is done by locating the area of maximum intensity. FIG. 8 shows the output recorded for each of the relevant pixels in an exposure taken to determine beam center. The minimum size rectangle is identified which contains all pixels with intensity above a threshold (in this case 50). The center coordinate is determined by averaging the center coordinates of each pixel in the rectangle, weighted by the square of the intensities in those pixels. The center coordinate for each pixel is its row and column numbers plus 0.5. Beam center for this example is row 130.9 and column 136.7.

Light scattered by spherical particles will be symmetric about the beam center and vary with angle from the beam. When the beam angle is zero, the cone of scattered light for each angle relative to the beam intersects the CCD plane in a circle concentric about beam center. The light striking the CCD in the annular region between two such concentric circles is the light scattered between the corresponding angles. Thus to identify the light intensity scattered in each of a series of angular intervals, the CCD image must be mapped into a series of concentric rings around the beam center. When the beam angle is not zero, the CCD image must be mapped to a more general conic section.

The average intensity for each angular interval is the average intensity of the pixels in its annular ring on the CCD. For each angle the radial distance from beam center on the CCD is calculated. The equation, correcting for refraction exiting a waterfilled cell, is:

Radial distance=F*tan(arc sin (sin (angle)*Nfluid/Nair))

where F=focal length of the field lens (200 mm.), Nfluid and Nair are the refractive indices of water (1.33) and air (1.00), respectively. Refraction by the glass of the cell window cancels out. If the fluid suspending the sample particles is not water, the refractive index of the fluid is used.

FIG. 9 contains, for each pixel, the index of the angle class containing the innermost corner of the pixel. The fraction of the pixel's area which falls in that inner angle class is calculated; the remainder of the pixel's area is assigned to the next angle class farther out. The angles are at intervals of 0.0025 degrees.

Using this classification of CCD pixels into angle classes, any CCD exposure made with the same alignment of the light source relative to the CCD can be reduced to intensity-versus-angle data. This reduction is accomplished by averaging the intensity readings for all included pixels in an angle region, weighting partially included pixels by the fraction of area included.

The next problem is to classify, for each exposure, the data from each pixel into an angle class. Each exposure may contain some pixels that are underexposed or overexposed. Therefore, each pixel is checked and the output is ignored if it falls below minimum or above maximum value (4 and 254 respectively in the case of an 8-bit analog-to-digital converter.) Thus, pixels with output values between the minimum and the maximum are used in determining the average intensity for an angle class. If too many pixels in an angle class are out of range, or too few pixels fall in that class, the intensity data for that class is considered invalid and not used for further calculations.

In general, each exposure will have valid intensity data for only a subset of the full range of angle classes. Usually, angles smaller than the usable angles will be overexposed, and angles larger than the usable angles will be underexposed. Valid intensity data for these angular ranges must be obtained by taking longer or shorter exposures, or by varying the intensity of the incident light beam.

FIGS. 10 through 18 show a series of three exposures of increasing exposure times taken of 108 micrometer diameter polystyrene spheres in water. Three figures for each exposure are shown:

(1) the CCD image of the scattered light (for compactness, only one quadrant of the image is shown); (2) a selected representation of digital pixel output values for the image shown in the previous figure; and (3) a graph of intensity versus angle, derived by classifying the pixels into angle classes using the correspondence shown in FIG. 9.

Figure 10:
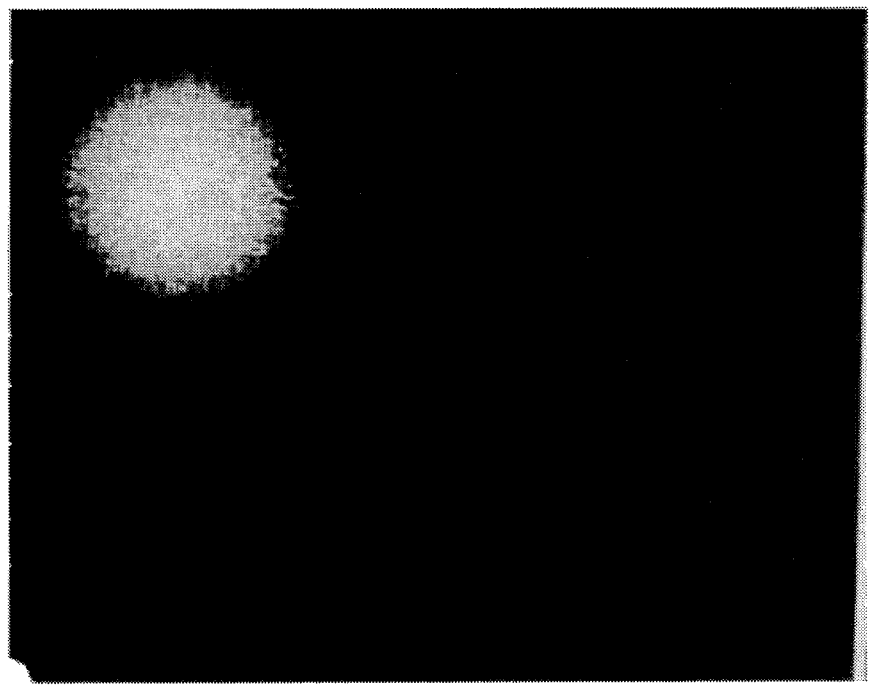
FIG. 10 shows the CCD image of scattered light for an exposure time of 0.010 second.
Figure 12:
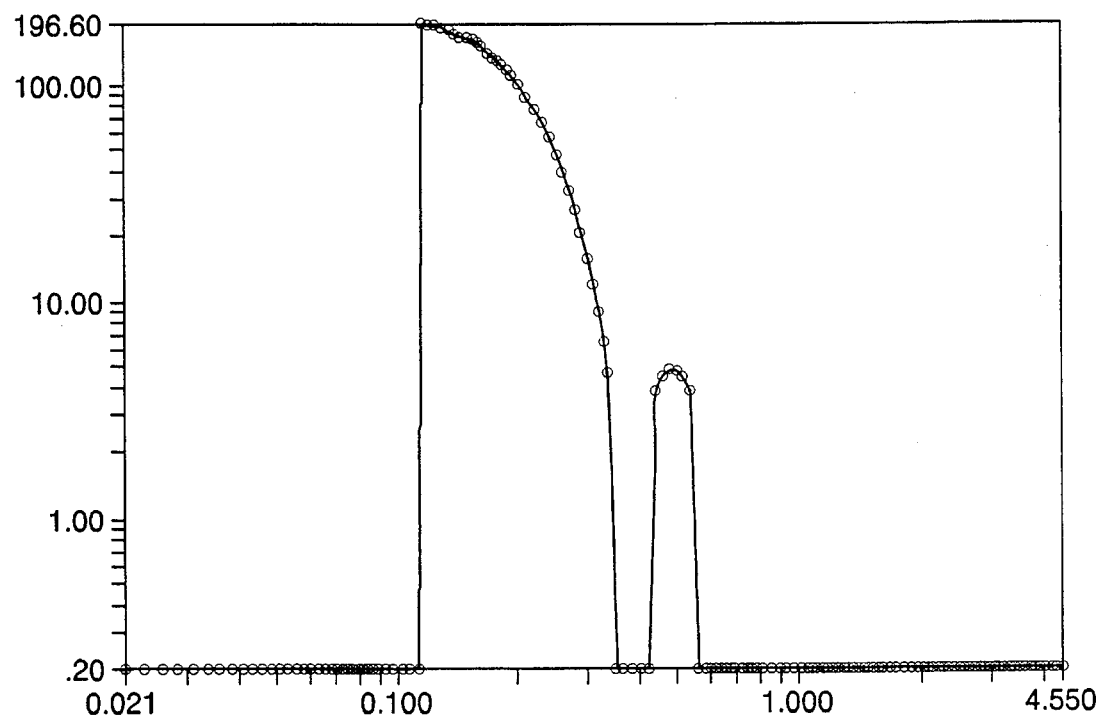
FIG. 12 shows a graph of intensity versus angle for a 0.010 second exposure as obtained by an embodiment of the invention.

FIG. 10 shows the CCD image of light scattered by 108 micrometer diameter polystyrene spheres in water, with an exposure time of 0.010 second. Exposures of short duration such as this will saturate the pixels of the CCD in a small area around beam center and provide measurable outputs as the radial distances from beam center to the pixels increase. The CCD pixel output values for the 0.010 second exposure is given by FIG. 11. The number of the pixel row is given in the left-most column of FIG. 11 and the number of the pixel column is given in the top row. This figure is for the pixel area around the beam center at row 130.9 and column 136.7. The pixels close to beam center exhibit the saturation value of 255, but the pixels in columns 141 and higher begin to show measurable intensity less than 255. The intensity of the peak of the second ring (not visible in FIG. 10.) is just above an underexposure cutoff threshold value of 4 counts and is beyond the set of rows and columns shown in FIG. 11. FIG. 12 shows a graph of intensity versus angle for the 0.010 second exposure. Classes inside of approximately 0.11 degrees are overexposed (pixel output values of 255) and excluded, and classes outside of approximately 0.55 degrees are underexposed (pixel values of 4 or less) and excluded. The valley between 0.34 degrees and 0.42 degrees is also underexposed and will need a longer exposure to adequately characterize it. The peak of the second scattering ring at about 0.5 degrees is just over the underexposure cutoff..

Figure 15:
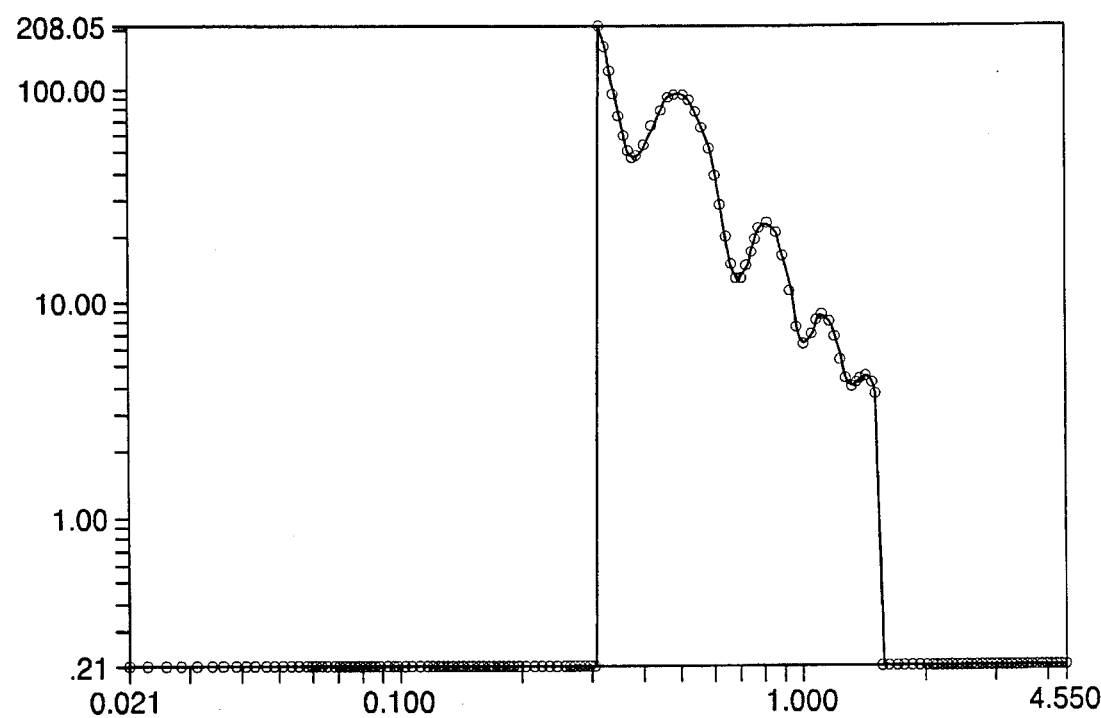
FIG. 15 shows a graph of intensity versus angle for a 0.164 second exposure as obtained by an embodiment of the invention.
Figure 13:
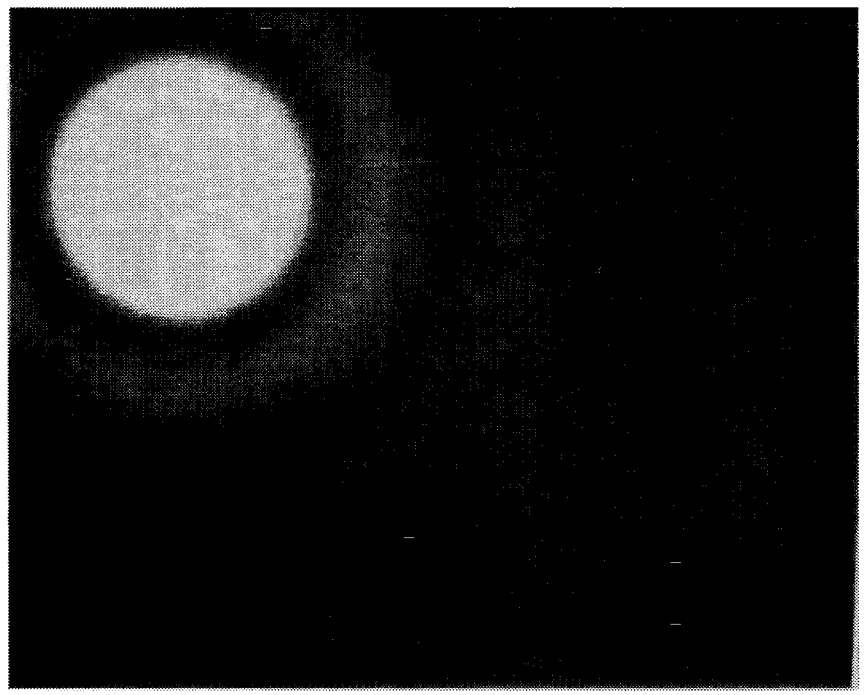
FIG. 13 shows the CCD image of scattered light for an exposure time of 0.164 second.

FIG. 13 shows the CCD image of light scattered by 108 micrometer diameter polystyrene spheres in water, with an exposure time of 0.164 second. For the 0.164 second exposure, a portion of the pixel output values are given by FIG. 14. This figure is for the pixel area corresponding to a scattering angle of approximately 0.3 degrees. In this area, as shown in FIG. 15, the intensity is dropping from the saturation value of 255 counts to approximately 50 counts. FIG. 15 shows a graph of intensity versus angle for the 0.164 second exposure. The dramatic drop in intensity just beyond 0.3 degrees is evident. The valley between 0.34 degrees and 0.42 degrees, missing from the previous exposure, is now adequately characterized. The second, third, and fourth scattering rings (peaks in the intensity versus angle graph) are all on scale in this exposure. Classes inside of approximately 0.3 degrees are overexposed and excluded, and classes outside of approximately 1.5 degrees are underexposed and excluded.

Figure 16:
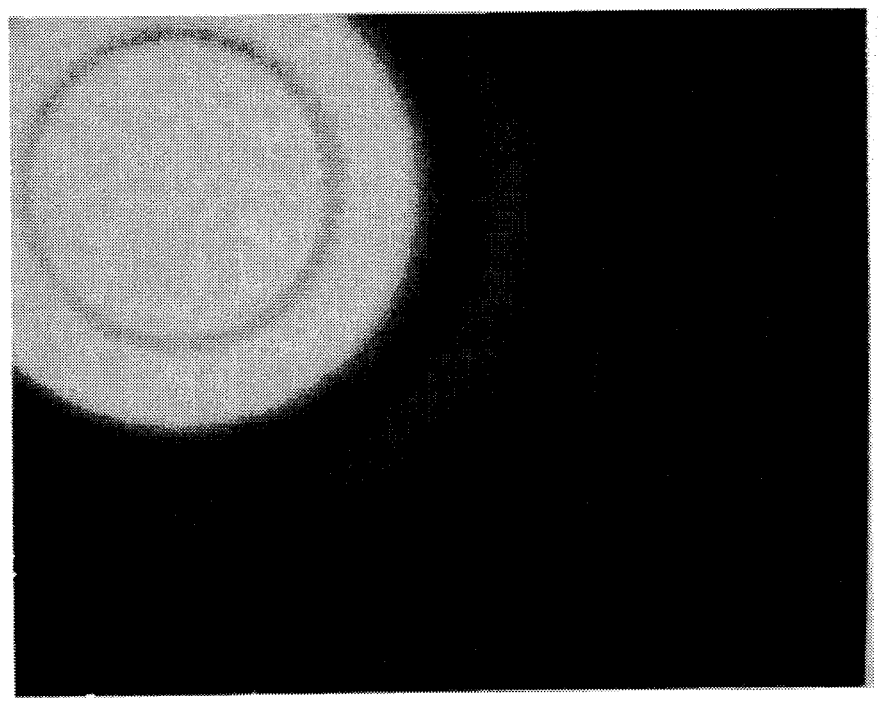
FIG. 16 shows the CCD image of scattered light for an exposure time of 0.655 second.
Figure 18:
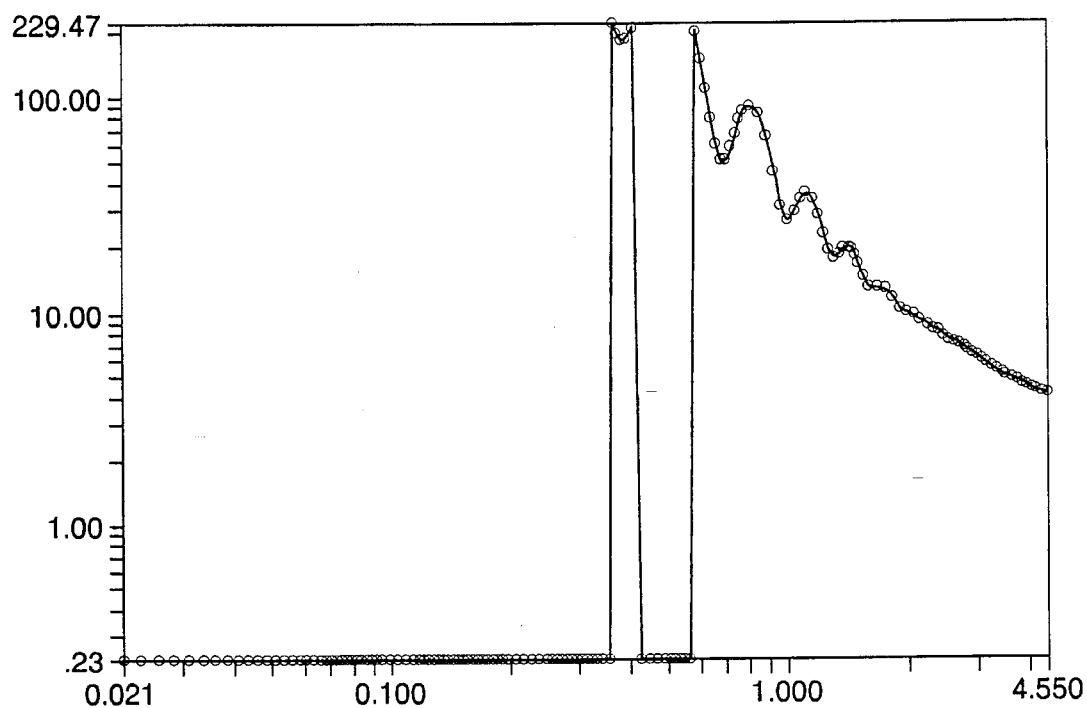
FIG. 18 shows a graph of intensity versus angle for a 0.655 second exposure as obtained by an embodiment of the invention.

FIG. 16 shows the CCD image of light scattered by 108 micrometer diameter polystyrene spheres in water with an exposure time of 0.655 second. For the 0.655 second exposure, a portion of the pixel output values is given by FIG. 17. FIG. 18 shows a graph of intensity versus angle for the 0.655 second exposure. The valley between the first and second rings is on scale, but everything below this and the peak of the second ring is overexposed and excluded. The third through the seventh rings between 0.6 degrees and 2 degrees are on scale.

The next step is to combine the intensity-versus-angle data from multiple exposures into a composite, more complete data set. Intensity values for different exposures must be scaled to account for the differences in exposure time and incident beam intensity. This is done either using predetermined scaling values based on knowledge of exposure time and beam intensity, or by determining an average scaling factor between pairs of exposures to match intensity values for overlapping portions of the valid data range. The latter is done by identifying all classes for which both exposures have valid intensity data, then computing the average ratio between intensities from the two exposures for the corresponding classes. The average is weighted by the product of the number of pixels included in a class for each of the two exposures.

Figure 19:
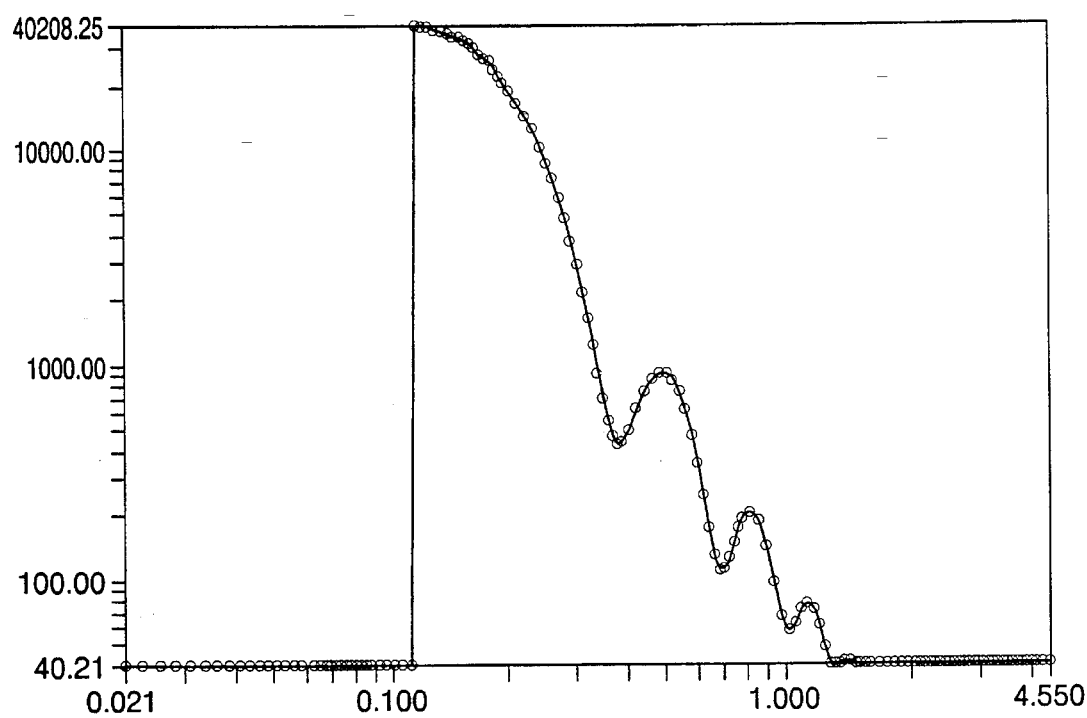
FIG. 19 shows the composite intensity-versus-angle data set from the exposures shown in FIG. 10 through 18.

The composite data set is then produced by multiplying the intensity data for each exposure by that exposure's scaling factor, and averaging all the valid intensity data for an angle class from the different exposures. The average is weighted by the number of pixels contributing from each exposure. FIG. 19 shows the resulting composite data set from the exposures shown in FIG. 10 through 18.

A baseline intensity-versus-angle data set (not shown), derived from exposures taken with no sample particles in the system, is scaled and subtracted from the sample intensity-versus-angle data. This step eliminates intensity data due to the unscattered portion of the light beam and other stray light in the system.

Figure 20:
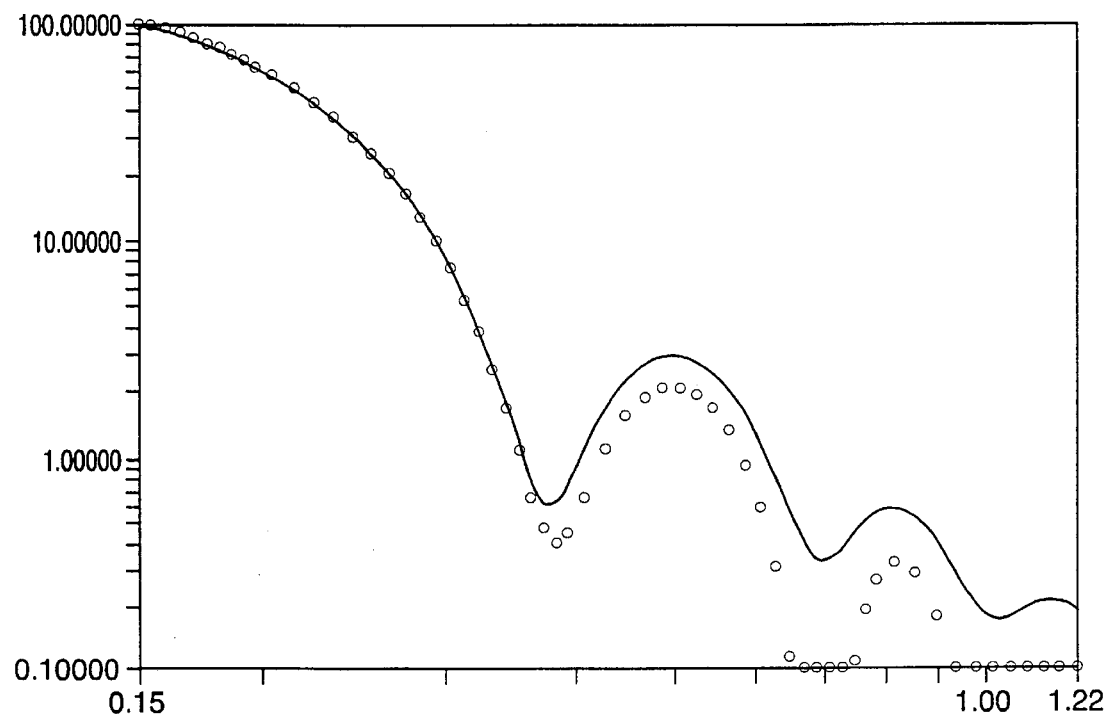
FIG. 20 shows intensity-versus-angle data points as circles and a curve fit to this data using a series of theoretical Mie curves for different size spheres.

Finally, the particle size distribution is determined from the composite intensity-versus-angle data. FIG. 20 shows two sets of data. The intensity-versus-angle points from the composite data set are shown as circles; also shown is the curve representing the non-negative least-squares ("NNLS") fit to this data using a series of theoretical Mie curves for different size spheres.

Figure 21:
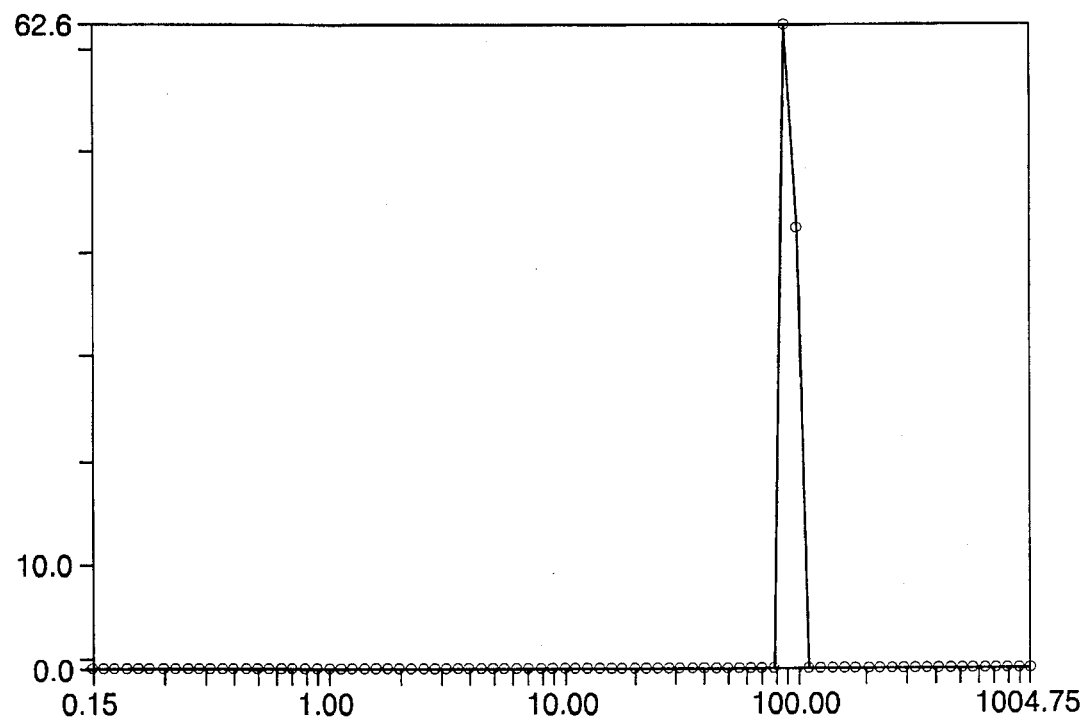
FIG. 21 shows the particle size distribution obtained by an embodiment of the invention for 108 micrometer polystyrene spheres in water.

FIG. 21 shows the particle size distribution obtained by the analyzer for 108 micrometer polystyrene spheres in water. The position of the single peak indicates particles having a size of 108 micrometers.

EXAMPLE 2

Figure 22:
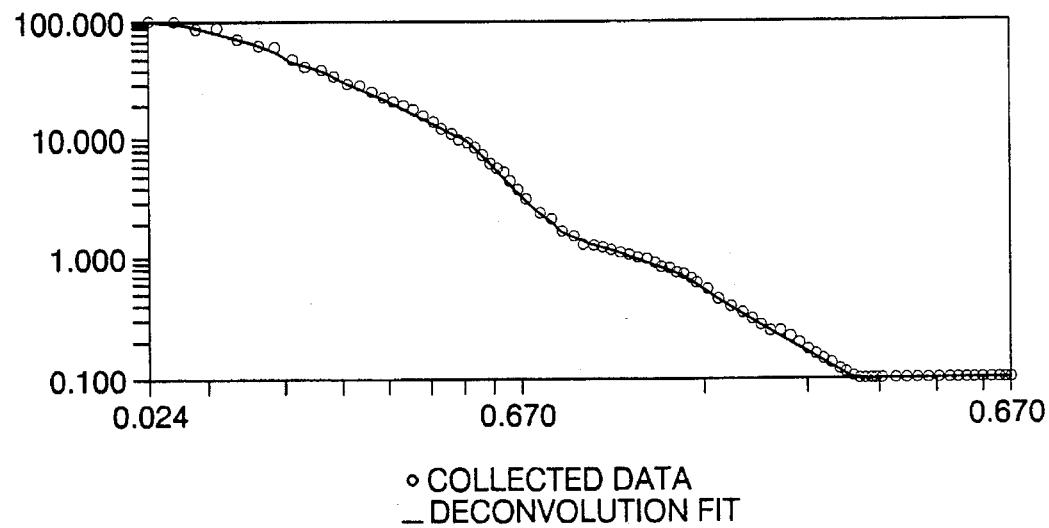
FIG. 22 shows the intensity-versus-angle data obtained by an embodiment of the invention for a mixture of particle sizes.
Figure 23:
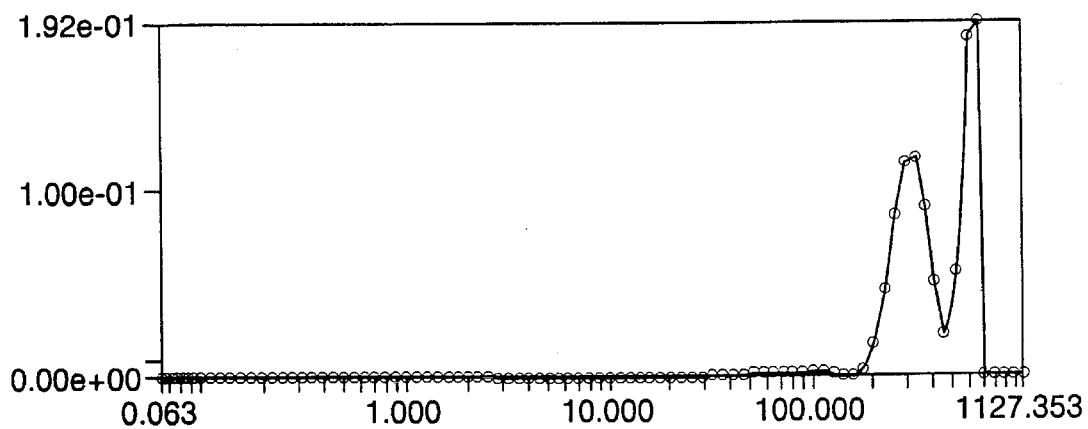
FIG. 23 shows the particle size distribution obtained by an embodiment of the invention for a mixture of particle sizes.

An analysis similar to that described for Example 1 was run for a mixture of polypropylene powder in water. FIG. 22 shows the intensity-versus-angle data and FIG. 23 shows the particle size distribution obtained by the analyzer for this mixture. The position of the two peaks indicates the presence and relative proportions of the two particle sizes of 300 micrometers and 600 micrometers.

Detailed Description of Operation

The sequence of operation described in the above examples is carried out under the control of computer programs residing in the control processor 81, the digital signal processor 71, and the work station 91. In general, the control processor controls all of the mechanical aspects of the analyzer, such as the rotation of the beam assembly 21 and the operation of the fluid circuit 100, and controls the operation of the laser 11 and CCD 51 and the flow of data through the analyzer. The digital signal processor 71 processes all of the data from the CCD 51 to produce intensity-versus-angle data sets. The work station 91 processes the intensity-versus-angle data sets to produce volume fraction versus size data sets (particle size distributions). The operation of the routines which comprise these computer programs is described below.

Certain conventions are used in the description below of the steps carded out during the operation of the routines. Names of procedures implemented by subroutines are indicated by ALL CAPS. Names of program constants or variables that are referred to frequently are defined once and indicated by Initial Caps. Frequently the constant and variable names are RunTogether. Where values are given for program constants, it is assumed the CCD uses a 12-bit analog-to-digital converter.

Certain common geometric and optical functions will be used throughout the remainder of this specification. These functions represent simple transformations involving Snell's Law for the refraction of light and the relation between an angle and the distance subtended by the angle in the focal plane of the lens. These functions and their definitions are as follows:

FluidFromAir(angle)=arcsin(sin(angle)*Nair/Nfluid)

AirFromFluid(angle)=arcsin(sin(angle)*Nfluid/Nair)

DistanceFromAngle(angle,FocalLength)=
    tan(angle)*FocalLength

AngleFromDistance(distance,FocalLength)=arctan(distance/FocalLength)
where:
Nair=refractive index of air=1.00
Nfluid=refractive index of suspending fluid (1.33 for water)

1. CCD and Laser Characterization

A characterization of the CCD and of the laser used in the analyzer provides a way to correct for vagaries in the control or response characteristics of these two components of the analyzer. CCD characterization is performed upon installation of a CCD in an instrument. It defines the response of the particular CCD to differing intensities of light at the wavelength provided by the laser, and to differing integration times. CCD characterization provides the means to interpret CCD data as a linear function of the Total Light Dose delivered during an exposure.

Laser characterization is performed upon installation of a laser or any laser subsystem optical or electronic component, or any change to the operating temperature of the laser. It requires that a valid CCD characterization has previously been completed.

Figure 25A:
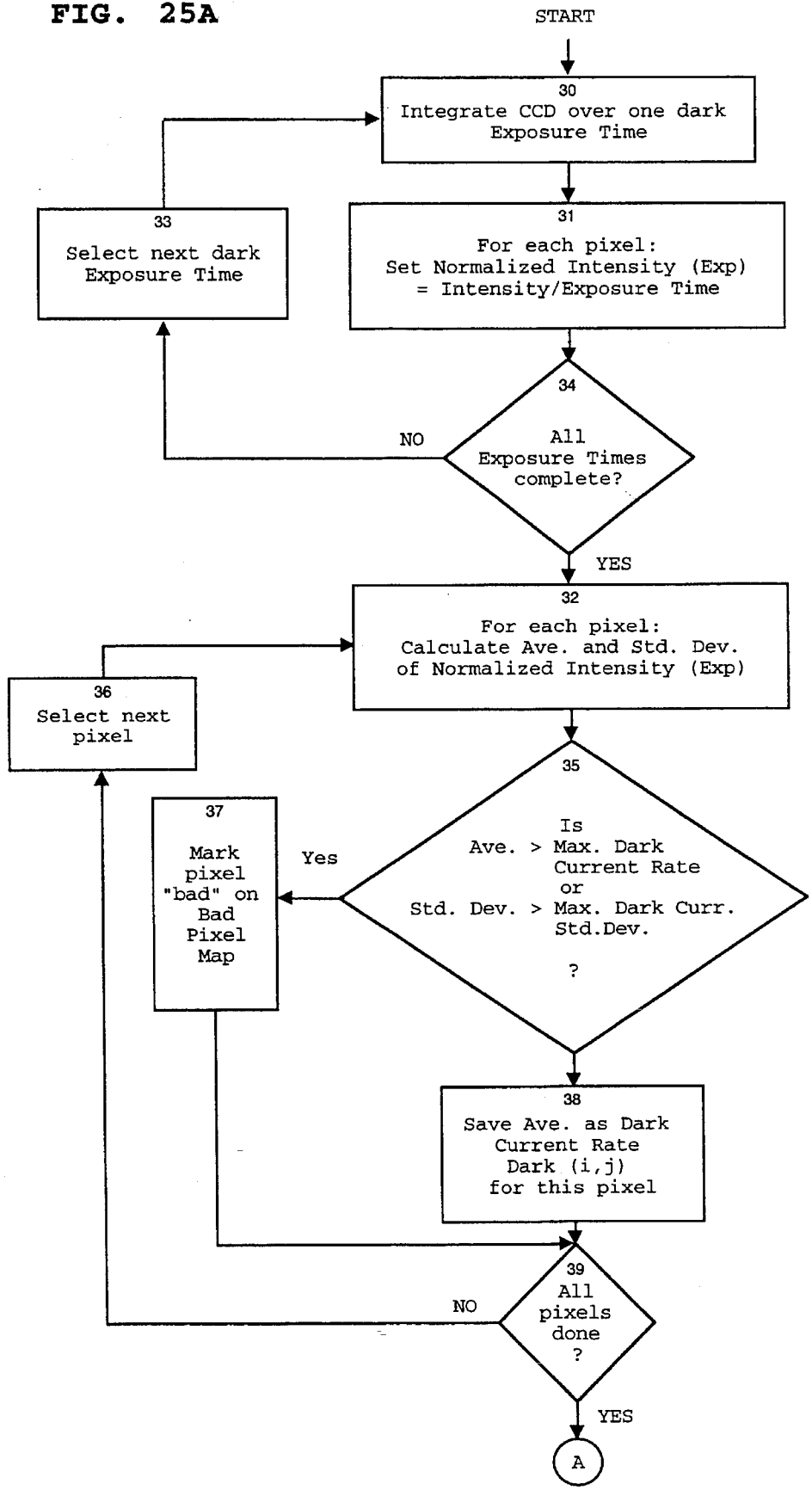
FIGS. 25A, 25B, 25C, and 25D comprise a flow chart for the routine CCD CHARACTERIZATION in an embodiment of the invention.

Routine CCD CHARACTERIZATION is shown in FIGS. 25A–25D. The first step in the routine, shown in blocks 1–10 of FIG. 25A, is to identify bad pixels. Bad pixels are pixels that have a dark current accumulation rate higher than a predetermined limit, or that do not respond linearly to light with sensitivity within a predetermined limit of the average sensitivity of other pixels. Bad pixels are identified during the course of determination of dark current rates and the response and offset of each pixel as described below. Bad pixels are marked in an array in the processor storage referred to as the Bad Pixel Map and are excluded from use in all further analysis.

The analyzer performs its own independent dark current analysis in a subroutine DETERMINE DARK CURRENT RATES (blocks 1–4 of FIG. 25A). Thus, if the CCD in use has columns of dark current pixels, such as columns 1280 to 1295 on the Kodak KAF-1300L, those columns are excluded from use in all operations. To determine the dark current values, the CCD is caused to integrate over each of a set of predetermined Exposure Times (0.1 to 10 seconds) without turning on the laser. As shown in blocks 1–4 of FIG. 25A, for each exposure, the intensity value for each pixel is divided by the Exposure Time to give the normalized intensity for this pixel. As shown in blocks 5–10, when all exposures are complete, the normalized intensity values for all of the exposures are averaged for each pixel and the standard deviation is computed. If the average is greater than the predetermined maximum dark current rate (preferably, about 100 counts/second for a 12-bit analog-to-digital converter), the pixel is marked as bad in the Bad Pixel Map. If the standard deviation is greater than the predetermined maximum dark current standard deviation (preferably, about 5 counts/second), the pixel is marked as bad in the Bad Pixel Map. Otherwise, the average is saved in array Dark[i,j] as the dark current rate for this pixel, where i is the row of the pixel and j is the column of the pixel.

The next step in CCD characterization is to determine the CCD response and offset. The CCD response is determined by measuring the response of each pixel to a uniform light intensity for varying amounts of time, correcting for dark current, and computing the pixel sensitivity to light. For the purpose of reducing requirements for computer memory and computation time, square patches of pixels called N×N pixel areas may be averaged and characterized together.

Figure 25B:
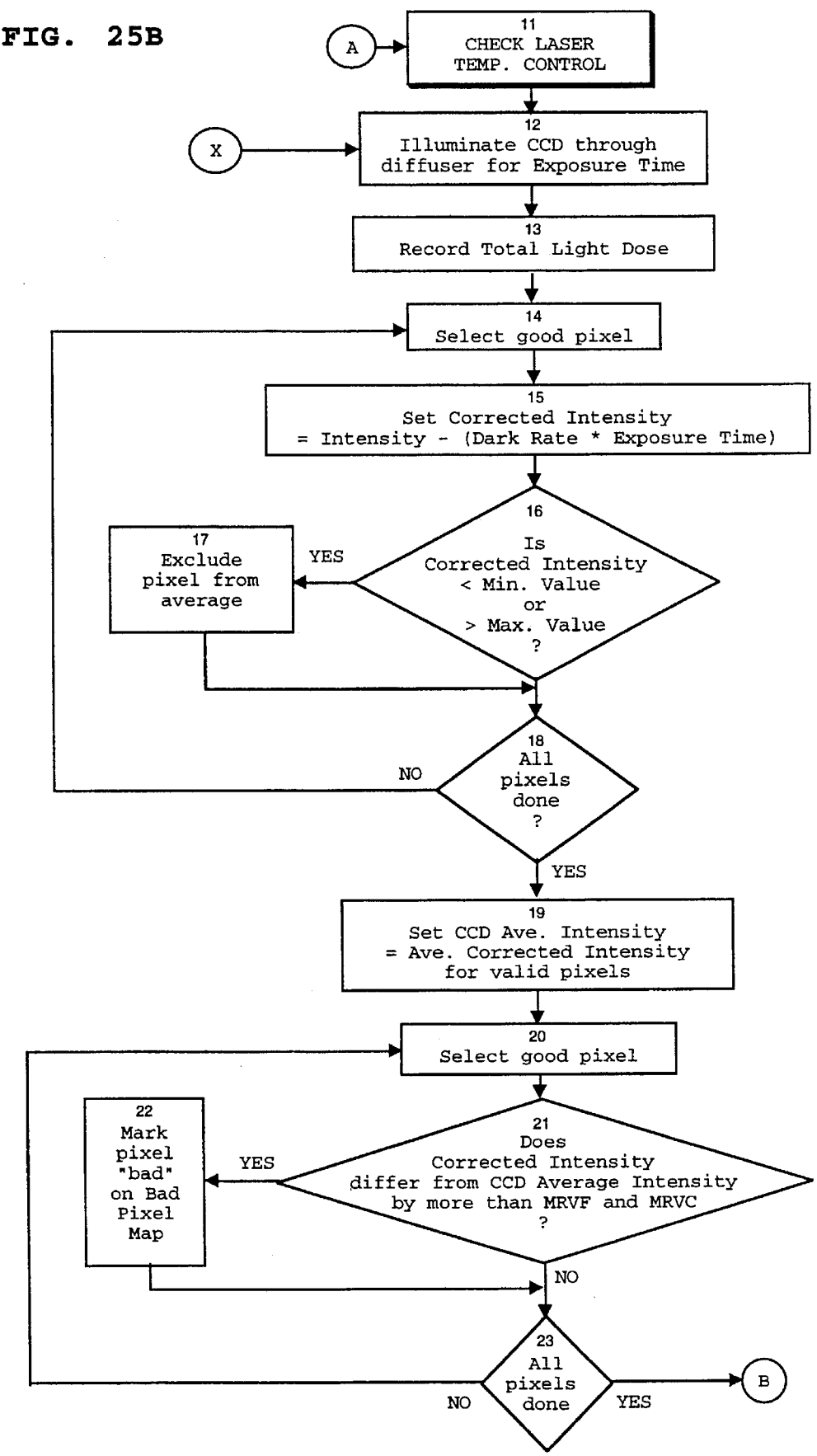
Figure 25C:
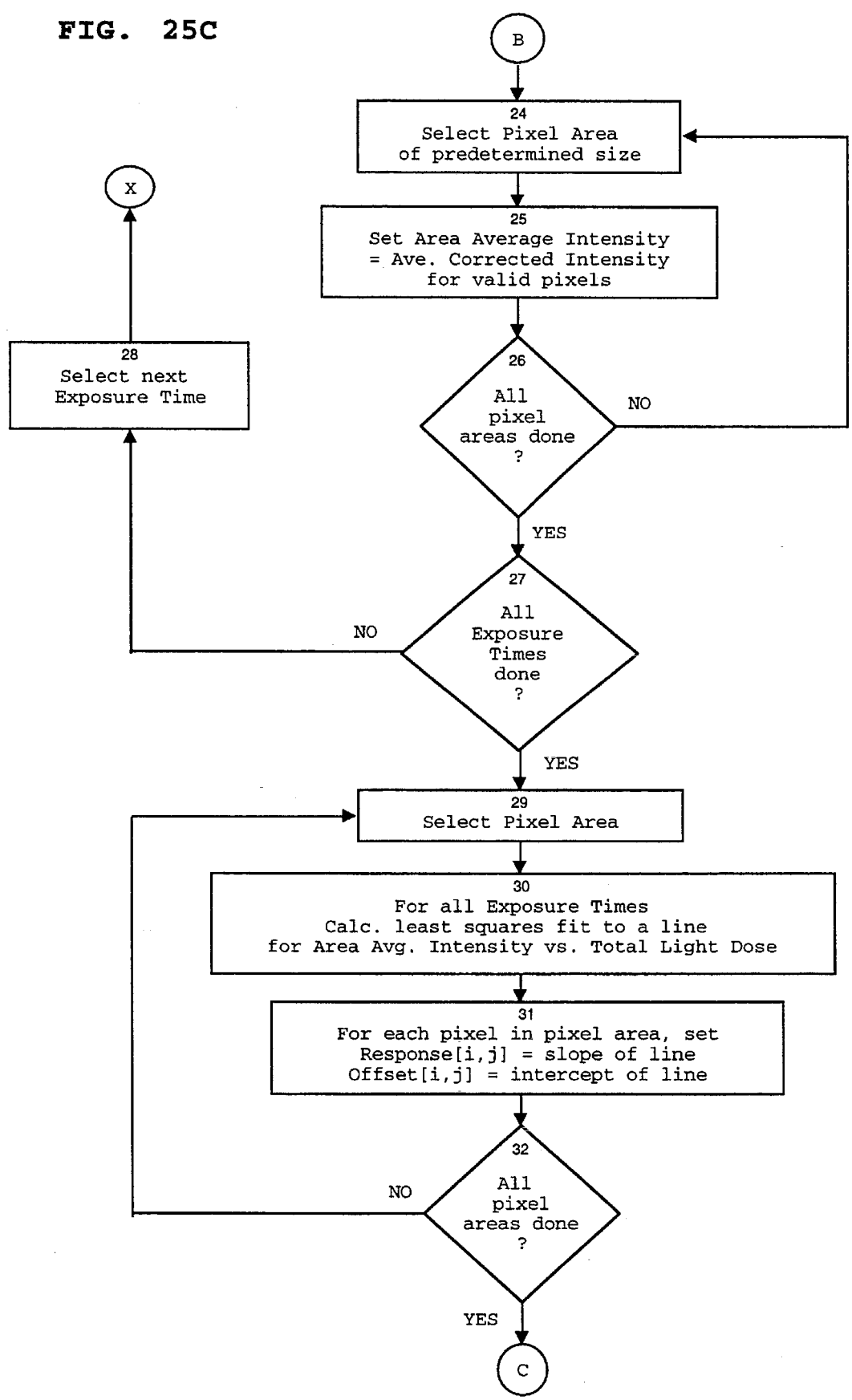
Figure 25D:
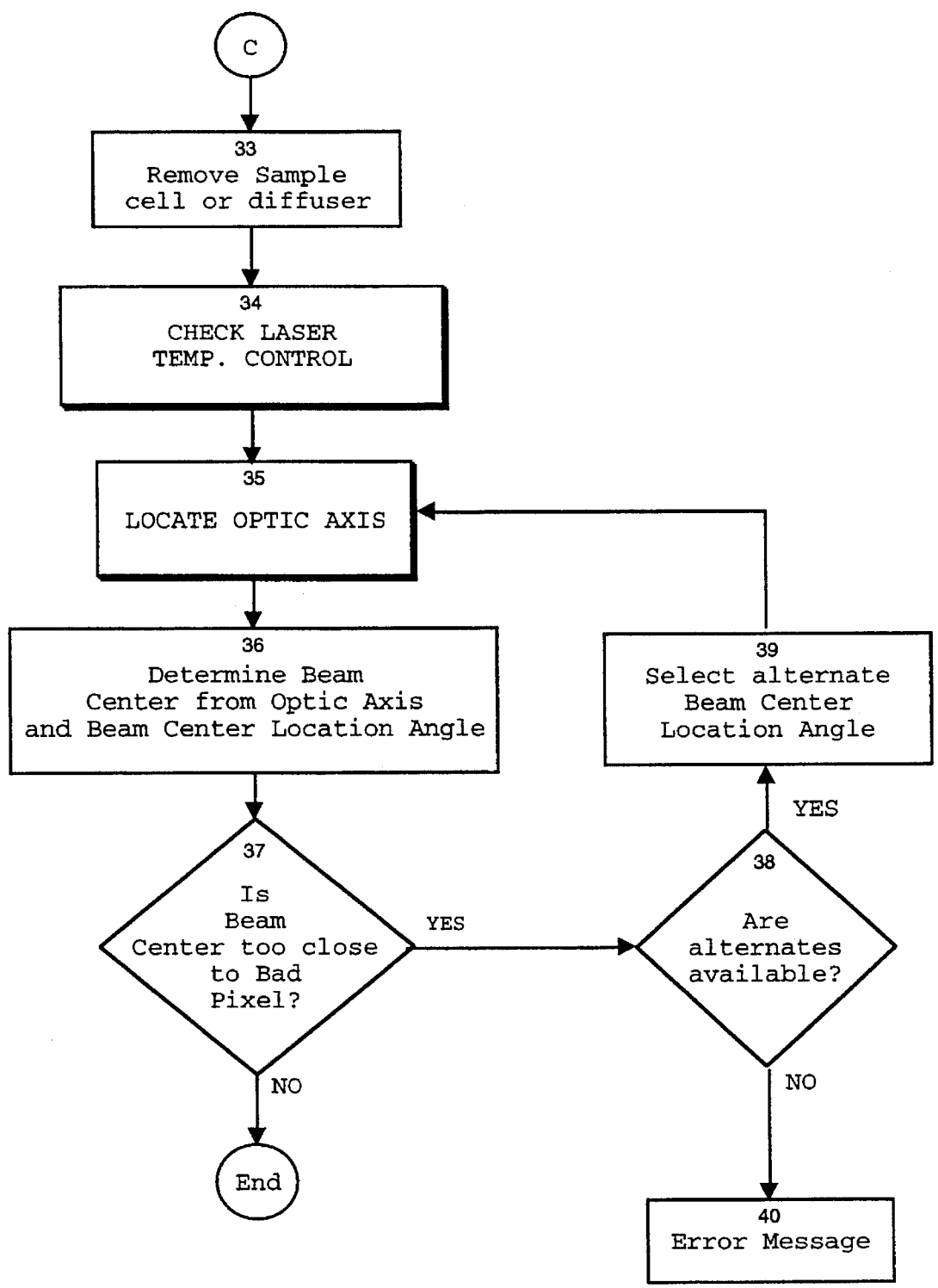

Determining CCD response and offset is shown in blocks 11—32 of FIGS. 25B and 25C. The sample cell 31 is replaced with a uniform diffuser (not shown). The diffuser can be constructed from foam core poster board, covered with an opaque black mask with a 15 mm to 30 mm diameter circular aperture. It scatters all the incident light from the laser so that the light exiting the diffuser is of approximately equal intensity (within 0.1%) at all angles captured by the field lens and focused on the CCD. This causes all pixels on the CCD receive approximately equal light intensities.

The subroutine CHECK LASER TEMPERATURE CONTROL is executed at block 11. This subroutine is described below. The laser is rotated to the nominal Beam Center Location Angle. The nominal Beam Center Location Angle is chosen so that, in the absence of the diffuser, (1) the unscattered beam 32 will strike the CCD, (2) the primary reflected light from the CCD is directed away from the field lens and into a light trap (not shown), and (3) light scattered at angles from 0 degrees to at least 4.7 degrees will fall on the CCD. The nominal Beam Center Location Angle is preferably a negative angle of 4.6 degrees with respect to the optic axis. The laser is set to the maximum analysis Laser Drive Current. The CCD is exposed to the laser for a predetermined series of Exposures Times. The Exposure Times are chosen such that the range of usable pixel intensity values is adequately covered. For each exposure, the Total Light Dose administered and the Exposure Time are recorded. For each pixel not marked as bad, if the pixel intensity value is below the predetermined minimum raw pixel value (4 to 16 for a 12-bit analog-to-digital converter) or above the maximum raw pixel value (4094 for a 12-bit analog-to-digital converter), this reading is invalid and excluded from use in subsequent average calculations. Whether invalidated or not, the dark current rate for this pixel multiplied by the Exposure Time, is subtracted from the intensity reading and the difference is kept as the corrected intensity for this pixel.

The average corrected intensity is computed for all pixels with valid corrected intensities for this exposure, and the result is kept as the CCD average intensity for this exposure.

As shown in blocks 20–23, another loop is executed through all of the pixels. For each pixel not marked as bad, if the corrected intensity value (whether valid or invalid) is different from the CCD average intensity by more than the predetermined maximum response variation factor ("MRVF", 0.1 to 0.5) and by more than the predetermined maximum response variation counts ("MRVC", 1 to 5 counts), the pixel is marked as bad in the Bad Pixel Map.

As shown in blocks 24–28, for each N×N pixel area, where N (1 to 4 pixels) is the predetermined CCD response pixel area size, the average corrected intensity is computed for all pixels in the area with valid corrected intensities, and is kept as the area average intensity for this pixel area and for this exposure.

As shown in blocks 29–32, when all exposures are complete, for each pixel area, the slope and intercept of a line are computed from a least squares fit to the data for area average intensity versus Total Light Dose. For each pixel in the pixel area, the slope and intercept of the line is kept as the Response[i,j] and Offset[i,j], respectively, of the CCD for the pixel at row i and column j.

This completes determination of the CCD response and offset. At this point the laser is located at the nominal Beam Center Location Angle. The next step is to determine the actual Beam Center Location Angle, as shown in blocks 33–40 of FIG. 25D.

To determine the Beam Center Location Angle, the sample cell or diffuser, if either is present, is removed. The subroutine CHECK LASER TEMPERATURE CONTROL is executed. Optic Axis (as distinguished by initial caps from "optic axis") is the point where the optic axis of the field lens 41 intersects the CCD. The Optic Axis is nominally at the same location as the focal point of the field lens 41, although for any location subtending less than 4 degrees at the optic center of the field lens 41, 90% of the pixels will be correctly assigned for every angle class. The subroutine LOCATE OPTIC AXIS is executed. The coordinates of Beam Center (Bx,By) are determined from the coordinates of the Optic Axis (Ox,Oy) and the current Beam Center Location Angle as follows:

Bx=Ox−DistanceFromAngle(BeamCenter-
  LocationAngle,FocalLength)/PixelWidth

By=Oy

The Bad Pixel Map is checked for any bad pixels too close to Beam Center by scanning the rectangle of pixels within minimum bad pixel to beam center distance rows and columns of Beam Center. The minimum bad pixel to beam center distance is a predefined program constant, typically 32 pixels. If any bad pixels are found, the steps shown in blocks 35–37 are repeated with other possible Beam Center Location Angles, starting at the nominal Beam Center Location Angle and alternately checking smaller and larger angles varying by the minimum settable beam angle increment (a program constant, preferably 0.01 degrees), until a Beam Center Location Angle is found with no bad pixels within the minimum bad pixel to beam center distance of Beam Center. If no such angle is found between the minimum Beam Center Location Angle and the maximum Beam Center Location Angle, an error condition, "Unable to Locate Valid Beam Center Location Angle," is reported. Both the minimum Beam Center Location Angle and the maximum Beam Center Location Angle, program constants, are chosen so that the three conditions specified above for the nominal Beam Center Location Angle are met.

Subroutine CHECK LASER TEMPERATURE CONTROL (not shown) is called above, and is executed at any time that the laser is to be used. This subroutine checks the laser temperature sensor 13. The sensor is on if the laser temperature is within an acceptable range, preferably within 0.1 degrees, of the predetermined laser operating temperature (between 50 and 70 degrees Fahrenheit for the Toshiba model TOLD 9140). If the sensor is off, a laser temperature error is indicated. Checking continues until the sensor is on, then processing returns to the calling routine.

This completes the process to determine Beam Center Location Angle and routine CCD CHARACTERIZATION. The next step is to execute the routine LASER CHARACTERIZATION.

Figure 26:
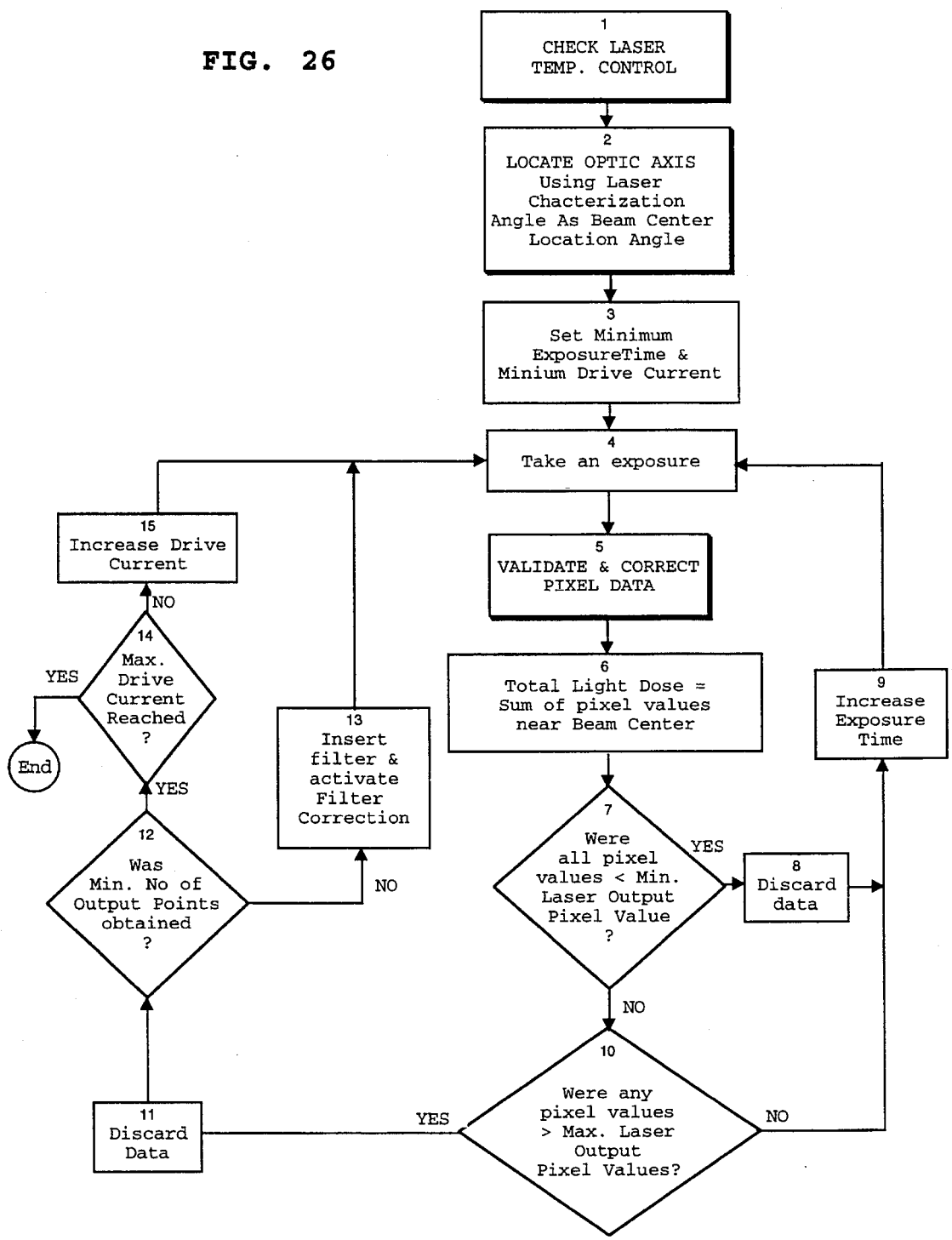
FIG. 26 is a flow chart for the routine LASER CHARACTERIZATION in an embodiment of the invention.

Routine LASER CHARACTERIZATION is shown in FIG. 26. This routine characterizes laser output versus drive current and time. The sample cell and/or diffuser are removed from the system, and a beam expander lens (not shown) is inserted at the location of the sample cell. The beam expander lens is an additional lens, which causes a slight defocusing of the collimated beam at the CCD, so that its diameter is approximately 50% of the width of the CCD (or approximately 8 mm.). This allows a more accurate quantification of the total beam intensity using the CCD. Subroutine CHECK LASER TEMPERATURE CONTROL is executed, followed by the subroutine LOCATE OPTIC AXIS (FIG. 3.1) using the laser characterization angle (about negative 2.3 degrees) as the Beam Center Location Angle. Starting with the minimum settable laser drive current (a program constant, about 0.1 milliamp) and increasing by the minimum settable laser drive current increment (a program constant, preferably about 0.1 milliamp), the laser intensity is determined as a function of Exposure Time for a given Laser Drive Current as follows:

As shown by blocks 4–15 of FIG. 26 for each Exposure Time from the minimum Exposure Time (a program constant, about 1 microsecond) to the maximum Exposure Time (a program constant, about 10 seconds), take an exposure, call subroutine VALIDATE AND CORRECT PIXEL DATA (FIG. 2.1), and sum the pixel values in the rectangle centered on Beam Center and including all pixels within the laser output quantification distance of Beam Center (a program constant, about 256 to 384 pixels). Save this sum as the Total Light Dose for the specified Laser Drive Current and Exposure Time. Discard data points having no pixel values above the minimum laser output pixel value (a program constant, 4 to 16 counts), and data points having any pixel values above the maximum laser output pixel value (a program constant, about 4094 counts). Terminate data collection for a Laser Drive Current when an exposure is taken having a pixel value in the rectangle which exceeds the maximum laser output pixel value.

When a Laser Drive Current is reached for which the minimum number of laser output points (a program constant, 3 to 5 points) cannot be taken due to exceeding the maximum laser output pixel value, insert a neutral density filter (not shown) into the optical path. A filter correction scaling factor may be computed by repeating data collection for an earlier Laser Drive Current having enough valid data points and calculating the least squares fit of Total Light Dose versus Exposure Time for each of the two data sets for this Laser Drive Current and taking the ratio of the two slopes. Other methods of determining a filter correction scaling factor will be apparent to those skilled in the art. Scale all data taken with this filter by its filter correction. Continue as before with successively higher Laser Drive Currents until the maximum Laser Drive Current is reached. If necessary, substitute additional successively optically denser filters (not shown) as above and obtain and use the filter correction for each to scale data. This completes the determination of Laser Intensity as a function of Exposure Time and Laser Drive Current.

The Total Light Dose values associated with each Laser Drive Current and Exposure Time may be kept individually in a table for use in scaling data taken at the same current and time. Alternatively, the data may be fit to a function or to a series of functions and those functions may be used to compute Total Light Dose for any Laser Drive Current and Exposure Time. This completes routine LASER CHARACTERIZATION.

2. Process Raw Pixel Data

Raw pixel data is received by the digital signal processor 71 from the CCD at completion of any exposure. Several subroutines, described below, are used to process raw pixel data at various points in the process. In the following, "pixel[i,j]" refers to the pixel at row i, column j of the CCD, and "Pixel[i,j]" refers to the numerical data received from pixel[i,j].

Figure 27:
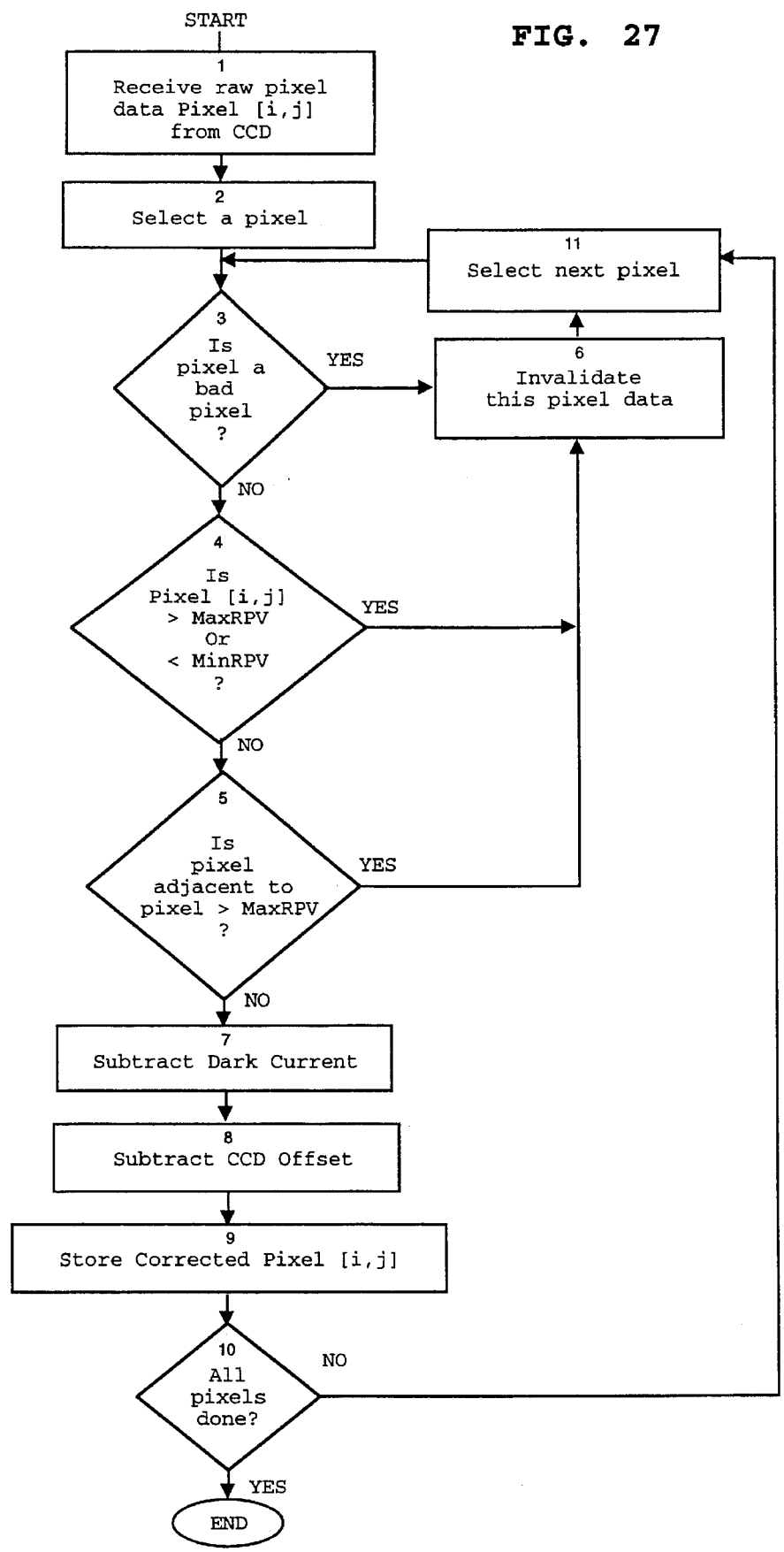
FIG. 27 is a flow chart for the routine VALIDATE AND CORRECT PIXEL DATA in an embodiment of the invention.

The subroutine VALIDATE AND CORRECT PIXEL DATA is shown in FIG. 27. For the raw data Pixel[i,j], if pixel[i,j] is marked on the Bad Pixel Map, the pixel data is invalidated. If the value of Pixel[i,j] is above the predetermined maximum raw pixel value (about 4094 counts), the pixel data is invalidated and processing continues with the next pixel. If the value of Pixel[i,j] is below the predetermined minimum raw pixel value (4 to 16 counts), the pixel data is invalidated and, as shown in block 11, processing continues with the next pixel. If pixel[i,j] is adjacent to a pixel whose raw data value is greater than the maximum raw pixel value, the pixel data Pixel[i,j] is invalidated and processing continues with the next pixel. The 8 nearest neighbors of pixel[i,j] are considered adjacent.

If the pixel is not bad, the dark current is subtracted as shown in block 7 for this pixel based on exposure time and the CCD Offset:

Pixel[i,j]=Pixel[i,j]−Dark[i,j]×ExposureTime−Offset[i,j].

Processing continues with the next pixel. Completion of all the pixels completes the subroutine VALIDATE AND CORRECT PIXEL DATA.

The subroutine SCALE PIXEL DATA BY TOTAL LIGHT DOSE (not shown) normalizes the pixel data to account for differences in laser drive currents and exposure times. For each pixel with valid data, each pixel value is divided by the Total Light Dose for this exposure as determined in block 6 of FIG. 26 and processing returns to the calling routine.

The subroutine ADD PIXEL DATA TO AGGREGATE PIXEL DATA (not shown) combines pixel data from different exposures and keeps track of the number of exposures. For each pixel[i,j] with valid data, Pixel[i,j] is added to AggregatePixelData[i,j] an array to sum Pixel[i,j] values for multiple exposures. AggregatePixelExposureCount[i,j] an array to record a count of the number of exposures, is incremented by 1 and processing returns to the calling routine.

The subroutine CORRECT AGGREGATE PIXEL DATA (not shown) adjusts the pixel data to conform to the linear form determined during CCD Characterization. For each AggregatePixelData[i,j], the following computation is made CorrectedAggregatePixelData[i,j]=AggregatePixelData[i,j]/Response[i,j]

and processing returns to the calling routine.

3. Measure Beam Intensity and Alignment

Figure 28:
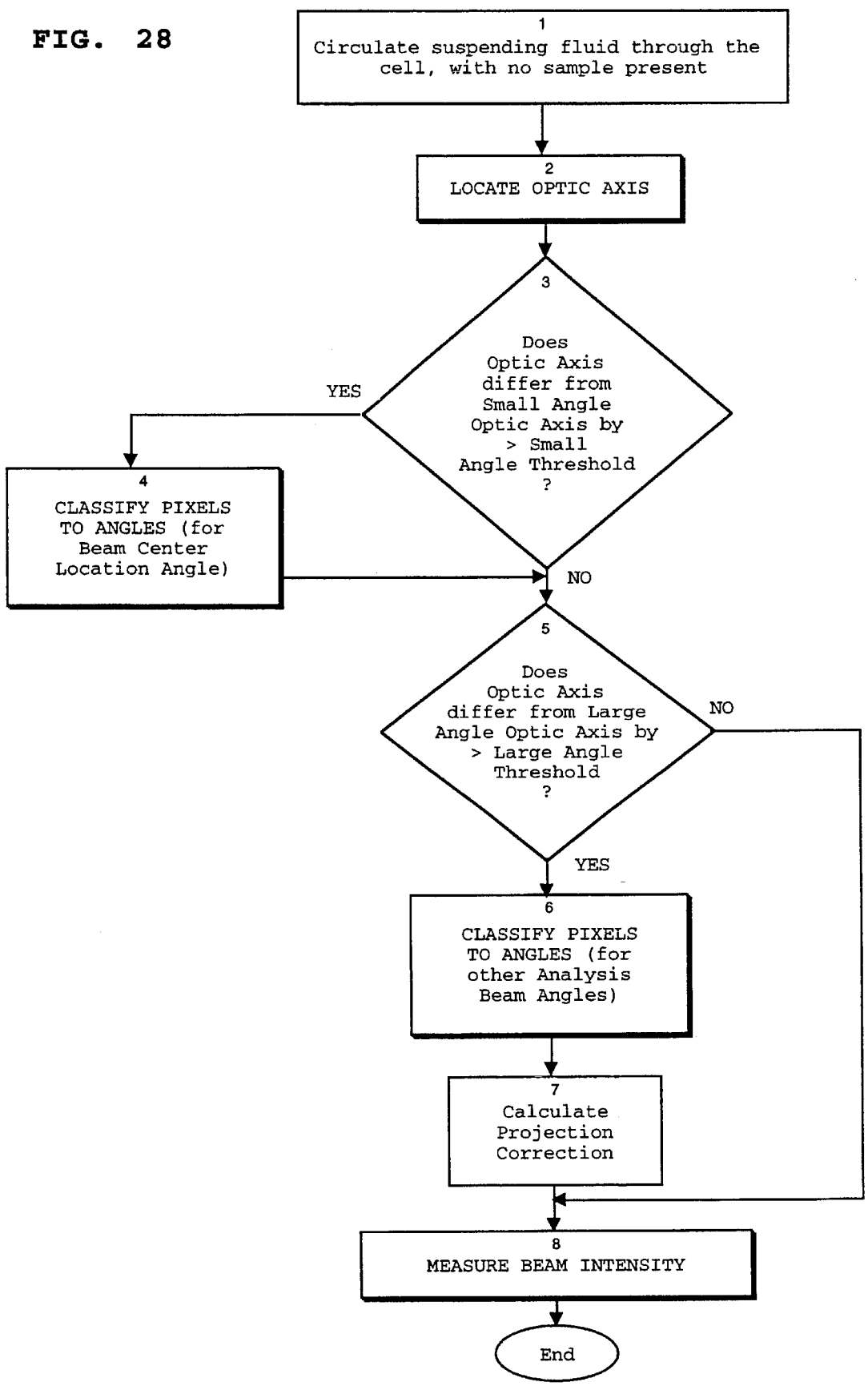
FIG. 28 is a flow chart for the routine MEASURE BEAM INTENSITY AND ALIGNMENT in an embodiment of the invention.

Several routines are provided to measure the intensity of the light source beam and to calibrate its alignment relative to the optic axis of the lens. As shown in FIG. 28, to calibrate the location of the optic axis, suspending fluid is circulated through the cell, with no sample present. Subroutine LOCATE OPTIC AXIS is executed. As shown in blocks 3 and 4 of FIG. 28, if the newly computed Optic Axis differs from the currently saved small angle Optic Axis by more than the predetermined small angle Optic Axis threshold (0.1 to 1 pixel), subroutine CLASSIFY PIXELS TO ANGLE CLASSES is executed for the Beam Center Location Angle. As shown in blocks 5–7, if the newly computed Optic Axis differs from the currently saved large angle Optic Axis by more than the predetermined large angle Optic Axis threshold (0.5 to 5 pixels), subroutine CLASSIFY PIXELS TO ANGLE is executed for all other analysis Beam Angles, and subroutine CALCULATE PROJECTION CORRECTION (described below) is called. To measure the intensity of the light source beam, subroutine MEASURE BEAM INTENSITY (described below) is called.

Figure 29A:
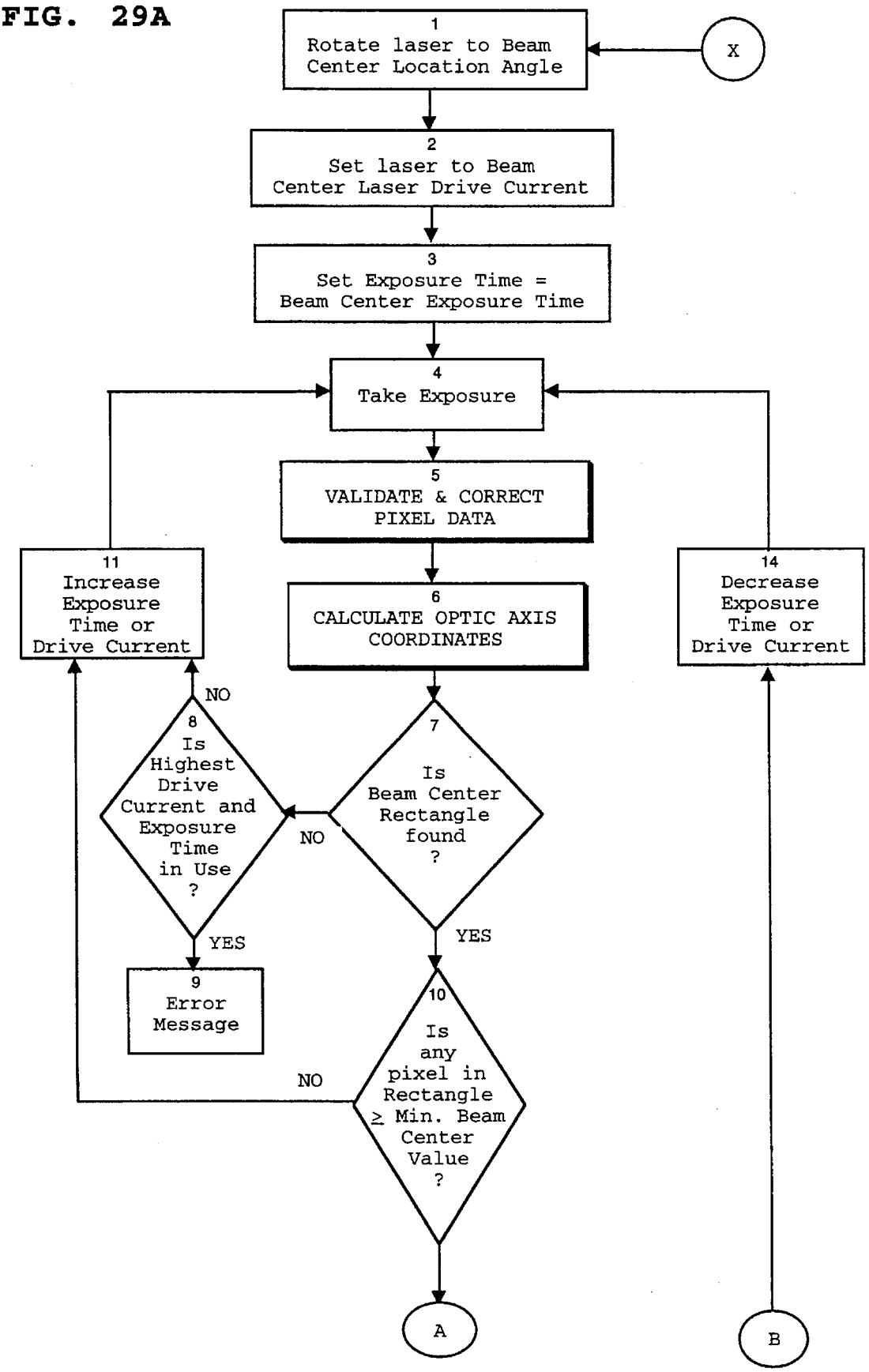

Subroutine LOCATE OPTIC AXIS is shown in FIG. 29A and 29B. The steps of this subroutine are as follows: Rotate the laser to the Beam Center Location Angle. As shown in blocks 2–4 of FIG. 29A, take an exposure at the last recorded beam center Laser Drive Current and beam center Exposure Time. For a new system, these are the default beam center Laser Drive Current (preferably, 4 to 7 milliamps), and the default beam center Exposure Time (preferably, about 10 microseconds). Call subroutine VALIDATE AND CORRECT PIXEL DATA. Call subroutine CALCULATE OPTIC AXIS COORDINATES (FIG. 30). Retain the pixel data from the beam center rectangle located in this process.

As shown in blocks 7 and 8, if no beam center rectangle is found or if no pixel value in the beam center rectangle is greater than or equal to the predetermined minimum beam center value (1000 to 2000 for a 12 bit A/D converter), change to the next higher analysis Exposure Time and repeat from block 4. If the next higher analysis Exposure Time is above the maximum beam center Exposure Time (preferably, about 100 microseconds), use the next higher analysis Laser Drive Current and the default beam center Exposure Time. If the highest analysis Laser Drive Current was already in use, indicate a "Beam Detection Underrange Error" and end the procedure.

As shown in blocks 12–14 of FIGS. 29A and 29B, if any pixel in the beam center rectangle has a data value above the predetermined maximum beam center value (3000 to 4094 for 12 bit A/D converter), change to the next lower analysis Exposure Time and repeat from block 4. If the lowest analysis Exposure Time was already in use, use the next lower analysis Laser Drive Current and the default beam center Exposure Time. If the lowest analysis Laser Drive Current was already in use, indicate a "Beam Detection Overrange Error" and end the procedure.

Continue until the maximum pixel value in the beam center rectangle is between the minimum Beam Center value and the maximum Beam Center value. If the new Optic Axis x coordinate (NewOx) differs from the previous value (OldOx) by more than the maximum Optic Axis x deviation (a program constant, 1 to 3 pixels), compute the corresponding angular displacement A=AngleFromDistance((NewOx−OldOx)×PixelWidth, FocalLength), correct the Beam Angle by adding A to the current rotation position, and repeat the subroutine from the beginning. Otherwise, record the current Laser Drive Current and Exposure Time as the beam center Laser Drive Current and the beam center Exposure Time. This completes subroutine LOCATE OPTIC AXIS; processing returns to the calling routine.

Subroutine CALCULATE OPTIC AXIS COORDINATES is shown in FIG. 30. The steps of this routine are as follows: Scan the rows and columns of pixels, and determine the boundaries of the minimum rectangle containing all pixels with values above the Beam Center threshold (preferably, 500 to 1000 counts). Compute the weighted average of the coordinates of the pixels in the rectangle, where the coordinates of the pixel at row i, column j are (i+0.5, j+0.5), and the weighting factor for each pixel is the square of the pixel intensity value. The weighted average column or y coordinate is the y coordinate of Optic Axis, Oy. The weighted average row or x coordinate is corrected for the Beam Center Location Angle and pixel width to produce the x coordinate of Optic Axis, Ox:

Ox=AverageRow+DistanceFromAngle(BeamCenterLocationAngle, FocalLength)/PixelWidth This completes subroutine CALCULATE OPTIC AXIS; processing returns to the calling routine.

Figure 31:
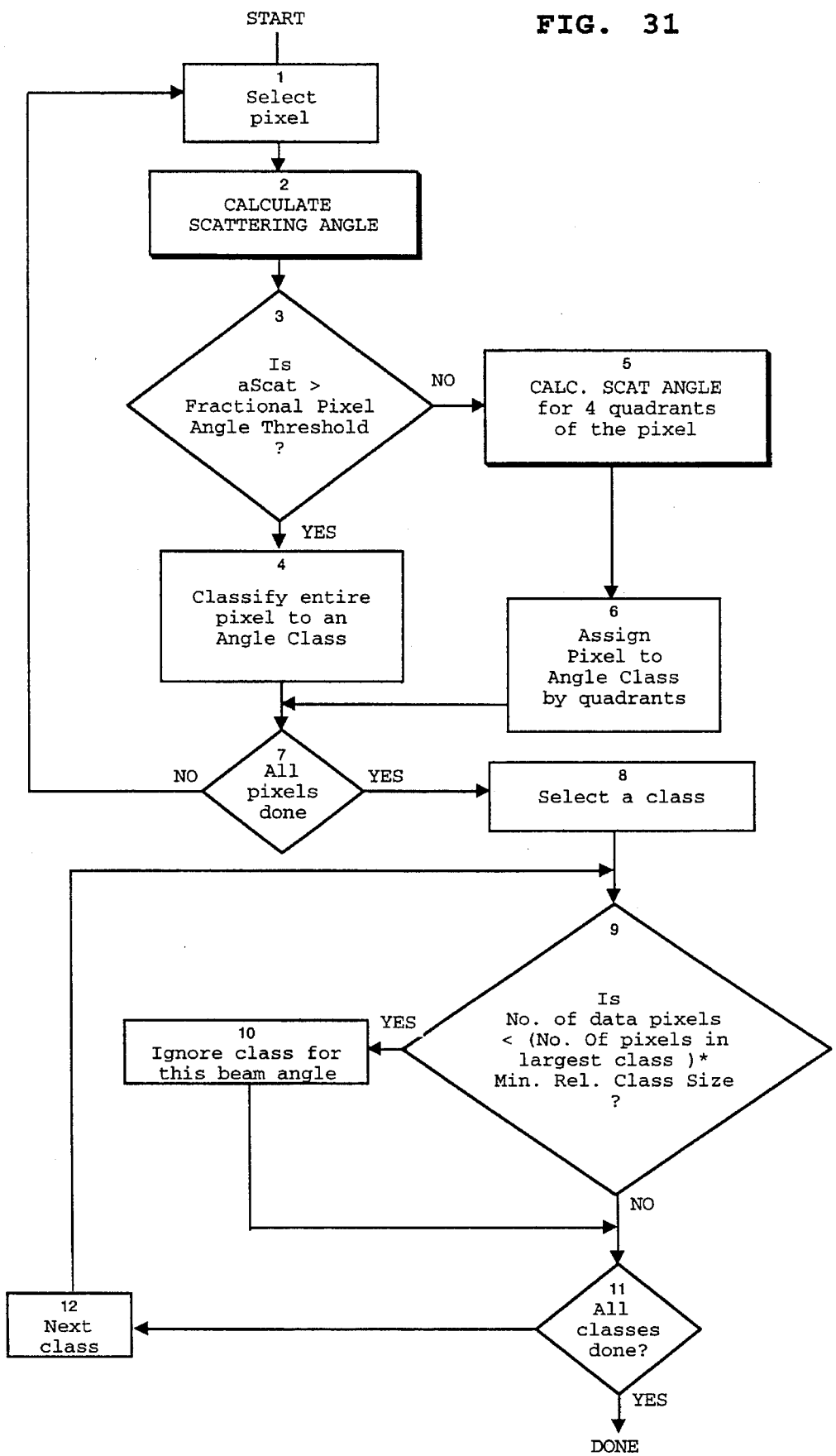
FIG. 31 is a flow chart for the routine CLASSIFY PIXELS TO ANGLE CLASSES FOR A BEAM ANGLE in an embodiment of the invention.

Subroutine CLASSIFY PIXELS TO ANGLE FOR A BEAM ANGLE is shown in FIG. 31. Scattering angle classes are intervals between fixed scattering angles. All light scattered at angles within one angle interval is treated as light scattered at the corresponding angle class. This is a means of treating the continuous phenomenon of scattering intensity versus angle as a discrete problem of scattering intensity-versus-angle class. Angle classes may cover variable intervals, such as varying in width from 0.0025 degrees for very small angles (less than 0.1 degrees), increasing in width for larger angles up to a width of 0.1 degrees for the largest angles (greater than 3.2 degrees). One example of angle classes is given by the following table:

Table Of Angle Classes

| Angular Resolution (degrees) | Angle Range (degrees) | Number of Angles |
| --- | --- | --- |
| 0.0025 | 0.0–0.1 | 40 |
| 0.005 | 0.1–0.2 | 20 |
| 0.01 | 0.2–0.4 | 20 |
| 0.02 | 0.4–0.8 | 20 |
| 0.04 | 0.8–1.6 | 20 |
| 0.08 | 1.6–3.2 | 20 |
| 0.1 | 3.2–180 | 10/degree |

Each pixel of the CCD is assigned to a scattering angle class based on the angle at which the incident light beam must be scattered in the cell to strike the pixel. Thus, a re-assignment of the pixel must be done for any change in the geometric configuration of the lens or the CCD and at any time the Beam Angle changes. To achieve higher resolution at small angles, fractions of pixel area are assigned to different angle classes when an angle class boundary falls across the pixel. The scattering angle classes are arranged in an array according to increasing angle. Pixels in an angle class are contiguous in the sense that nearest neighbors of a pixel are in the same angle class until a class boundary 54 is reached. Assignment of a pixel to an angle class is signified by the corresponding index into the single-dimensional angle class arrays; this index is stored in a two-dimensional pixel-to-angle-class array InClass.

For a given Beam Angle, InClass[i,j] will contain the index of the smallest scattering angle class to which any portion of pixel[i,j]'s area is assigned. The pixel-fraction-in-class array InFrac[i,j] will contain the fraction of the total area of pixel[i,j] which is assigned to that angle class. The remainder of pixel[i,j]'s area is assigned to the next larger scattering angle class. NormClass[m] is an array associated with the scattering angle classes used to count the number of pixels included in each class.

In the following, the row and column coordinates i and j are taken to be the coordinates of the lower left corner of pixel[i,j] as seen facing the CCD from the direction of the field lens and sample cell. The arrays InClass, InFrac, and NormClass are set to zero. As shown in blocks 1 and 2 of FIG. 31, for each pixel[i,j] not marked in the Bad Pixel Map, subroutine CALCULATE SCATTERING ANGLE (FIG. 32, described below) is called for the pixel's center coordinates, (i+0.5, j+0.5). If the scattering angle is greater that the predetermined fractional pixel angle threshold (preferably, 0.2 to 0.8 degrees), the class-indication index m is set to the index of the smallest angle class whose upper limit is greater than or equal to the scattering angle.
Set InClass[i,j]=m.
Set InFrac[i,j]=1.
Add 1 to NormClass[m].

As shown in blocks 3, 5, and 6, if the scattering angle is less than or equal to the fractional pixel angle threshold, subroutine CALCULATE SCATTERING ANGLE is called for the center coordinates of each of the pixel's quadrants, (i+0.25, j+0.25), (i+0.25, j+0.75), (i+0.75, j+0.25), and (i+0.75, j+0 75). Index m is set to the index of the smallest angle class whose upper limit is greater than or equal to the minimum of the four scattering angles:

1. Set InClass[i,j]=m.
2. For each of the four quadrant scattering angles, if the scattering angle is smaller than the upper limit for class m, add 0.25 to InFrac[i,j].
3. Add InFrac[i,j] to NormClass[m].
4. Add 1−InFrac[i,j] to NormClass[m+1].

As shown in blocks 9–12, when assignment of pixels is completed, pixel assignments are removed if they are to classes that contain only a small number of pixels near the edge of the CCD (not including the small angle classes near Beam Center at the Beam Center Location Angle). These classes will have better data at the next larger Beam Angle. The array NormClass is inspected to determine the angle class mMax containing the maximum number of pixels assigned to any class. For each angle class m (if the given Beam Angle is the Beam Center Location Angle, only classes with index m greater than mMax are tested), if NormClass[m]<(NormClass[mMax]*MinimumRelativeClassSize)

then each pixel[i,j] assigned to class m is deassigned so that it is assigned to no class:
InClass[i,j]=<INVALID>
NormClass[m]=0.

The value for the minimum relative class size is a program constant, preferably between 0.2 and 0.5. This completes subroutine CLASSIFICATION OF PIXELS TO ANGLES for a Beam Angle; processing returns to the calling routine.

Subroutine CALCULATE PROJECTION CORRECTION (not shown) corrects for the reduction in intensity at each pixel of the CCD where the pixel is not located at a distance from the optic center of the lens equal to the focal length of the lens or is not in an area perpendicular to the line connecting the pixel with the optic center of the lens. For the former correction, for each pixel, the correction is calculated for projection of intensity from a sphere of radius Focal-Length to the focal plane:

Ox=x or row coordinate of Optic Axis

Oy=y or column coordinate of Optic Axis

PixelWidth=pixel width in mm

PixelHeight=pixel height in mm

R=distance from center of pixel to Optic Axis in mm=$(((i+0.5-Ox)\times PixelWidth)^2+((j+0.5-Oy)\times PixelHeight)^2)^{1/2}$ A=angle of a vector from lens center to the pixel, relative to the Optic Axis=AngleFromDistance(R/FocalLength, FocalLength)

B=correction for difference in area from rectangle tangent to sphere at angle A to rectangle parallel to focal plane=$1/\cos(A)$ C=correction for decrease in intensity with distance from source=$(FocalLength/(FocalLength\times \cos(A)))^2=1/\cos(A)^2$ P=total correction for projection=$B\times C=1/\cos(A)^3$ The value P is saved in the two-dimensional array Projection[i,j] for pixel at row i, column j. This completes subroutine CALCULATE PROJECTION CORRECTION; processing returns to the calling routine.

Figure 32:
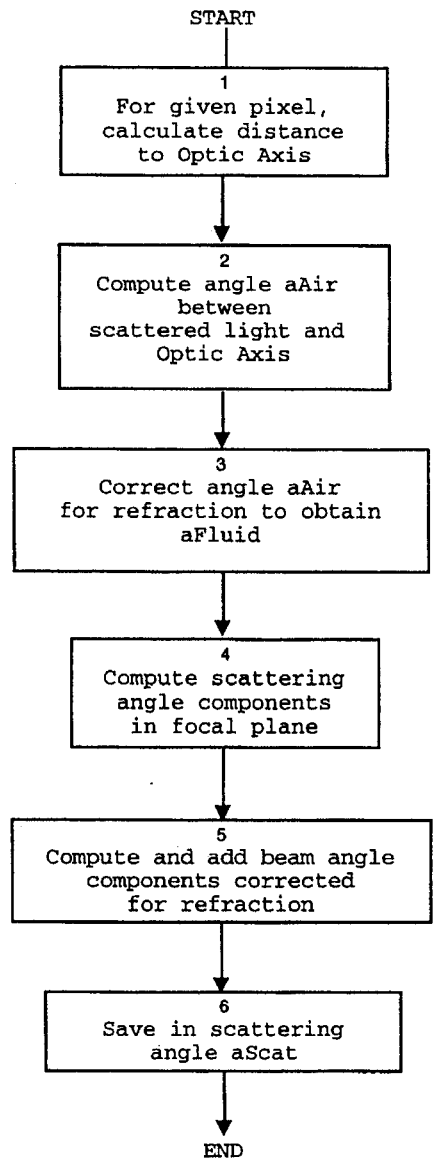
FIG. 32 is a flow chart for the routine CALCULATE SCATTERING ANGLE in an embodiment of the invention.

Subroutine CALCULATE SCATTERING ANGLE is shown in FIG. 32. In this subroutine, coordinates x, y, and z represent the following:
1. x=horizontal axis in the focal plane of the field lens (parallel to rows on the CCD)
2. y=vertical axis in the focal plane of the field lens (parallel to columns on the CCD)
3. z=optic axis (normal to the focal plane or CCD, and usually to the cell windows)

Figure 24A:
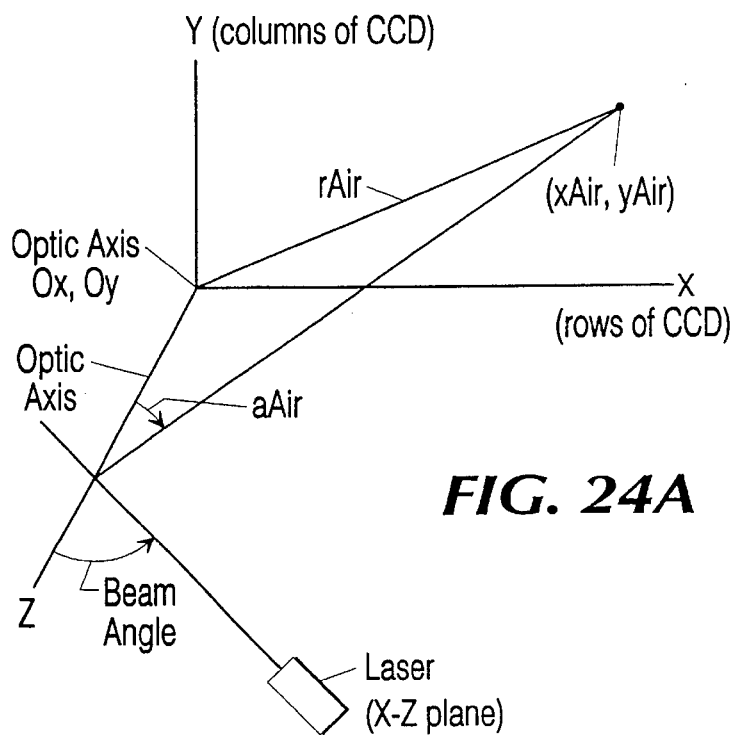
FIGS. 24A, 24B, 24C are oblique projections showing representative axes, angles, and distances used in the calculation of the scattering angle.
Figure 24B:
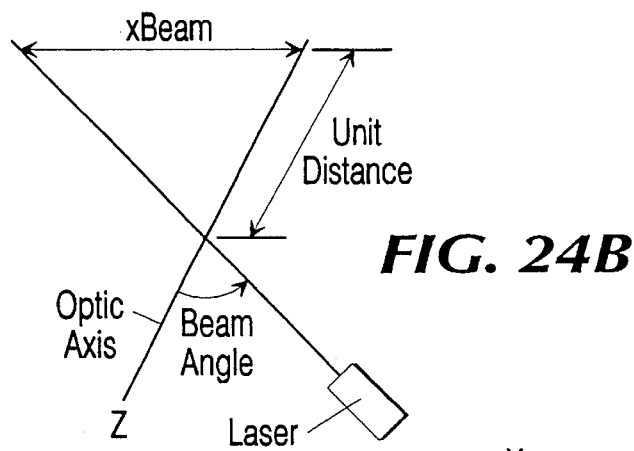
Figure 24C:
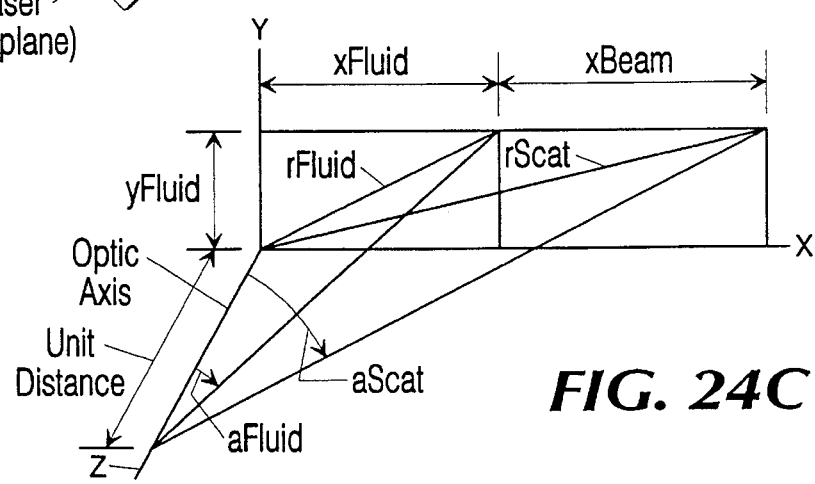

This coordinate system, some of the intermediate values computed by this subroutine, and the scattering angle aScat computed by this subroutine are shown in FIGS. 24A, 24B, and 24C. When the field lens 41 is used in the analyzer 10, the coordinate system is a virtual system based on the spatial Fourier transform provided by the field lens 41.

As shown in FIG. 24A and in block 1 of FIG. 32, given row and column coordinates for a point on the CCD (i.e., in the focal plane of the field lens), the distance from that point to the Optic Axis is computed in millimeters:
1. xAir=(row−Ox)*PixelWidth
2. yAir=(column−Oy)*PixelHeight
3. rAir=(xAir^2+yAir^2)^½

The angle from the normal to the focal plane (and, generally, to the cell window) is calculated. This is the angle of scattered light, after exiting the cell, that would strike the given point on the CCD:

aAir=AngleFromDistance(rAir,FocalLength)

Once the angle aAir is computed, the coordinate system in air of FIG. 24A can be dropped in favor of an analogous coordinate system in fluid as shown in FIGS. 24B and 24C. To move to the coordinate system in fluid, a correction is made for the angle for refraction at the cell window to get the angle in the cell:

aFluid=FluidFromAir(aAir)

As shown in FIG. 24C and in block 4 of FIG. 32, a computation is made of the length of a vector at this angle projected a unit distance in the z direction onto a plane normal to the optic axis:

rFluid=DistanceFromAngle(aFluid,1)

The x and y components of the vector are computed:
xFluid=xAir*rFluid/rAir
yFluid=yAir*rFluid/rAir As shown in FIG. 24B and in block 5 of FIG. 32, a computation is made of the length of a vector at the Beam Angle (corrected for refraction entering the cell) projected a unit distance onto a plane normal to the optic axis:

rBeam=DistanceFromAngle(FluidFromAir(BeamAngle),1)

Since the Beam Angle lies in the xz plane, the x component is equal to the vector, and the y component is zero:
xBeam=rBeam
yBeam=0

As shown in block 5 of FIG. 32, the beam vector components are added to the pixel angle components to get the scattering angle components:
xScat=xBeam+xFluid
yScat=yBeam+yFluid As shown in FIG. 24C, the x and y components are combined to get the length of a vector at the scattering angle projected a unit distance onto a plane normal to the optic axis:

rScat=(xScat^2+yScat^2)^½

Finally, the scattering angle is computed:

aScat=AngleFromDistance(rScat,1)

This completes subroutine CALCULATE SCATTERING ANGLE; processing returns to the calling routine.

It will be appreciated by those skilled in the art that modifications to the above method of calculating the scattering angle may be implemented, without departing from the spirit of the invention. For example, for scattering angles not near 90 degrees, the distance a pixel 55 lies relative to the center of the beam 22 in the plane of the pixel array may be used directly to calculate the scattering angle. For scattering angles near 90 degrees, it may be mathematically more precise to calculate the scattering angle with reference to a projection of the vector at the Beam Angle in a direction other than the direction of the optic axis, since in this situation the beam 22 is roughly perpendicular to the optic axis (parallel to the plane of the pixel array). This alternative is preferred for Beam Angles near 90 degrees, because, at these angles, projections of the vector at the Beam Angle will extend large distances and will not intersect the plane of the pixel array at a calculable distance from any given pixel.

Subroutine MEASURE BEAM INTENSITY (not shown) has the following steps: Take an exposure at the last recorded beam center Laser Drive Current and beam center Exposure Time, and call subroutine VALIDATE AND CORRECT PIXEL DATA. Call subroutine SCALE PIXEL DATA by Total Light Dose. Sum the scaled pixel data for all pixels within the beam intensity rectangle size rectangle of pixels centered at Beam Center. This is the measured beam intensity. This completes subroutine MEASURE BEAM INTENSITY; processing returns to the calling routine.

4. Sample or Baseline Analysis

Actual analysis involves the foregoing routines as well as three additional subroutines described as follows:

Subroutine CALCULATE BEAM TRANSMITTANCE FACTOR (not shown) calculates the transmission coefficient for the beam through the sample cell, using Beer's Law. PathLength is the length of the path of the incident beam through the cell at the current Beam Angle, relative to the path length when the beam is perpendicular to the cell windows. The variable alphaC is the exponent coefficient of path length for calculating beam transmittance by Beer's Law. Uncorrected Beam Transmittance is the measured beam intensity divided by the baseline beam intensity.

PathLength=1/cos(FluidFromAir(IncidentBeamAngle));

alphaC=log(UncorrectedBeamTransmittance)/PathLength;

BeamTransmittanceFactor=exp(alphaC).

This completes subroutine CALCULATE BEAM TRANSMITTANCE FACTOR; processing returns to the calling routine.

Figure 33A:
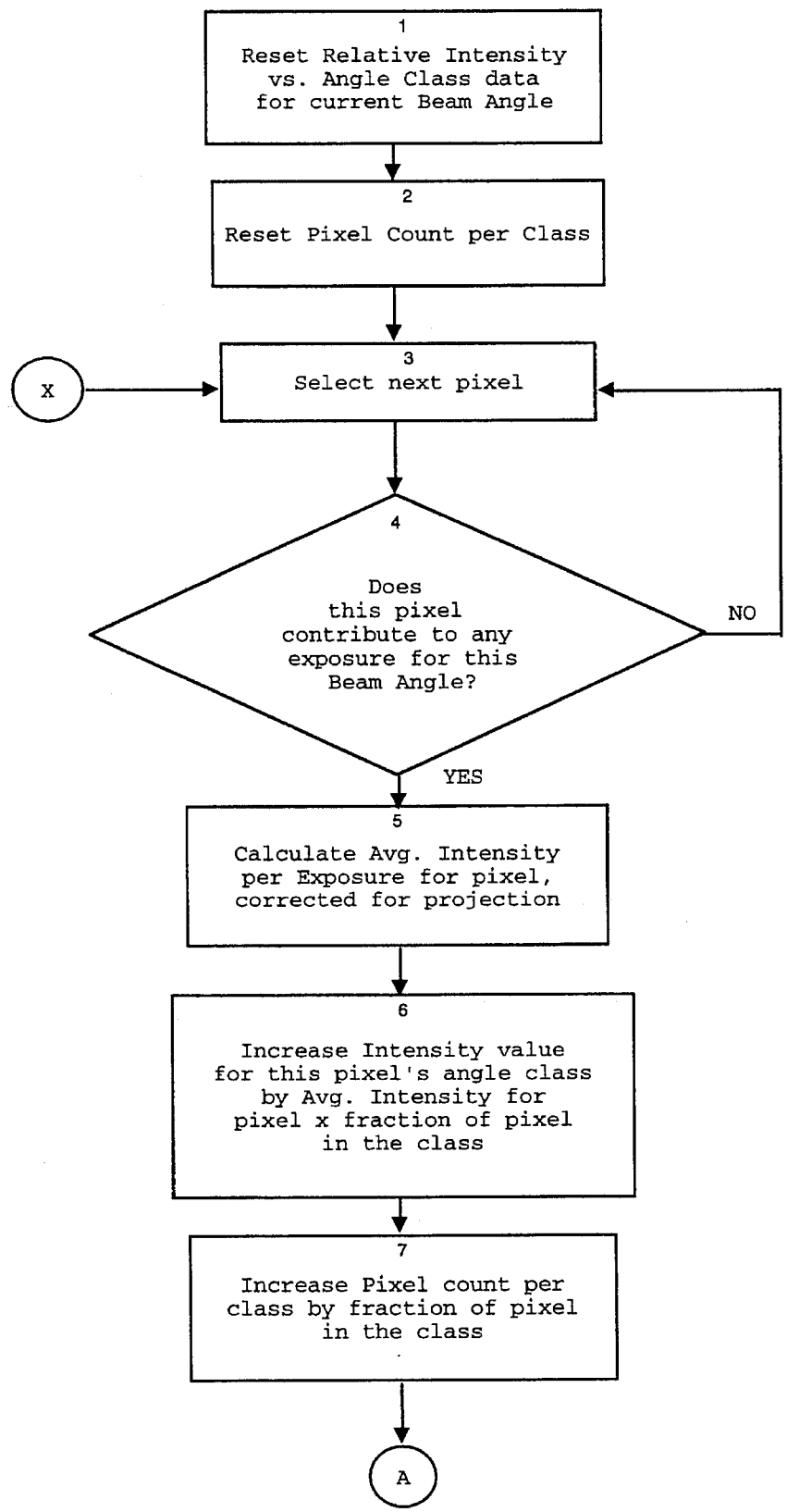
FIGS. 33A and 33B comprise a flow chart for the routine MAP PIXEL DATA TO ANGLE CLASSES in an embodiment of the invention.
Figure 33B:
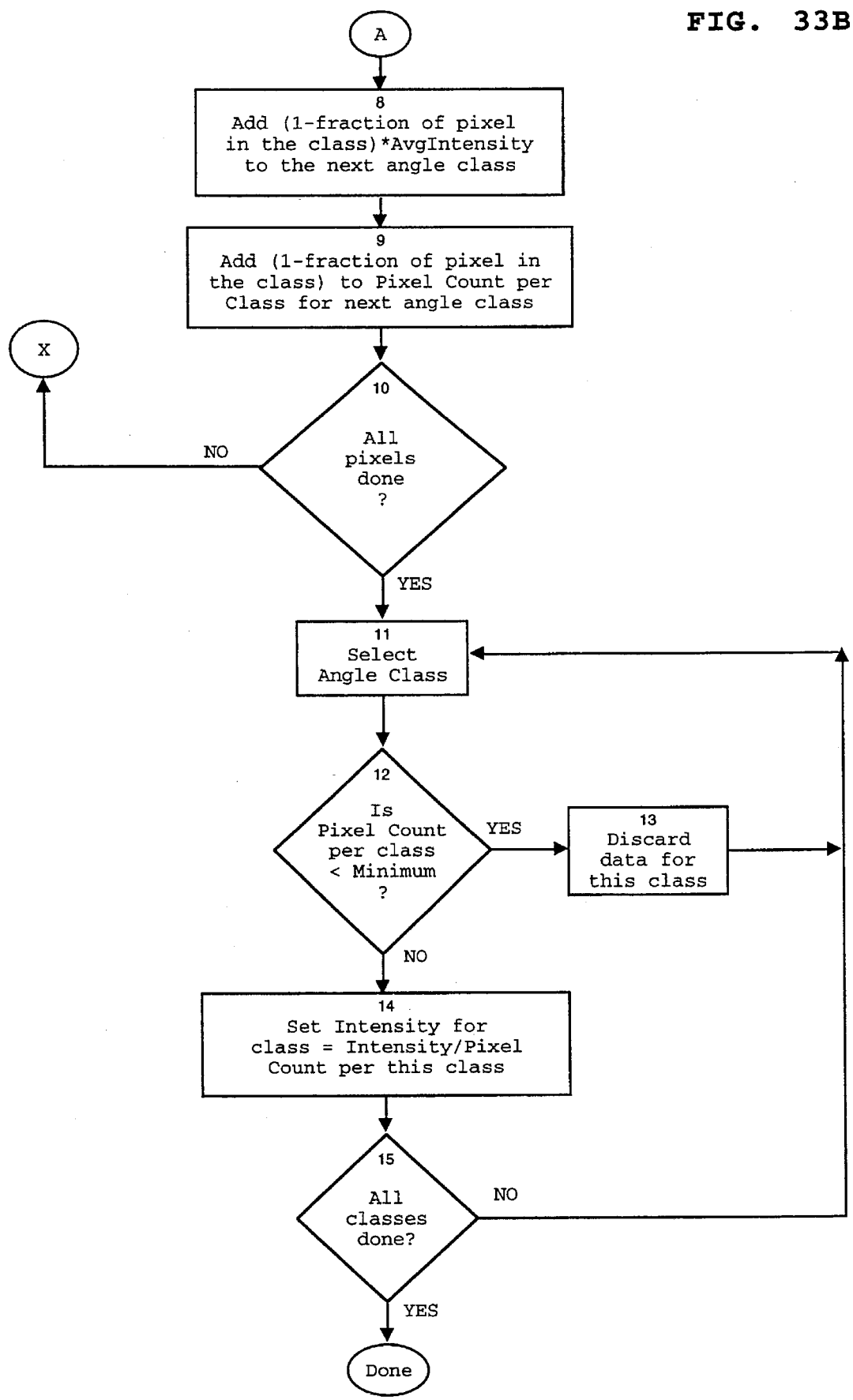

Subroutine MAP PIXEL DATA TO ANGLE CLASSES is shown in FIGS. 33A and 33B. The steps of this subroutine are as follows: Initialize the intensity-versus-angle-class data array, Intensity[m], to zero for the current incident Beam Angle. Initialize the PixelCountPerClass data array to zero. For each pixel[i,j] on the CCD, if the Aggregate Pixel Exposure Count is zero, skip to the next pixel. Otherwise, the average intensity is calculated for the readings in the CorrectedAggregatePixelData for this pixel, corrected for projection:

AveragePixelIntensity[i,j]=Projection[i,j]×CorrectedAggregatePixelData[i,j]/AggregatePixelExposureCount[i,j]

Let m be the angle class specified for pixel[i,j] by the pixel-to-angle class map InClass[i,j]. The following computations are made for the current incident Beam Angle:

1. Add AveragePixelIntensity[i,j]×InFrac[i,j] to Intensity [m].

2. Add PixelFractionInClass[i,j] to PixelCountPerClass[m].
3. Add AveragePixelIntensity[i,j]×(1−InFrac[i,j]) to Intensity[m+1].
4. Add (1−InFrac[i,j]) to PixelCountPerClass[m+1].

Processing continues with the next pixel.

As shown in blocks 11–15 of FIG. 33B, when all the pixels have been processed, compute the average intensity for each angle class m. Note that different values for Minimum Pixel Count Per Class may be used for small angles and large angles, to allow lower counts for small angles than for large angles. If PixelCountPerClass[m] is less than the predetermined minimum pixel count per class, discard the data for class m. Otherwise, set Intensity[m]= Intensity[m]/PixelCountPerClass[m]. If PixelCountPerClass is to be used as a weighting factor in further computation, it must be preserved in addition to the intensity data.

This completes the mapping of pixel data to angle classes for the current Beam Angle; processing returns to the calling routine.

Figure 34:
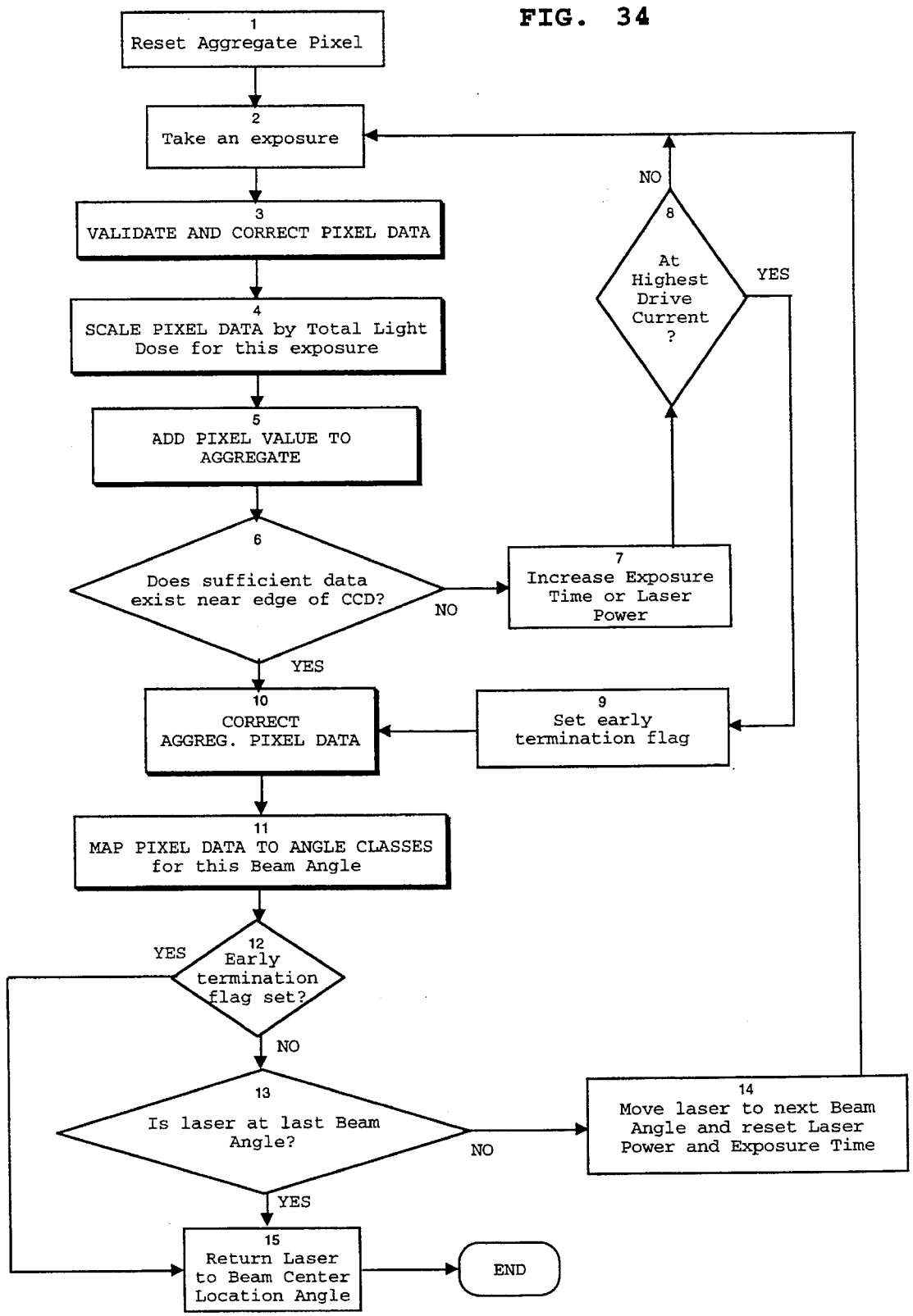
FIG. 34 is a flow chart for the routine COLLECT DATA in an embodiment of the invention.

The COLLECT DATA subroutine is shown in FIG. 34. A predetermined schedule of analysis Beam Angles, analysis Laser Drive Currents, and analysis Exposure Times for each analysis Laser Drive Current are used for data collection. Analysis Beam Angles include the Beam Center Location Angle (0 to −5 degrees) followed by angles from 5 degrees to 45 degrees in 5 degree increments. The analysis Laser Drive Currents are in the range of 0.1 milliamps to 50 milliamps. The analysis Exposure Times are in the range of 1 microsecond to 10 seconds.

The schedule is followed in order of increasing Beam Angle, increasing Laser Drive Current, and increasing Exposure Time for each Laser Drive Current. Termination of data collection at a Beam Angle is determined based on intensity data collected at that Beam Angle. Beginning Laser Drive Current and Exposure Time for each Beam Angle are based on the last values used at the previous Beam Angle. Termination of data collection occurs when sufficient data has been collected at the last Beam Angle, or when the maximum Laser Drive Current and Exposure Time have been reached without sufficient data being collected at the current Beam Angle, i.e. no further measurable Intensity data is available.

The following steps are executed to collect data:

1. Reset the Aggregate Pixel Data array to zero (block 1 of FIG. 34). Begin the following steps with the last recorded beam center Laser Drive Current and beam center Exposure Time.

2. Take an exposure, call subroutines VALIDATE AND CORRECT PIXEL DATA, SCALE PIXEL DATA BY TOTAL LIGHT DOSE, and ADD PIXEL DATA TO AGGREGATE PIXEL DATA (blocks 2–5).

3. Select a column of pixels (not a bad column) near the edge of the CCD farthest from Beam Center (such as column 5 if the current Beam Angle is the Beam Center Location Angle, or column 1275 for other Beam Angles). Using the Aggregate Pixel Exposure Count array, compute the average number of exposures taken containing valid readings for each pixel in the column excluding bad pixels. If the average is greater than or equal to the predetermined optimum number of exposures (preferably, 3 to 5 exposures), sufficient data has been collected at this angle. Call subroutines CORRECT AGGREGATE PIXEL DATA and MAP PIXEL DATA TO ANGLE CLASSES (blocks 6–11) and proceed to step 5 (block 13).

4. Change to the next higher analysis Exposure Time for the current analysis Laser Drive Current, if any. Otherwise, change to the next higher analysis Laser Drive Current and the lowest analysis Exposure Time for that analysis Laser Drive Current. If the highest analysis Laser Drive Current was already in use, call subroutines CORRECT AGGREGATE PIXEL DATA and MAP PIXEL DATA TO ANGLE CLASSES and proceed to step 6 (block 15). Otherwise, repeat from step 2 (block 2).

5. If the current analysis Beam Angle is the last, proceed to step 6 (block 15). Otherwise, move to the next analysis Beam Angle. Reset the analysis Laser Drive Current and analysis Exposure Time to the values used N exposures earlier, where N is the predetermined optimum number of exposures (block 1). Repeat from step 1.

6. Move the laser back to the Beam Center Location Angle (block 15). Collection of the sample or baseline intensity-versus-angle class data set is complete.

Generally speaking, sample analysis consists of loading a sample, adjusting the concentration, resuspending the sample, measuring the beam transmittance, collecting intensity-versus-angle data, and rinsing. Three basic methods are possible, based on the means of sample loading. Manually started analysis involves explicit operator command to start. Auto sampler analysis is started automatically based on an operator-entered schedule. Automatic sample sense is a mode in which the instrument circulates dispersant liquid and continually monitors beam transmittance to detect when a sample has been poured into the reservoir.

Figure 35:
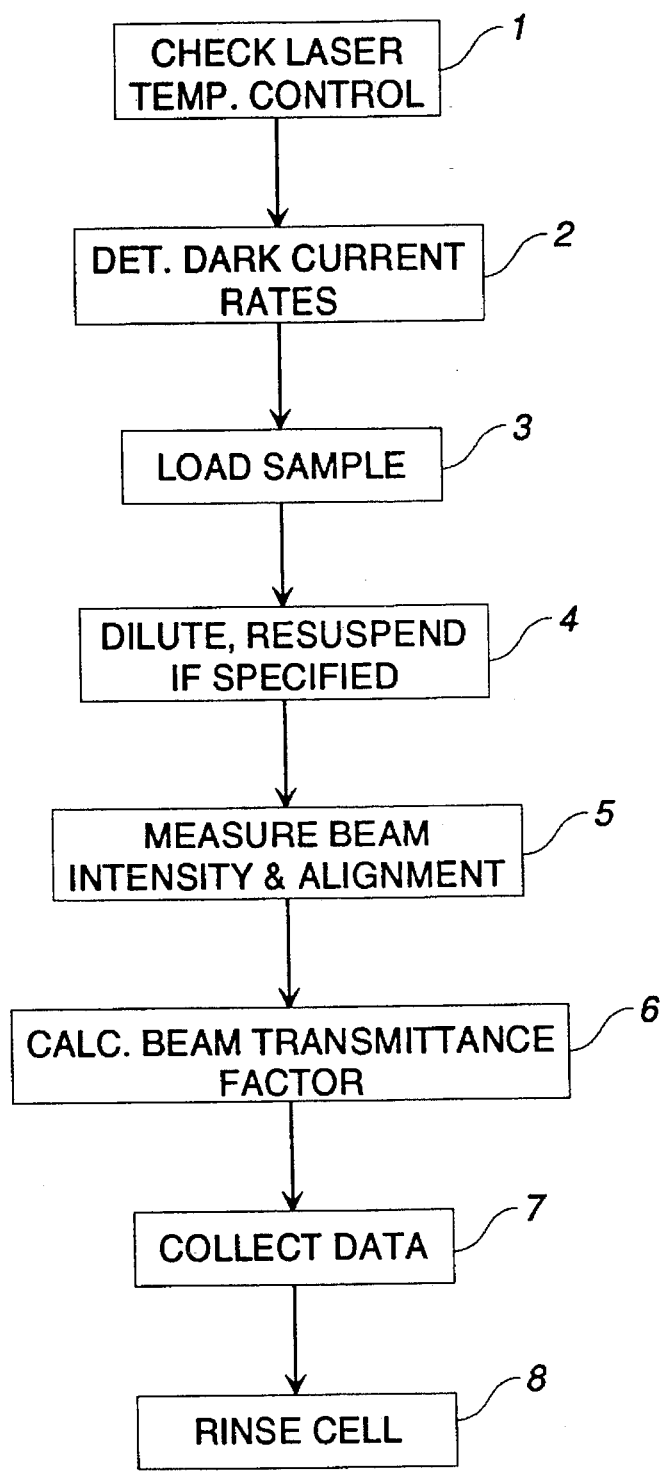
FIG. 35 is a flow chart for the routine SAMPLE ANALYSIS in an embodiment of the invention.

Referring to FIG. 35, sample analysis begins by calling the subroutines CHECK LASER TEMPERATURE CONTROL and DETERMINE DARK CURRENT RATES. When these checks have been updated, a sample is loaded into the reservoir 102 and circulated through the sample cell 31. The sample may be loaded in any of the three ways noted above. The probe 115 is operated as needed to assure that the particulate sample is dispersed in the dispersing fluid. If the sample is being delivered automatically from the autosampler 120, the valve 128 is closed and the valve 123 is opened to allow the autosampler pump to deliver sample in a conventional manner to the reservoir 102.

Next, the concentration of sample in the dispersing fluid is checked and adjusted if necessary, as shown in block 4 of FIG. 35. For optimal signal-to-noise results with minimal multiple scattering, the sample concentration should be adjusted by dilution or adding sample particles to cause a beam transmittance of about 70% to 85% of the baseline beam intensity. Concentration adjustment can be done manually by adding sample or opening the valve 111 to allow fluid to flow into the reservoir 102. The processor is programmed to display for the operator a real time readout of beam transmittance relative to baseline beam intensity, so that the operator can add fluid or sample until the transmittance is within the desired range.

Alternately, an autodilution routine (not shown) can be run, according to which a signal representing the beam intensity divided by the baseline beam intensity is monitored by the processor. If this value is less than the minimum optimal beam transmittance (for example 70%), the processor opens the valve 111 for a predetermined short interval to add fluid to the reservoir 102, diluting the sample and raising the transmittance. This process of monitoring and diluting is repeated until the transmittance is within the acceptable range. If the level sensor 117 indicates that the reservoir 102 is full, the processor opens the drain valve 140 for a preset time to lower the level of fluid before adding fluid from the supply 108.

As shown in block 5, when the concentration of sample is properly adjusted, all the subroutines of MEASURE BEAM INTENSITY AND ALIGNMENT (FIG. 28) are run to set up the angle classes on the CCD and measure the beam intensity. This procedure takes the place of mechanical alignment required for prior art analyzers, and assures that the angles assigned to the intensity data from the CCD detector are accurate. Next the subroutine CALCULATE BEAM TRANSMITTANCE FACTOR is run using the measured beam intensity divided by the baseline beam intensity as the uncorrected beam transmittance. The beam transmittance factor obtained is saved for later use.

Now the system is ready to run the subroutine COLLECT DATA as described above, for the selected schedule of analysis Beam Angles, Laser Drive Currents, and Exposure Times. Sets of intensity-versus-angle data are obtained for further processing as described below.

After the data has been obtained, the system may be rinsed (block 8) prior to loading another sample. The valve 128 may be opened to allow rinse liquid from the container 125 to flow into the reservoir 102, and the drain valve 140 may be opened to drain the prior sample to waste. The sensor 142 provides a signal when draining is complete. Several cycles of draining and circulating rinse liquid may be conducted to remove essentially all of the prior sample from the cell 31 and the reservoir 102. Furthermore, the rinse liquid may be provided via lines 126 and 122 to the autosampler 120 for rinsing procedures well known to those skilled in the art.

Baseline intensity data is obtained in a similar manner. Baseline data should be obtained at any time the sample cell 31 is manually cleaned or replaced and otherwise on a periodic (once a day or once a week, depending on use) basis. First, the CHECK LASER TEMPERATURE CONTROL and DETERMINE DARK CURRENT RATES subroutines are run. Then, the MEASURE BEAM INTENSITY subroutine is run with no particulate sample in the fluid circulating through the cell 31, to record the Baseline Beam Intensity. Then this value for beam intensity is used in the COLLECT DATA subroutine in the absence of sample particles to obtain Baseline Intensity data for use below.

5. Aggregate Corrected Intensity versus Scattering Angle Calculation

Certain subroutines are called, ultimately to obtain Aggregate-Corrected-Intensity-versus-Scattering-Angle data. For each incident Beam Angle, the subroutine CALCULATE REFLECTANCE and subroutine CALCULATE BEAM PATH LENGTH AND BEAM TRANSMITTANCE are called. For each scattering angle with sample intensity data and baseline intensity data at this incident beam angle, subroutine CORRECT SAMPLE INTENSITY FOR BASELINE INTENSITY, BEAM TRANSMITTANCE, AND REFLECTANCE is called. Subroutine COMBINE INTENSITY DATA FOR ALL INCIDENT BEAM ANGLES is then called. These subroutines (not shown) will now be described.

Subroutine CALCULATE REFLECTANCE calculates the reflectance of the anti-reflection coated glass used for the cell windows. It is calculated as a function of:

n1, refractive index of air (1.00)
n2, refractive index of coating (1.362)
n3, refractive index of fused silica glass (1.456)
a1, angle of incident beam to window in radians
h, thickness of coating (0.138 micrometers)
pi=3.14159
a2=asin(n1*sin(a1)/n2);
a3=asin(n1*sin(a1)/n3);

r12p=(n2*cos (a1)−n1*cos (a2))/(n2*cos (a1)+n1*cos (a2));

r23p=(n3*cos (a2)−n2*cos (a3))/(n3*cos (a2)+n2*cos (a3));

r12s=(n1*cos (a1)−n2*cos (a2))/(n1*cos (a1)+n2*cos (a2));

r23s=(n2*cos (a2)−n3*cos (a3))/(n2*cos (a2)+n3*cos (a3));

beta=2.*pi*n2*h*cos (a2);

rp=(r12p*r12p+r23p*r23p+2.*r12p*r23p*cos (2.*beta))/(1.+ r12p*r12p*r23p*r23p+2.*r12p*r23p*cos (2.*beta));

rs=(r12s*r12s+r23s*r23s+2.*r12s*r23s*cos (2.*beta))/(1.+ r12s*r12s*r23s*r23s+2.*r12s*r23s*cos (2.*beta));

Reflectance=(rp+rs)/2.

(Reference: Melles Griot Optics Guide 5 pg. 4–13 and 4–14, Melles Griot Inc.)

Subroutine CALCULATE BEAM PATH LENGTH AND BEAM TRANSMITTANCE (different from CALCULATE BEAM TRANSMITTANCE FACTOR described above) calculates the following factors:

PathLength=1/cos(FluidFromAir(IncidentBeamAngle));

alphaC=log(BeamTransmittanceFactor);

BeamTransmittance=exp(alphaC*PathLength).

Subroutine CORRECT SAMPLE INTENSITY FOR BASELINE INTENSITY, BEAM TRANSMITTANCE, AND REFLECTANCE collects and applies the above calculated factors. BaselineThreshold is a predetermined number between 0 and 1 (normally 0.3 to 0.5) representing the maximum allowable fraction of total light measured that can be attributed to baseline without causing an unacceptable amount of noise in the remaining corrected sample intensity data.

If (BaselineIntensity*BeamTransmittance> BaselineThreshold*SampleIntensity), exclude this intensity-versus-angle data point from further use. Otherwise, CorrectedSampleIntensity=(SampleIntensity− BaselineIntensity*BeamTransmittance)/((1−Reflectance)*(1− BeamTransmittance))

Subroutine COMBINE INTENSITY DATA FROM ALL INCIDENT BEAM ANGLES collects all the data from all the Incident Beam Angles into one Aggregate-Corrected-Intensity-versus-Scattering-Angle array. The steps of this routine are as follows: For each scattering angle, average the corrected sample intensity values for all incident Beam Angles having corrected sample intensity values at this scattering angle. If the PixelCountPerClass data was preserved in sample or baseline data collection, use a weighted average for this step, weighting each corrected sample intensity value by the associated PixelCountPerClass. In this case, compute an Aggregate Pixel Count Per Class by summing the PixelCountPerClass values used in averaging for this class.

6. Mie Scattering Models Calculation

Mie Scattering Models Calculation is based on the algorithm shown in Absorption and Scattering of Light by Small Particles by Bohren and Huffman, Copyright 1983 by John Wiley & Sons, Inc. Modifications to the algorithm are made to increase precision, remove calculation of backscattering angles, use a predetermined array of scattering angles, and optimize performance.

Size classes span the particle diameter range from 0.08 micrometers to 800 micrometers in a geometric progression.

A resolution between 20 classes per decade and 100 classes per decade can be chosen based on computation time for particle size distribution calculation, computation time for Mie scattering models, and stability of particle size distribution results for multiple analyses.

The computed intensity for a given angle class is the integral of scattered light intensity versus angle over the angle interval. The number of points calculated within each angle class for use in the integration is determined based on frequency of change in intensity with angle for the current particle size.

The scattering function for each size class may be the average of several Mie scattering curves for sizes spanning the interval of the size class to account for high frequency features that change too rapidly with size to be characterized accurately by an individual curve for each class. Alternatively, the scattering function for each class may be the weighted average of several Mie scattering curves for sizes overlapping with the sizes used to compute the adjacent classes, with the weighting factors based on, for example, a Gaussian distribution about the class mean.

The final construction of the size class data should be determined based on stability and goodness of fit of particle size distribution results. A set of Fraunhofer scattering data can also be provided for use when the refractive index of the sample is unknown, the sample is not of homogeneous composition, or for comparison with other data based on Fraunhofer scattering. Fraunhofer calculations may be substituted for Mie calculations for large particle sizes to reduce computation time.

7. Particle Size Distribution Calculation

The technique for calculating particle size distribution from scattered intensity-versus-angle data is preferably a Non-Negative Least Squares deconvolution (NNLS) with regularization by weighted minimization of the function. The NNLS algorithm is presented in *Solving Least Squares Problems* by Lawson and Hanson, Copyright 1974 by Prentice-Hall, Inc. The regularization method is presented in *The Solution of Adsorption Integral Equation by Means of the Regularization Method* by M. v. Szombathely and P. Brauer, University of Leipzig, Dept. of Chemistry, published in the *Journal of Computational Chemistry*, Vol. 13, No. 1, 17–32, Copyright 1992 by John Wiley & Sons, Inc.

The output data is preferably volume fraction per particle size class.

Intensity-versus-angle data used in the deconvolution may be truncated at the small angle end based on location of an intensity maximum. Large particle size classes may be excluded based on a minimum number of valid intensity data points available in the angle region of the primary lobe of the theoretical scattering pattern for those sizes. Small particle size classes may be excluded based on a minimum decrease in the theoretical scattered light intensity from the minimum angle with valid intensity data to the maximum angle with valid intensity data. Small particle size classes may also be excluded based on the requirement to have at least as many valid input data points as output classes.

The kernel matrix may be normalized by the total extinction for each size over the range of angles included, so that minimization of error (least squares) and minimization of the function (regularization) both evenly weight the response to all sizes. The problem may be transformed into a relative least squares problem by normalization of the kernel matrix and input vector by the input vector. The kernel matrix may be conditioned by weighting by a function of scattering angle, as described in *Optimizing the Kernel for Laser Diffraction Particle Sizing* by Y. C. Agrawal and H. C. Pottsmith, *Applied Optics* Vol. 32, No. 22, 1 Aug. 1993 and in *Optimal Scaling of the Inverse Fraunhofer Diffraction Particle Sizing Problem: the Linear System Produced by Quadrature* by E. D. Hirleman, *Particle Characterization* 4, 128–133 (1987). Alternatively, the kernel function may be conditioned by weighting by the Aggregate Pixel Count Per Class computed in the subroutine Combine Intensity Data from All Incident Beam Angles.

The threshold for determining class inclusion in the NNLS algorithm may be determined based on convergence of the deconvolution for a variety of particle size distributions. If necessary to prevent spurious addition of large amounts of small particle sizes to a distribution based on scattered light at wide angles at intensities below the instrument noise level, a two stage deconvolution may be used. If so, the first deconvolution should have a high threshold for class inclusion and should be used to limit the range of classes eligible for use in the second deconvolution. The second deconvolution should have a lower threshold for class inclusion but should exclude classes outside the limits defined by the first deconvolution. This technique becomes necessary if the single stage inversion process is unstable, given the set of angle classes chosen and the particle size distribution resolution desired.

It is efficacious to limit the maximum allowable number of deconvolution iterations. The value for the maximum may be determined based on the total number of size classes used.

While this invention has been described in detail with particular reference to preferred embodiments thereof, it will be understood that variations and modifications can be made to these embodiments without departing from the spirit and scope of the invention as described herein and as defined in the appended claims.

We claim:

1. A method of obtaining particle size distribution data for a group of dispersed particles, comprising the steps of:

illuminating a plurality of dispersed particles with a dose of light in a collimated beam from a light source for a plurality of distinct exposures;

passing at least a portion of said light scattered by said particles during said illuminating step through a lens such that rays parallel to one another are focused at one location in a focal surface of said lens;

detecting at least a portion of light rays of said beam scattered by said particles during said exposures with an array of light-sensitive elements;

varying in each of said exposures one or more characteristics of illumination of said particles;

reading output data from said elements following each of said exposures into a memory device;

determining from said output data intensity values for selected angle classes into which said light has been scattered for each of said exposures; and determining for each angle class a composite intensity value based on all of said exposures and scaled to compensate for differences in illumination characteristics during each of said exposures.

2. The method of claim 1, wherein said array of light-sensitive elements is the array of pixels in a CCD.

3. The method of claim 1, wherein said one or more illumination characteristics are selected from the group consisting of: duration of light dose, light source output level, path length through said particles.

4. The method of claim 1, wherein said illumination characteristic is light source output level, and wherein said step of scaling to compensate for differences in said illumination characteristic during each of said exposures comprises the steps of:

measuring the intensity of light transmitted toward said particles during a first exposure and a second exposure;

determining first and second doses of light transmitted toward said particles during said first exposure and said second exposure;

dividing said second dose by said first dose to obtain a scale factor; and adding to said intensity value for said second exposure the product of said intensity value for said first exposure value and said scale factor and averaging to obtain said composite intensity value.

5. The method of claim 1, wherein said illumination characteristic is duration of light dose.

6. The method of claim 5, wherein said duration of light dose is varied in a range from about 1 microseconds to about 10 seconds.

7. The method of claim 5, wherein said step of scaling to compensate for differences in duration of light dose during each of said exposures comprises the steps of:

measuring the duration of light doses transmitted toward said particles during a first exposure and a second exposure;

dividing said second duration by said first duration to obtain a scale factor; and adding to said intensity value for said second exposure the product of said intensity value for said first exposure value and said scale factor and averaging to obtain said composite intensity value.

8. The method of claim 1, wherein said illumination characteristic is light source output level, and wherein the step of varying said illumination characteristic comprises changing the level of current supplied to said light source.

9. The method of claim 1, wherein said illumination characteristic is path length through said particles, and wherein the step of varying said illumination characteristic comprises altering the incident angle of said light beam on said particles relative to an optic axis of said lens.

10. The method of claim 9, wherein said step of scaling to compensate for differences in said illumination characteristic during each of said exposures comprises adding to said intensity value for said second exposure the product of said intensity value for said first exposure and a scale factor obtained in accordance with Beer's Law, and averaging to obtain said composite intensity value.

11. The method of claim 1, wherein said step of determining composite intensity values comprises:

determining a scale factor between each of said exposures (n+1) and the preceding exposure (n, n≧1) by:

(a) normalizing intensity values for each exposure by dividing the intensity value associated with each angle class by the number of pixels in the same angle class;

(b) for each angle class, dividing each normalized intensity value for exposure (n+1) by the normalized intensity value for the exposure (n); and (c) weighting the quotient by the number of pixels contributing; and (d) calculating a weighted average of said quotients to obtain said scale factor;

and for each angle class;

multiplying the intensity value for the first exposure by the scale factor and adding the product to the intensity value for the second exposure and averaging to obtain a composite intensity value; and for each successive exposure (n+1), multiplying the existing composite intensity value by the scale factor between exposures (n+1) and (n), and adding the product to the intensity value for exposure (n+1) and averaging to obtain a cumulative composite intensity value.

12. A system for obtaining particle size distribution data for a group of dispersed particles, comprising:

a light source emitting a collimated beam of light;

a sample region capable of holding a plurality of dispersed particles, said region positioned in the path of said beam;

an exposure controller for operating said light source to illuminate said particles with a plurality of distinct exposures of said light beam, each differing in illumination characteristics;

an array of photosensitive pixels positioned to detect at least a portion of light rays from said beam scattered during said exposures;

a lens positioned to focus at least a portion of said scattered light onto said array of photosensitive pixels, rays parallel to one another being focused at one location;

a memory device connected to said array of photosensitive pixels to receive output data from said pixels following each of said exposures; and a processor configured (a) to determine from said output data intensity values for angle classes into which said light has been scattered for each of said exposures, and (b) to determine for each angle class a composite intensity value based on all of said exposures and scaled to compensate for differences in illumination characteristics during each of said exposures.

13. The system of claim 12, wherein said differing illumination characteristic comprises the size of a dose of light illuminating said particles during each of said exposures.

* * * * *